US011992307B2

United States Patent
Herr et al.

(10) Patent No.: US 11,992,307 B2
(45) Date of Patent: May 28, 2024

(54) METHOD FOR NEUROMECHANICAL AND NEUROELECTROMAGNETIC MITIGATION OF LIMB PATHOLOGY

(71) Applicant: Massachusetts Institute of Technology, Cambridge, MA (US)

(72) Inventors: Hugh M. Herr, Somerville, MA (US); Cameron Taylor, Cambridge, MA (US); Tyler Clites, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 310 days.

(21) Appl. No.: 16/754,351

(22) PCT Filed: Oct. 9, 2018

(86) PCT No.: PCT/US2018/055053
§ 371 (c)(1),
(2) Date: Apr. 7, 2020

(87) PCT Pub. No.: WO2019/074950
PCT Pub. Date: Apr. 18, 2019

(65) Prior Publication Data
US 2020/0305765 A1    Oct. 1, 2020

Related U.S. Application Data

(60) Provisional application No. 62/663,596, filed on Apr. 27, 2018, provisional application No. 62/570,343, filed on Oct. 10, 2017.

(51) Int. Cl.
*A61B 5/11* (2006.01)
*A61B 5/00* (2006.01)
(Continued)

(52) U.S. Cl.
CPC .............. *A61B 5/1107* (2013.01); *A61B 5/05* (2013.01); *A61B 5/4519* (2013.01);
(Continued)

(58) Field of Classification Search
CPC . A61B 5/0031; A61B 2034/2051; A61B 5/06; A61B 5/064; A61B 5/063;
(Continued)

(56) References Cited

U.S. PATENT DOCUMENTS 7,967,869 B2 *  6/2011  Schulman ................. A61F 2/78
                                                     623/33
10,912,512 B2    2/2021  Moradi et al.
(Continued)

FOREIGN PATENT DOCUMENTS

WO   WO-2016131020 A1 *  8/2016 ............. A61B 90/39
WO      2017025074 A1     2/2017

OTHER PUBLICATIONS

Sachs et al., "Development of a BIONic Muscle Spindle for Prosthetic Proprioception," in IEEE Transactions on Biomedical Engineering, vol. 54, No. 6, pp. 1031-1041, Jun. 2007, doi: 10.1109/TBME.2007.892924. (Year: 2007).*

(Continued)

*Primary Examiner* — David J. McCrosky
(74) *Attorney, Agent, or Firm* — Hamilton, Brook, Smith & Reynolds, P.C.

(57) ABSTRACT

A physiological feature of a subject is monitored by implanting a plurality of targets, such as magnets, and detecting at least one change in a physical property of the targets, followed by modifying a physiological feature of the subject in response to a change of state detected by the change in physical property detected in the targets. Cutaneous sensory feedback and proprioceptive feedback in a subject, as well (Continued)

as selective stimulation of axons or nerve fascicles of a neuron of a subject are provided.

24 Claims, 25 Drawing Sheets

(51) Int. Cl.
*A61B 5/05* (2021.01)
*A61F 2/48* (2006.01)
*A61F 2/68* (2006.01)

(52) U.S. Cl.
CPC .......... *A61B 5/4523* (2013.01); *A61B 5/6811* (2013.01); *A61F 2/48* (2021.08); *A61B 5/486* (2013.01); *A61B 2562/0223* (2013.01); *A61F 2002/6863* (2013.01); *A61F 2002/6872* (2013.01)

(58) Field of Classification Search
CPC ....... A61B 5/062; A61B 5/061; A61B 5/1107; A61B 90/39; A61B 2090/3904; A61B 2090/3908; A61B 2090/392; A61B 2090/3925; A61B 2090/3929; A61B 2090/3912; A61B 2090/3991; A61B 2090/397; A61B 2090/3975; A61B 2090/3979; A61B 5/1127; A61B 5/1126; A61B 5/4519; A61B 5/4523; A61F 2/68; A61F 2002/6863
USPC .................................................. 600/424, 431
See application file for complete search history.

(56) References Cited

U.S. PATENT DOCUMENTS

| | | |
|---|---|---|
| 2005/0070781 A1 | 3/2005 | Dawant et al. |
| 2007/0027460 A1 | 1/2007 | Case et al. |
| 2007/0167703 A1 | 7/2007 | Sherman et al. |
| 2008/0102096 A1 | 5/2008 | Molin et al. |
| 2008/0132800 A1 | 6/2008 | Hettrick |
| 2010/0249576 A1 | 9/2010 | Askarinya |
| 2011/0196262 A1 | 8/2011 | Mcleod et al. |
| 2013/0041235 A1 | 2/2013 | Rogers et al. |
| 2014/0213891 A1 | 7/2014 | Gilgunn et al. |
| 2016/0220828 A1 | 8/2016 | Yan Poon et al. |
| 2017/0230084 A1 | 8/2017 | Zhu et al. |

OTHER PUBLICATIONS

International Preliminary Report on Patentability for Int. Application No. PCT/US2018/055053, tilted, "Method for Neuromechanical and Neuroelectromagnetic Mitigation of Limb Pathology" date of mailing: Apr. 14, 2020.
Extended European Search Report for International Application No. EP 18 86 5684, entitled "Method for Neuromechanical and Neuroelectromagnetic Mitigation of Limb Pathology," consisting of 8 pages. Mailed: May 25, 2021.
International Search Report and Written Opinion for Int'l Application No. PCT/US18/55053, titled, "Method for Neuromechanical and Neuroelectromagnetic Mitigation of Limb Pathology", date of mailing Feb. 19, 2019.
Tarantino, S. et al., "A MyoKinetic HMI for the Control of Hand Prostheses: A Feasibility Study," Converging Clinical and Engineering Research on Neurorehabilitation II, 2 pages, First Online: Oct. 13, 2016.
W. Andrä et al., "A novel method for real-time magnetic marker monitoring in the gastrointestinal tract.," Phys. Med. Biol., vol. 45, No. 10, pp. 3081-3093, 2000.
Y. J. R. Ryoo, E. S. Kim, Y. C. Lim, Y. H. Chang, C. J. Moon, and S. H. Y. Yang, "Cancellation of background field using magnetic compass sensor for magnetometer based autonomous vehicle," Proc. IEEE Sensors 2003, vol. 1, pp. 52-57, 2003.
Nara, T., "Takaaki Nara: Research Theme". Oct. 18, 2023. http://www.inv.ipc.i.u-tokyo.ac.jp/naratheme_e.html.
International Search Report and Written Opinion received for PCT Patent Application No. PCT/US2021/056092, mailed on Feb. 24, 2022, 11 pages.
Tarantino, et al., "The Myokinetic Control Interface: Tracking Implanted Magnets as a Means for Prosthetic Control," Scientific Reports; 7:17149 (Dec. 7, 2017).

* cited by examiner

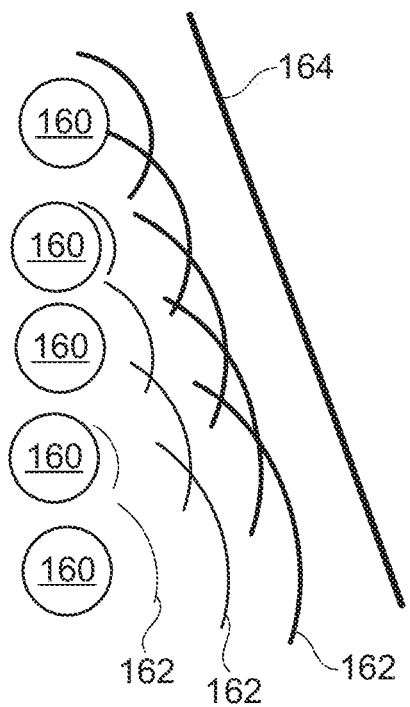
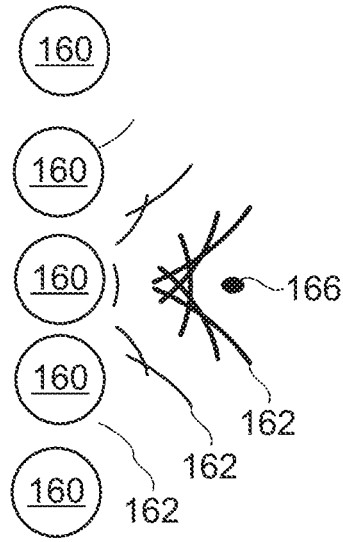
FIG. 13A
Prior Art
FIG. 13B
Prior Art
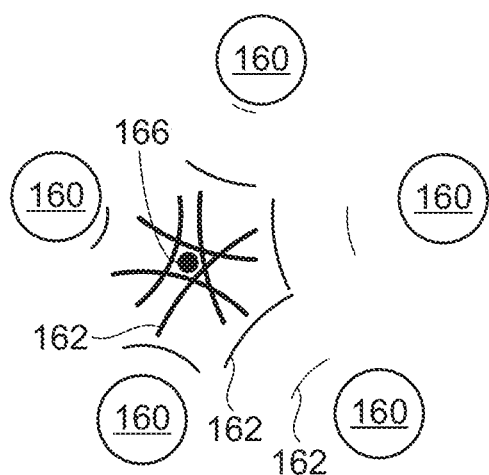
FIG. 13C
Prior Art

METHOD FOR NEUROMECHANICAL AND NEUROELECTROMAGNETIC MITIGATION OF LIMB PATHOLOGY

RELATED APPLICATIONS

This application is the U.S. National Stage of International Application No. PCT/US2018/055053, filed Oct. 9, 2018, which designates the U.S., published in English, and claims the benefit of U.S. Provisional Application No. 62/570,343, filed on Oct. 10, 2017 and 62/663,596, filed on Apr. 27, 2018. The entire teachings of the above applications are incorporated herein by reference.

BACKGROUND

Volitional control of wearable robotics, such as prostheses, orthoses or exoskeletons, requires sensing of intent from the wearer. Though there are various methods for acquiring signaled intent from the wearer, limitations such as signal-to-noise ratio, level of invasiveness, and limited degrees of freedom, keep high-resolution, high fidelity control from being a reality. Electromyographic (EMG) signals from residual muscles are sometimes limited in signal quality because the target muscles lie deep within the biological limb, and hence cannot be easily accessed, independently isolated, or measured consistently. Consequently, functional control of wearable robotic devices through transdermal recording platforms, such as surface EMG (sEMG), is limited, and users experience frustration due to poor function. As a resolution to these difficulties, implanted electrodes using wired or wireless approaches have been explored for the measurement of EMG muscle signals. Unfortunately, these approaches are sometimes highly invasive, requiring surgery and the placement of complex electronics into the body such as electrodes, connectors and telemetry elements.

The majority of state-of-the-art powered prosthetic systems controlled extrinsically using neural signals are done so via these imperfect EMG measurements. However, EMG alone cannot provide sufficient information to accurately interpret intended movement. Because muscle force production is dependent on muscle activation as well as fascicle length and velocity, access to muscle state (length and speed) measurements are necessary to enable an efferent control modality that replicates biological muscle function with high fidelity. Muscle state information is also essential for precise modulation of muscle state and perceived joint torque via external muscle stimulation. Unfortunately, there currently exists no robust methodology of measuring real-time muscle state in living humans as part of a chronically wearable system.

Therefore, a need exists for a method for mitigation of limb pathology that overcomes or minimizes the above-mentioned problems.

SUMMARY

The invention generally is directed to a method for neuromechanical and neuroelectromagnetic mitigation of limb pathology.

In one embodiment, the invention is a method for detecting a physical property of tissue that includes implanting a plurality of targets at a tissue of a subject and employing an array of sensors to detect at least one state of the targets relative to each other, wherein the state of the targets is indicative of a physical property of the tissue, thereby detecting the physical property of the tissue.

In another embodiment, the invention is a method of modulating feedback. In this embodiment, the method includes affixing at least one magnetic component at a tissue and applying an array of electromagnetic coils to the tissue proximate to the at least one magnetic component, whereby establishing a magnetic field across the array of electromagnetic coils causes an electromagnetic reaction by the at least one magnetic component, thereby modulating feedback.

Another embodiment for providing cutaneous sensory feedback in a subject by the method of the invention includes the steps of applying a tactile array to a first cutaneous surface of the subject, the tactile array being linked to sensors at a second cutaneous surface of the subject remote from the first cutaneous surface of the subject. Signals are transmitted from the sensors at the second cutaneous surface of the subject to the tactile array at the first cutaneous surface of the subject, thereby providing cutaneous sensory feedback to the subject.

In another embodiment, the invention is a method for providing proprioceptive feedback to a subject. In this embodiment, the method includes the steps of affixing at least one magnetic target at a pair of muscles in agonist-antagonist relation to each other. A signal representing an applied force is detected, and an electromagnetic field is selectively generated consequent to the detected signal, thereby causing the at least one magnetic target to apply a force to the pair of muscles in agonist-antagonist relation to each other, whereby an afferent signal is generated by the agonist-antagonist muscle pair, thereby providing proprioceptive feedback to the subject.

In another embodiment of a method for providing proprioceptive feedback in a subject of the invention, targets are implanted at the pair of muscles in agonist-antagonist relation to each other. At least one state of a portion of the targets is detected, thereby detecting a state of the agonist-antagonist pair of muscles. An afferent signal is generated consequent to the change of state of the agonist/antagonist pair of muscles, thereby providing proprioceptive feedback in the subject.

In yet another embodiment, the invention is a method for selectively stimulating at least a portion of axons or nerve fascicles of a neuron of a subject comprising the steps of placing a cuff at or proximate to a neuron of a subject, the cuff including one or more antennas at or proximate to the cuff and collectively extending about at least a portion of a circumference of the neuron, thereby forming an array of the antennas about the neuron. Electromagnetic waves are selectively generated at the one or more antennas, whereby the electromagnetic waves are focused at a subset of at least one member of the group consisting of axons and nerve fascicles of the neuron, thereby causing depolarization of the subset and consequent selective stimulation of at least a portion of the axons or nerve fascicles of the neuron of a subject.

Another embodiment of the invention is a method for detecting a state of one or more objects that includes providing one or more targets at each of the one or more objects and positioning an array of sensors proximate to the one or more targets, whereby a signal from the targets at the sensors is detected. The parameters describing the state of each of the one or more targets are then estimated and predicted values of the signal at each of the sensors are calculated given these estimates of the parameters, whereby a prediction error in the predicted values of the signal with reference to the values of the signals detected at the sensors is computed. A prediction error Jacobian matrix is then calculated by analytically computing elements of the prediction error Jacobian matrix, and the prediction error in combination with the prediction error Jacobian matrix are used to determine a state of the at least one target, whereby the state is indicative of a physical state of the one or more objects.

In yet another embodiment, the invention is a method for detecting a state of one or more objects while compensating for a disturbance field that includes providing one or more targets at each of the one or more objects and positioning an array of sensors proximate to one or more targets, whereby a signal from the targets at the sensors is detected. The parameters describing the state of each of the one or more targets are then estimated, and the parameters of the disturbance field are also estimated, and predicted values of the signal at each of the sensors are calculated given these estimates of the parameters, whereby a prediction error in the predicted values of the signal with reference to the values of the signals detected at the sensors is computed. A prediction error Jacobian matrix is then calculated, and the prediction error in combination with the prediction error Jacobian matrix are used to determine a state of the one or more targets, whereby the state is indicative of a physical state of the one or more objects.

A method for detecting a state of one or more objects includes the steps of: providing one or more targets at each of the one or more objects; positioning an array of sensors proximate to the one or more targets, whereby a signal from the targets at the sensors is detected; estimating parameters describing the state of each of the one or more targets; calculating, in a cascading calculation, predicted values of the signal at each of the sensors given the estimates of the parameters; computing a prediction error in the predicted values of the signal with reference to the values of the signals detected at the sensors; calculating a prediction error Jacobian matrix; and determining from the prediction error and the prediction error Jacobian matrix a state of the one or more targets, whereby the state is indicative of a physical state of the one or more objects.

A method for determining one or more of three sensor positions and three sensor orientations for each of the sensors in a sensor array includes the steps of: placing at least one target in at least one known location relative to a sensor array, whereby a signal from the at least one target at the sensors is detected, and recording at least one measurement of the signal at each of the sensors for each placement of the one or more targets; estimating one or more parameters from the group consisting of x-position, y-position, z-position, yaw, pitch, and roll, of each of the sensors; estimating any unknown state parameters of the at least one target; calculating predicted values of the signal at each of the sensors for each of the measurements given the estimates of the sensor parameters and target states; computing a prediction error in the predicted values of the signal with reference to the values of the signals detected at the sensors; calculating a prediction error Jacobian matrix by analytically computing elements of the prediction error Jacobian matrix with respect to the estimated parameters of the sensors for each measurement; and determining from the prediction error and the prediction error Jacobian matrix a state of the parameters of the sensors.

In an embodiment, the method further includes the steps of: implanting at least one magnet at each of at least one respective tissue of a subject; applying the array of magnetometers to the subject proximate to the at least one magnet, whereby a position of the magnet relative to the array of magnetometers is determined, the position being indicative of a physical property of the tissue of the subject; and modifying a physiological feature of the subject that affects or is affected by the physical property of the tissue of the subject, thereby modulating the physiological feature of the subject.

In an embodiment, the method further includes the steps of: rotating the array of magnetometers about each of three coordinate axes in a uniform magnetic field while collecting a three-axis data stream from each of the magnetometers; calibrating each of the magnetometers in the array by determining hard iron offsets and soft iron distortions; scaling gains of the magnetometers with respect to one another; and determining rotation matrices that map the three-axis data streams from the magnetometers into a common coordinate system, whereby relative sensor orientations are determined.

A device for detecting a physical property of tissue includes an array of sensors to detect a plurality of targets at a tissue, and electronics to determine at least one state of the targets relative to each other and provide an indication of a physical property of the tissue.

This invention has many advantages. For example, in one embodiment, the invention is generally directed to treatment of limb pathology resulting from disease or traumatic injury. In another embodiment, the invention is directed to human augmentation to enhance human physicality beyond normal physiological limits. In the realm of permanent assistance devices, for example, the invention can preserve post-amputation function in a residuum of an amputee, and restore natural muscle control function in paralyzed or weakened limbs due to age-related degeneration, spinal cord injury, or other neuromuscular pathologies.

The invention can employ an implant system with no active electronics within the body, thereby obviating the need for a wired or wireless transmission of power through the skin. The method of the invention eliminates the need for a percutaneous connection in the case of a wired transmission, eliminating the potential for infection, inflammation, or other complications related to percutaneous wire passage. Further, the method eliminates the need for complex implanted electronics that all too often require repeated surgical procedures for maintenance and repair after extended periods of time within the body.

Sensor architecture employed in an embodiment of the invention provides accurate real-time fascicle state information synchronously with reliable, repeatable force data that enables an efferent control paradigm to produce a precise interpretation of intended joint position, torque and impedance. One example of such a control architecture, in its simplest implementation, is a master-slave control paradigm used to control an actuated joint within a wearable robotic system from measured muscle state within the biological limb. In this paradigm, muscle lengths and speeds can be employed as control targets by the wearable robotic device processors wherein, for example, motors are driven to output artificial joint positions and speeds corresponding to targets obtained using an anatomically-derived transformation from the linear muscle space to a rotary joint space of the wearable system.

In another controller implementation employed in an embodiment of the invention, a wearable device that provides robotic joint torque and impedance is controlled in a strategy that first estimates muscle force from EMG and muscle state using a biophysical muscle model. From this force estimate a corresponding biomimetic torque control target is computed using an anatomically-derived transformation from the linear muscle space to a rotary joint space of the wearable device. Biophysical models of muscle, such as the Hill Muscle Model, are able to predict muscle force from measurements of EMG and fascicle state. EMG can be measured using a number of strategies including surface electrodes, wired epimysial electrodes, or wireless intramuscular electrodes. The EMG signal can then be employed to estimate muscle activation through a model of activation dynamics which describe propagation of an electrical signal throughout the muscle and subsequent temporal properties of muscle contraction, primarily related to calcium release dynamics in individual motor units. Activation then serves as the input to a fascicle length and contraction-velocity dependent model of force production. If these parameters are measured directly, the fully characterized model provides an accurate real-time estimate of force production. With these measurements, it is then possible to reproduce those dynamics in an actuated, computer-controlled prosthetic, orthotic or exoskeletal joint.

In yet another controller implementation employed in an embodiment of the invention, muscle force is measured directly, and motors on the wearable device are driven to output artificial joint torques corresponding to targets obtained using an anatomically-derived transformation from the linear muscle space to a rotary joint space of the device.

Fascicle state and force sensing also has the potential to improve fidelity of muscle control using artificial stimulation. With accurate muscle state and force feedback, a closed-loop control of muscle stimulation employed in one embodiment of the invention allows precise modulation of the state or force of a muscle. Muscle stimulators are inherently imprecise, and it is extremely difficult to model physiological response to artificial stimulation, which makes an open-loop stimulation paradigm extremely difficult to manage.

A closed-loop stimulation paradigm, such as is employed in one embodiment of the invention, overcomes these issues, allowing precise modulation of muscle force and length.

In another embodiment of the invention, fascicle state and force sensing can be employed to monitor biomechanical tissue function in humans as a means to prevent or mitigate injury in work and athletic applications.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. The same number present in different figures represents the same item.

FIG. 13A is a schematic representation of a prior art linear array of antennas that employs phase offsets to cause a wave to change direction by electronically controlling phase differences between electromagnetic wave crests from each antenna.

FIG. 13B is a prior art arrangement of a linear array of antennas that is employed to cause symmetric phase shifting that results in electronically-focused electromagnetic waves at a focal point.

FIG. 13C is a prior art arrangement of a circular array of antennas that is employed to create an electromagnetic focal point by phase shifting of electromagnetic wave crests.

DETAILED DESCRIPTION

Figure 1A:
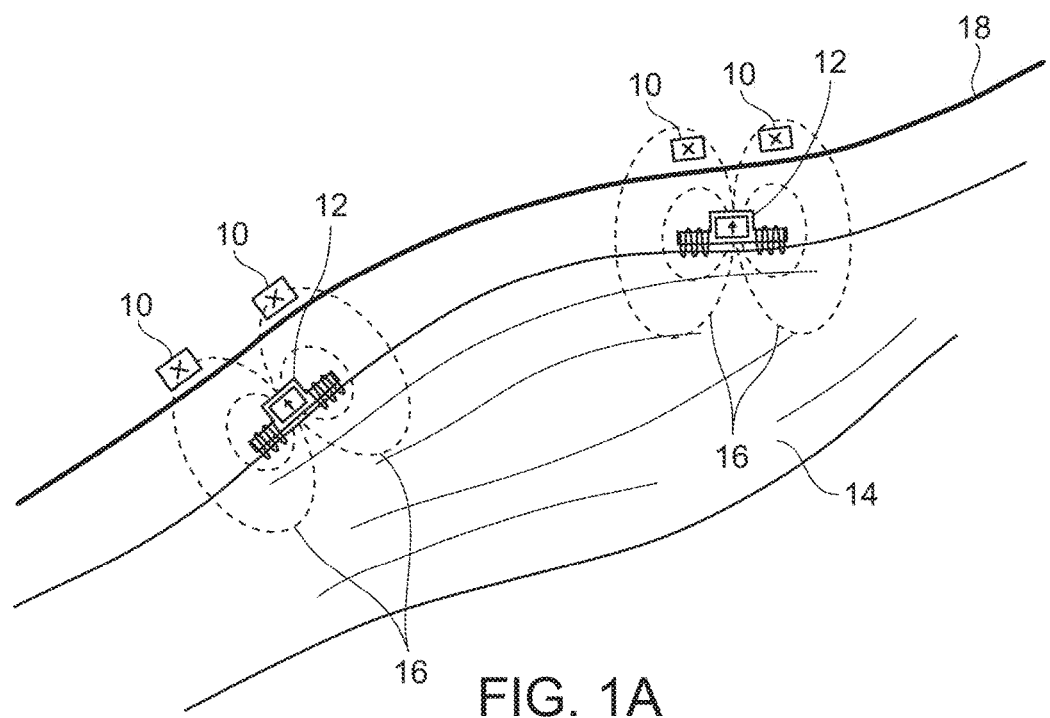
FIG. 1A is a schematic representation of magnetic fields of an implanted permanent magnet on a muscle at rest as employed in one embodiment of a method of the invention.

A description of example embodiments follows.

In one embodiment the method includes implanting a plurality of targets at a tissue of a subject and detecting at least one state of the targets relative to each other, wherein the state of the targets is indicative of a physical property, thereby detecting the physical property. As defined herein, a "state" of a target, or targets, includes at least one of any of the members of the group consisting of the position, orientation, and strength of the target or targets. Specifically, the "state of the targets relative to each other" includes at least one of any of the members of the group consisting of the relative positions of the targets, the distance between the targets, and the relative orientation between the targets.

In one specific embodiment, the targets are active targets. As defined herein, an "active target" is defined as a target that requires a dedicated power storage element, such as a battery or a capacitor, which is part of or physically connected to the target. A few examples of active targets include battery-driven electromagnets, resonant coils containing capacitors which are charged via a time-varying externally-applied electromagnetic field, battery-driven piezoelectric acoustic transducers, and targets with built-in sensing and communication capability. Alternatively, the targets are passive targets. In yet another embodiment, the targets are implanted in the tissue. In another embodiment, the physical property detected is a change in physical property of the tissue. In still another embodiment, a change in a state of the targets relative to each other is detected, wherein the change in the state of the targets is indicative of yet another physical property, thereby detecting the additional physical property.

In a specific embodiment, a physiological feature of the subject is then modified in response to the detected physical property of the tissue, thereby modulating the physiological feature of the subject.

In a specific embodiment, the tissue is a muscle, and the targets are a pair of targets spaced apart from each other, whereby contraction or relaxation of the muscle causes the targets to move closer to or further from each other, respectively. Examples of suitable targets include those that include a material selected from the group consisting of a permanent magnetic material and a temporarily magnetizable material.

In an embodiment wherein the targets include a temporarily magnetizable material, the method further includes the step of generating a magnetic field via elements which are distinct from the targets, and further includes the step of exposing the targets to the magnetic field. In one such embodiment, the magnetic field is generated by at least one member of the group consisting of a permanent magnet and an electromagnetic coil. In a specific embodiment, the method further includes the step of placing the at least one permanent magnet, or the at least one electromagnetic coil, at a surface of the subject.

In another embodiment, the at least one state is detected by a magnetometer. Examples of suitable magnetometers include a Hall effect sensor, a passive electromagnetic coil, a magnetoresistor, a magneto-inductive sensor, a fluxgate magnetometer, and a superconducting quantum interference device (SQUID) magnetometer.

In another embodiment, the at least one state is detected by at least one member of the group consisting of a three-axis magnetometer, a two-axis magnetometer and the combination of two single-axis magnetometers. In still another embodiment, the targets are permanent magnets and the permanent magnets have five degrees of freedom. Typically, the physical property of the tissue is determined by detecting both the position and the orientation of the permanent magnets relative to each other, such as by use of at least ten single-axis magnetometers, or at least four three-axis magnetometers.

In another embodiment, the at least one change in the at least one physical property of the targets is detected by a magnetometer at a surface of the subject proximate to the targets. Independently, at least one of the targets can be implanted in a surface of the muscle, or can be implanted within the muscle, or both. In still another embodiment, at least one of the targets can be implanted within a tendon of the subject.

In yet another embodiment, the detected physical property includes at least one member of the group consisting of: a contraction or relaxation of skeletal, cardiac, or smooth muscle; a bone bending; a bone stretching; a lung inflation; a peristalsis; a vasoconstriction; a vasodilation; a skin stress; a skin strain; a position of at least one bodily organ; a volume of at least one bodily organ; and a length of at least one bodily organ. For example, the bodily organ can include at least one member of the group consisting of: a liver; a pancreas; a kidney; a bladder; a tooth; a tongue; and a reproductive organ. In yet another embodiment, the detected physical property is monitored over time, whereby a change in the physical property is detected.

In another embodiment, the plurality of targets includes at least one member of the group consisting of a magnetic material and an electrically conductive material. In this embodiment, the plurality of targets are placed at at least one member of the group consisting of a muscle and a tendon. In one version of this embodiment of the invention, the method further includes the step of positioning at least one electromagnetic coil at a surface of the subject, or externally and apart from the subject. In this embodiment, the method of the invention can include the additional step of generating an electromagnetic field by the at least one electromagnetic coil. In this embodiment, the method can also further include the step of detecting the state of the targets by detecting an inductance of the at least one magnetic coil as part of the system composed of the at least one magnetic coil and the targets, such as wherein the inductance is inferred from measurement of electric current through the at least one electromagnetic coil when the electromagnetic coil is driven with a varying voltage signal.

In still another embodiment, the method can further include the step of measuring at least one member of the group consisting of impedance and resonant frequency of the at least one electromagnetic coil, wherein the electromagnetic coil is arranged in parallel with capacitors. In another embodiment, the method further includes the step of detecting at least one state of the targets by detecting an inductive coupling between a pair of electromagnetic coils. Inductive coupling can be sensed, for example, as a consequence of driving one electromagnetic coil of each pair of the electromagnetic coils, wherein the at least one state of the targets is detected by monitoring the voltage or the current in the corresponding coil in each electromagnetic pair.

In yet another embodiment of the invention, the targets have a density distinct from that of the tissue at which they are implanted, and at least one state of the targets is detected by exposing the targets to ultrasound and detecting the latency of one or more echoes reflected by the targets. Examples of suitable targets can include at least one member of the group consisting of titanium, stainless steel, tantalum, and vanadium steel. In one such embodiment, the targets include a coating of a biocompatible material, such as a material that includes at least one member of the group consisting of: a bioceramic; parylene; glass; silicone; titanium; and a biocompatible polymer.

It is to be understood that, in any of these embodiments, the tissue of the subject can be a pair of muscles in agonist-antagonist relationship to each other, whereby the change in state of tissue is a change in the state of the agonist-antagonist pair of muscles.

In another embodiment, the invention is a method of modulating feedback, such as feedback to a subject. In this embodiment, the method includes affixing at least one magnetic component at a tissue, and applying an array of electromagnetic coils to the tissue proximate to the at least one magnetic component, whereby establishing a magnetic field across the array of electromagnetic coils causes an electromagnetic reaction by the at least one magnetic component, thereby modulating feedback.

In one embodiment, the tissue is of a subject, whereby the feedback is to the subject. In another embodiment, the feedback is sensory feedback, such as cutaneous sensory feedback.

In one embodiment, the method further includes the step of manipulating the electromagnetic field of the array of electromagnetic coils, thereby changing the feedback in the subject. In another embodiment, the electromagnetic field is manipulated in response to sensors at the tissue. In still another embodiment, the electromagnetic field is manipulated in response to sensors at a bionic limb.

In one version of this method of the invention, the tissue is a skin graft that is ectopic and the locations of the sensors at the bionic limb correspond to locations of nerves at the ectopic skin graft, whereby the reaction of the at least one permanent magnet simulates sensation of a biological limb to which the ectopic skin graft is native. In another embodiment, innervating nerves of the ectopic skin graft are native to the ectopic skin graft. Also in this embodiment, the method can further include the step of implanting the ectopic skin graft beneath a native skin surface of the subject.

In another embodiment, the skin graft is denervated and at a distal end of a transected cutaneous nerve, whereby the skin graft is reinnervated. In this embodiment, the skin graft can be vascularized, at the time of implantation.

Alternatively, the skin graft is innervated, wherein the skin graft will vascularize after implantation. In still another embodiment, the skin graft revascularizes and reinnervates following implantation.

In another embodiment, the at least one magnetic component includes is an array of magnets, such as an array of magnets wherein each magnet is fixed in position relative to each of the other magnets of the array prior to implantation in the skin graft. The at least one magnetic component can include at least one member of the group consisting of a permanent magnetic material and an electromagnetic material.

Another embodiment for providing cutaneous sensory feedback in a subject by the method of the invention includes the steps of applying a tactile array to a first cutaneous surface of the subject, the tactile array being linked to sensors at a second cutaneous surface of the subject remote from the first cutaneous surface of the subject. Signals are transmitted from the sensors at the second cutaneous surface of the subject to the tactile array at the first cutaneous surface of the subject, thereby providing cutaneous sensory feedback to the subject. In one such embodiment, the tactile array includes at least one member of the group consisting of: solenoids; linear motors; and rotary motors. In the embodiment, wherein the tactile array includes rotary motors, the rotary motors include a transmission component that converts torque produced by the rotary motors into linear force that is applied to the second cutaneous surface. In one such embodiment, the transmission component includes at least one member selected from the group consisting of: a lever arm; a rack and pinion; and a ball screw. In one specific embodiment, the transmission component further includes at least one Bowden cable.

In another embodiment, the tactile array includes at least one member of the group consisting of a pneumatic component and a hydraulic component. Further, an embodiment of the method of the invention includes the step of implanting a sensing component associated with the first cutaneous surface, whereby afferent feedback generated by the tactile array is monitored. In one such embodiment, the sensing component includes a deformation-sensitive array at the first cutaneous surface. In a specific embodiment, the deformation-sensitive array is a magnetic deformation-sensitive array. Alternatively, or additionally, the deformation-sensitive array is an ultrasound array. In still another embodiment, the sensing component includes a nerve cuff placed at an innervating cutaneous nerve associated with the first cutaneous surface of the subject.

In another embodiment, the invention is a method for providing proprioceptive feedback to a subject. In this embodiment, the method includes the steps of implanting at least one magnetic target at a pair of muscles in agonist-antagonist relation to each other. A signal representing an applied force to the subject, or to a bionic component of the subject, is detected, and a selective electromagnetic field consequent to the detected force is generated, thereby causing the magnetic target to apply a force to the pair of muscles in agonist-antagonist relation to each other, whereby an afferent signal is generated by the agonist-antagonist muscle pair, thereby providing proprioceptive feedback to the subject.

In one such embodiment, the selected magnetic field is applied by a plurality of electromagnetic coils. In a specific embodiment, the method further includes the step of fixing the electromagnetic coils to a surface of the subject proximate to the at least one magnetic target. The method can further include the step of affixing a plurality of sensing magnetometers to the subject proximate to the at least one magnetic target, whereby a change in position of the at least one magnetic target caused by an efferent signal generated by the subject is detected, thereby sensing changes in the muscle lengths of the agonist-antagonist muscle pairs. The at least one magnetic target can be, for example, a permanent magnet or an electromagnet.

In still another embodiment of a method for providing proprioceptive feedback in a subject of the invention, targets are implanted at the pair of muscles wherein the muscles are in an agonist-antagonist relation to each other. At least one state of the targets is detected, thereby detecting a physical property of the agonist-antagonist pair of muscles. An afferent signal is generated consequent to the state of the agonist-antagonist pair of muscles, thereby providing proprioceptive feedback to the subject. In at least one such embodiment, at least one passive target includes at least one member of the group consisting of a permanent magnetic material and an electromagnetic material.

In another embodiment the invention is a method for selectively stimulating at least a portion of axons or nerve fascicles of a neuron of a subject comprising the steps of placing a cuff at or proximate to a neuron of a subject, the cuff including one or more antennas at or proximate to the cuff and collectively extending about at least a portion of a circumference of the neuron, thereby forming an array of the antennas about the neuron. In one embodiment, the array is a fixed array, wherein the antennas are fixed in position relative to each other. Electromagnetic waves are selectively generated at the one or more antennas and focused at a subset of at least one member of the group consisting of axons and nerve fascicles of the neuron, thereby causing depolarization of the subset and consequent selective stimulation of at least a portion of the axons or nerve fascicles of the neuron of a subject.

In one embodiment, the electromagnetic wave generated by the one or more antennas includes a carrier component and a signal component, wherein the carrier component has a lower frequency than the signal component. The electromagnetic waves, in one embodiment, are focused by at least one member of the group consisting of reflection and phase shifting of the electromagnetic waves. In the embodiment wherein the electromagnetic waves are focused by reflection, they can be reflected off a parabolic reflector, for example. In another embodiment, the electromagnetic waves are generated at the one or more antennas by a radiofrequency generator, and the electromagnetic waves are focused by a controller. In yet another embodiment, the method includes amplifying electromagnetic waves by a radiofrequency amplifier. In still another embodiment, the method further includes the step of boosting signal strength from the radiofrequency generator by a radiofrequency repeater.

In another version of this embodiment of the invention, the cuff is a nerve cuff that is implanted at the neuron. For example, the nerve cuff can extend about an epineurium of the neuron. In a specific embodiment, the array is a linear array and is sutured tangent to the epineurium.

In yet another version of this embodiment of the method of the invention, the electromagnetic magnetic waves are in a gigahertz range. In still another embodiment, the array of antennas includes at least one member of the group consisting of stainless steel, silver, gold, poly (3,4,-ethlenedioxythiophene), aluminum, copper, tungsten, and zinc. In a specific embodiment, the array of antennas are coated with a biocompatible material, such as a biocompatible polymer. Another example of a biocompatible material is silicone.

In yet another embodiment of this method of the invention, the cuff is fixed to a surface of the subject. The cuff can be either rigid or flexible. Where the cuff is flexible, the method further includes the steps of identifying the position of the one or more antennas of the fixed array relative to the neuron by at least one member of the group consisting of a position sensor and an angle sensor. In this embodiment, at least one of a position sensor and an angle sensor can include at least one member of the group consisting of the potentiometer, an encoder, and a flex sensor. In yet another embodiment, the method further includes the steps of measuring a time delay among pulses of the one or more antennas of the fixed array relative to each other, and calculating a geometry that causes the fixed antenna array to identify a position of the antennas of the array relative to each other and relative to the neuron. In still another embodiment, the antennas of the array are affixed to a skin patch, which is then attached to the skin of the subject, and the method further includes the step of calibrating each antenna by identifying the position of each of the antennas of the fixed array relative to each other and to the neuron contemporaneously with muscle flexion of the subject. In a specific embodiment, the antennas are embedded in a skin patch, and in another embodiment, the method further includes the step of attaching the skin patch on the subject.

Another embodiment of the invention is a method for tracking one or more objects, and includes applying one or more targets to each of the one or more objects and positioning an array of sensors proximate to the at least one target, whereby a signal from the at least one target at the sensors is detected. The parameters describing the state of each of the one or more targets are then estimated and predicted values of the signal at each of the sensors are calculated given these estimates of the parameters, whereby a prediction error in the predicted values of the signal with reference to the values of the signals detected at the sensors is computed. A prediction error Jacobian matrix is then calculated by analytically computing elements of the prediction error Jacobian matrix, and the prediction error in combination with the prediction error Jacobian matrix are used to determine a state of the at least one target, whereby the state is indicative of a physical state of the at least one object. In one embodiment, the signal is a magnetic field. In another embodiment, the magnetic field prediction error Jacobian matrix is calculated by analytically computing submatrices of the magnetic field prediction error Jacobian matrix and assembling the analytically-computed submatrices into a single matrix. In yet another embodiment, the sensors are magnetometers. In another embodiment, the submatrices of the error Jacobian are computed in a cascading calculation. In yet another embodiment, the prediction errors are also computed in a cascading calculation. In another embodiment, the object is a tissue of a subject, the change in physical state of the object is indicative of a change in a physiological feature of a subject, and a physiological feature of the subject is modified that affects and or is affected by the changes to the subject, the modification being responsive to the change in state of the subject, thereby modulating the physiological feature of the subject.

In one such embodiment, submatrices are calculated simultaneously and before being assembled into the single matrix. In another embodiment, at least one passive target includes a magnet, and the sensors include magnetometers. Examples of suitable magnets include permanent magnets and electromagnets. In yet another embodiment, the method further includes the step of tracking an ambient magnetic field, whereby the ambient magnetic field is tracked as a time-varying magnetic disturbance, thereby causing interference to be removed from the signal from the at least one target. In another embodiment, the at least one passive target is a permanent magnet, and the array of sensors is an array of magnetometers.

A specific version of one embodiment of this method includes a method for detecting a state (e.g., a change in state) of one or more objects while compensating for a disturbance field that includes applying one or more targets to each of the one or more objects and positioning an array of sensors proximate to the at least one target, whereby a signal from the at least one target at the sensors is detected. The parameters describing the state of each of the one or more targets are then estimated, and the parameters of the disturbance field are also estimated, and predicted values of the signal at each of the sensors are calculated given these estimates of the parameters, whereby a prediction error in the predicted values of the signal with reference to the values of the signals detected at the sensors is computed. A prediction error Jacobian matrix is then calculated, and the prediction error in combination with the prediction error Jacobian matrix are used to determine a state of the at least one target, whereby the state is indicative of a physical state of the at least one object.

In one embodiment of this method, the position of each target is fixed relative to a global coordinate system, whereby a change in position of the array of sensors relative to the passive target is determined. In another embodiment, the at least one target is a permanent magnet, such as a spherical, cylindrical, or cubical permanent magnet.

A method for detecting a state of one or more objects includes the steps of: providing one or more targets at each of the one or more objects; positioning an array of sensors proximate to the one or more targets, whereby a signal from the targets at the sensors is detected; estimating parameters describing the state of each of the one or more targets; calculating, in a cascading calculation, predicted values of the signal at each of the sensors given the estimates of the parameters; computing a prediction error in the predicted values of the signal with reference to the values of the signals detected at the sensors; calculating a prediction error Jacobian matrix; and determining from the prediction error and the prediction error Jacobian matrix a state of the one or more targets, whereby the state is indicative of a physical state of the one or more objects.

In an embodiment, a method for determining one or more of three sensor positions and three sensor orientations for each of the sensors in a sensor array includes the steps of: placing at least one target in at least one known location relative to a sensor array, whereby a signal from the at least one target at the sensors is detected, and recording at least one measurement of the signal at each of the sensors for each placement of the one or more targets; estimating one or more parameters from the group consisting of x-position, y-position, z-position, yaw, pitch, and roll, of each of the sensors; estimating any unknown state parameters of the at least one target; calculating predicted values of the signal at each of the sensors for each of the measurements given the estimates of the sensor parameters and target states; computing a prediction error in the predicted values of the signal with reference to the values of the signals detected at the sensors; calculating a prediction error Jacobian matrix by analytically computing elements of the prediction error Jacobian matrix with respect to the estimated parameters of the sensors for each measurement; and determining from the prediction error and the prediction error Jacobian matrix a state of the parameters of the sensors.

The method can further include the steps of implanting at least one magnet at each of at least one respective tissue of a subject; applying the array of magnetometers to the subject proximate to the at least one magnet, whereby a position of the magnet relative to the array of magnetometers is determined, the position being indicative of a physical property of the tissue of the subject; and modifying a physiological feature of the subject that affects or is affected by the physical property of the tissue of the subject, thereby modulating the physiological feature of the subject.

The method can further include the steps of: rotating the array of magnetometers about each of three coordinate axes in a uniform magnetic field while collecting a three-axis data stream from each of the magnetometers; calibrating each of the magnetometers in the array by determining hard iron offsets and soft iron distortions; scaling gains of the magnetometers with respect to one another; and determining rotation matrices that map the three-axis data streams from the magnetometers into a common coordinate system, whereby relative sensor orientations are determined.

In another embodiment, the invention is a method for determining one or more of each of three sensor positions and three sensor orientations for each of the sensors in a magnetometer array that includes the steps of: placing a magnet in at least one known location and taking at least one sample of the magnetic field at each of the sensors with the magnet at the at least one known location; calculating for at least one time step, and for each magnetometer, an analytic derivative of the magnetic field with respect to at least one of the three axes of magnetometer estimated location and three axes of magnetometer estimated rotation for each sensor and the estimated magnetic dipole strength and estimated dipole orientation; assembling the analytic derivatives corresponding to the magnetometers and each time step into a Jacobian matrix; employing a Levenberg-Marquardt algorithm to adjust the estimation of the dipole strength and orientation of the magnet at each timestep and each magnetometer position and angle to thereby determine improved estimates of the strength and orientation of the magnet and of the positions and orientations of the magnetometers; comparing the measured magnetic field at each sensor over all timesteps to the calculated magnetic field at each sensor over all timesteps, given the estimates of position and orientation of each of the sensors and, to determine if the Levenberg-Marquardt algorithm has converged; repeating the calculation of the analytic derivatives, assembly of the analytic derivatives, and adjustment of the calculation of the dipole strength of the magnet and each magnetometer estimated position and orientation by the Levenberg-Marquardt algorithm as necessary until the algorithm converges; and updating the estimate of the magnetic dipole and magnetometer positions and orientations upon convergence of the Levenberg-Marquardt algorithm.

In one version of this embodiment, at least one magnet is implanted at each of at least one respective portion of a subject. The array of magnetometers is then applied to the subject proximal to the at least one magnet, whereby a change in position of the magnet relative to the array of magnetometers is determined, the change in position being indicative of a change in physical state of the subject, and a physical feature of the subject is modified that affects or is affected by the change of state of the subject, thereby modulating the physical feature of the subject.

In yet another version of this embodiment, the dipole orientation of the magnet is fixed relative to the array of magnetometers by exposing the magnet to at least one of a second magnet and to an electromagnetic coil that is placed in a fixed location relative to the magnet. In another version of this embodiment, the strength of the dipole of the magnet is determined for at least one time step, by placing the magnet in a fixed position in dipole orientation relative to the magnetometer array; sampling the magnetic field at each magnetometer in the magnetometer array; and calculating the magnetic field at each magnetometer given the estimates of magnetometer position and the estimated magnetic dipole strength, thereby measuring a strength of the dipole magnet.

In yet another version of this embodiment, the estimate of the dipole strength of the magnet is calculated from at least one member of the group consisting of: a volume of the magnet; magnetization of the magnet; an N-rating of the magnet; and a residual flux density of the magnet. In still another version of embodiment, the initial estimate of the dipole strength of the magnet is a random value. In another version, the dipole strength of the magnet and the position and orientation of the magnetometers of the array are determined simultaneously by a prediction error Jacobian of the magnetic dipole strength. In one embodiment, a plurality of samples is taken of the magnetic fields at distinct positions of the magnetometers relative to magnets having known orientations. In another version, plural magnet positions are sensed by moving the magnet over the array of magnetometers. In yet another version, plural magnet positions are sensed by placing the magnet over several known positions relative to the array of magnetometers.

In still another version of this embodiment, biases of magnetometers and any offset angles are determined prior to tracking of the at least one permanent magnet and prior to position calibration of the magnetometer dipole strength measurement of the at least one permanent magnet. For example, the method can include further steps, including: recording data from each magnetometer of a magnetometer array that is rotated separately in each of three axes; subtracting, for each axis of rotation, a midrange of data of each magnetometer from the recorded axis data of the magnetometer to generate offset-adjusted data; storing the midrange of data of each magnetometer; calculating the time-varying mean of each axis across the magnetometers; calculating the mean absolute error between the time-varying mean and magnetometer data; storing the mean absolute error as a metric of goodness of offset calibration; optimizing fit matrices, thereby minimizing squared differences between inputs to each magnetometer; storing the optimized fit matrices for each of the magnetometers; and multiplying the stored matrices by subsequent three axis data streams and the mean absolute error across the stored optimized matrices to thereby form a metric of goodness of fit of angle offsets.

In one such embodiment, the fit matrices are strict rotation matrices. In another embodiment, the fit matrices are transformation matrices. In still another embodiment, the method of the invention further includes optimizing the fit matrices, whereby the error between the transformed data and that mean three-axis field across the magnetometers of the rate is minimized when the fit matrices are multiplied by the data from the data streams of each of the three axes.

A device for detecting a physical property of tissue includes an array of sensors to detect a plurality of targets at a tissue, and electronics to determine at least one state of the targets relative to each other and provide an indication of a physical property of the tissue.

Embodiment 1: Method of Employing Passive Implants to Determine a Physical Feature of a Subject A first embodiment of the invention is a method for determining a physiological feature of a subject, and is described below with reference to FIGS. 1-4.

1.1 Muscle-Tendon Sensing Using Magnetometers with Implanted Permanent Magnets

Figure 1B:
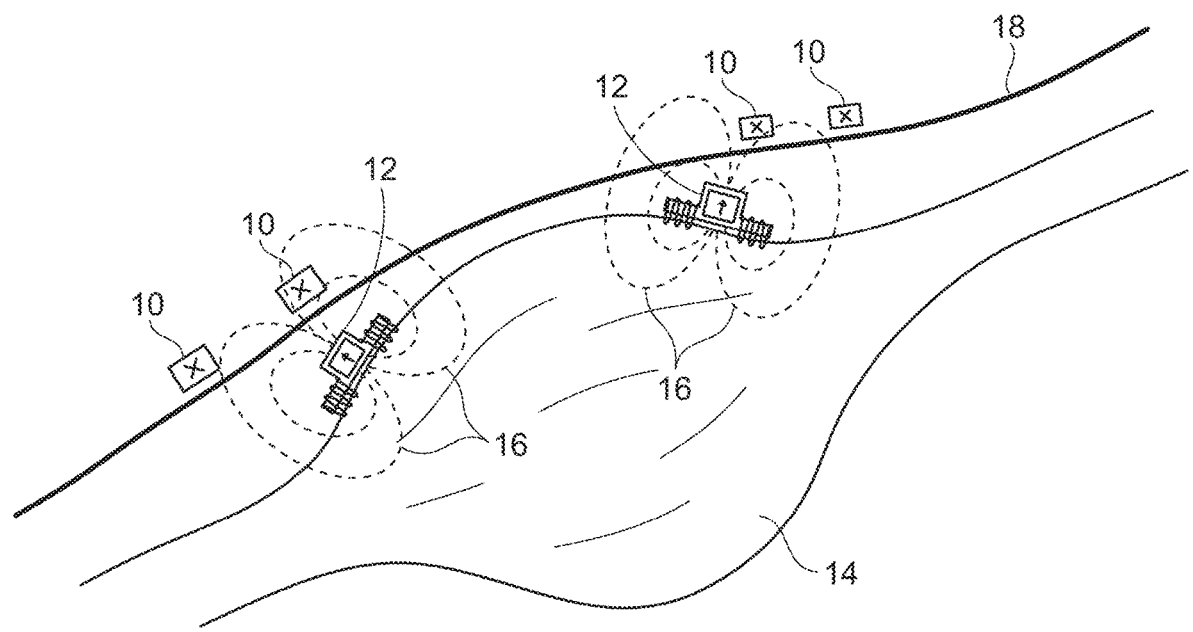
FIG. 1B is a schematic representation of the magnetic fields shown in FIG. 1A during muscle contraction that causes translation and rotation of the magnetic field during the same embodiment of the method of the invention.
Figure 2:
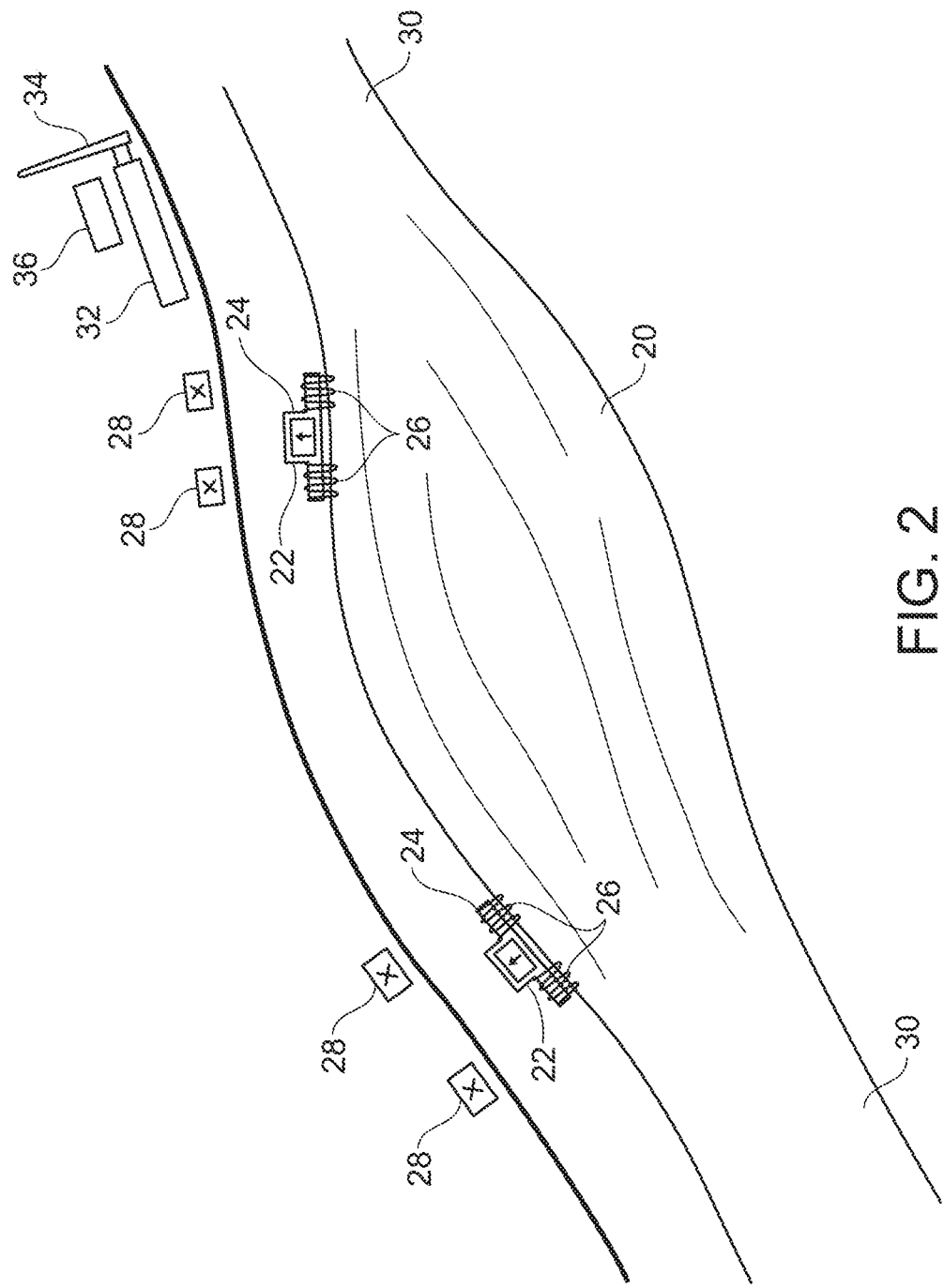
FIG. 2 is a schematic representation of an alternative arrangement of permanent magnets in a muscle according to another embodiment of the method of the invention.

FIG. 1A and FIG. 1B are schematic representations of the first version of the first invention. As can be seen in FIGS. 1A and 1B, the apparatus includes a plurality of externally mounted magnetometers 10 positioned in a configuration that senses magnetic field alterations from a plurality of implanted targets, here permanent magnets 12. In this embodiment, the plurality of implanted permanent magnets 12 are configured within or on muscle 14 to sense muscle state from the plurality of externally mounted magnetometers 10. Relative position and movement of the implanted permanent magnets 12 are detected by magnetometers 10, which are sensitive to changes in local magnetic field. Because permanent magnets 12 are fixed to muscle 14, changes in muscle state cause local magnetic field 16 to shift and rotate. FIG. 1A shows magnetic fields 16 from implanted permanent magnets 12 on muscle 14 at rest (the arrow within the permanent magnets represents the magnetization direction). As shown in FIG. 1B, muscle contraction causes translation and rotation of magnetic fields 16. These changes in magnetic field 16 are sensed by each of magnetometers 10 in one or a plurality of dimensions; the distance between each implanted permanent magnet 12 and every other permanent magnet is then determined in real-time, providing a measurement of muscle state.

A magnetometer is any device that can sense the magnitude and/or direction of magnetic fields, or changes in the magnitude and/or direction of magnetic fields. Several known types of magnetometers are suitable for use in the method of this invention. For example, Hall Effect sensors measure a transverse voltage caused by the deflection of flowing electrons in a magnetic field. Alternatively, passive electromagnetic coils rely on Faraday's law to detect changes in magnetic field using the Lorentz force on electrons. A non-exhaustive list of other suitable magnetometers includes magnetoresistors, magneto-inductive sensors, fluxgate magnetometers, and superconducting quantum interference device (SQUID) magnetometers.

Specific examples of Hall effect sensors that are suitable for use by the method of this invention include, but are not limited to, Texas Instruments DRV5053EAQLPG, DRV5053OAQLPG or DRV5053VAQLPG. An integrated circuit, such as a STMicroelectronics LSM303DLHC-ND inertial measurement unit, that couples magnetic field sensors with other sensor types, is suitable for use with or without powering all available sensors on the chip. Magnetoresistors (such as the Honeywell HMC1001-RC, HMC1002-TR, HMC1021Z-RC, HMC1051ZL, or HMC2021S-TR), magneto-inductive sensors (such as the RM3100 or RM2100 geomagnetic sensor package from PNI Sensor Corporation, previously known as the SEN-L, SEN-XY, and SEN-Z magnetic field sensors) and fluxgate magnetometers are also suitable for employment to perform the magnetic field sensing in the method of the invention. Additionally, other digital magnetometers such as the MAG3110 from NXP Semiconductors N.V. or the STMicroelectronics LIS3MDL are suitable for employment in the method of this embodiment of the invention. Electromagnetic coils can be formed that employ spiraled or coiled conductive wire or spiraled or coiled circuit board traces, and can be used to detect temporal changes in magnetic field. The magnetometers in this invention can be fixed to the surface of skin 18 by employing an adhesive (skin patch) or an elastic band, or by construction into clothing, shoes, a prosthetic socket, an orthosis or an exoskeletal interface.

Multiple arrays of magnetometers can be used simultaneously to track sets of magnetic targets. For instance, multiple sensor arrays may be attached to a single prosthetic socket, a single orthosis or a single exoskeletal interface, wherein each sensor array is adjacent to a different tissue, and wherein each tissue has multiple targets.

The efficacy of the method can be further improved by shielding the magnetometer and permanent magnet system with a high-permeability material, such as permalloy or Mu-metal. A single layer or multiple layers of high-permeability material can be employed to fully or partially surround the system of magnetometers and permanent-magnets.

A permanent magnet is a metal that has been magnetized sufficiently that it retains its own persistent magnetic field. Some examples of permanent magnet types that may be used for this invention include sintered or bonded neodymium iron boron (NdFeB), samarium cobalt (SmCo), AlNiCo, ceramic, injection molded (nylon or polyphenylene-sulfide), and flexible, or ferrite magnets.

To increase biocompatibility, in one embodiment, implanted permanent magnets are coated with a bioceramic, parylene, glass, silicone (such as NuSil™ Medical Grade silicone), titanium, tantalum, biocompatible polyurethane, or some other biocompatible polymer (e.g. polydimethylsiloxane, or PDMS) for biological compatibility. Examples of biocompatible polyurethanes include Bionate® Thermoplastic Polycarbonate-urethane PCU, Bionate® II PCU, BioSpan® Segmented Polyurethane (SPU), CarboSil® Thermoplastic Silicone-Polycarbonate-urethane (TSPCU), Elasthane™ Thermoplastic Polyether-urethane (TPU), PurSil® Thermoplastic Silicone-Polyether-urethane (TSPU) or any other coating manufactured by DSM Biomedical.

To fix the implanted permanent magnets to a consistent location within the tissue and prevent potential micromotion or migration, in one embodiment, the implanted magnets are coated with a profibrotic material prior to surgical implantation. In yet another embodiment, fibrin glue is used during implantation so that the permanent magnet will be secured into place during fibrosis and granulation. In yet another embodiment, the biomcompatible material is modified to have a surface roughness sufficient to promote adherence by the tissue. Profibrotic materials, fibrin glue, and similar biomaterials are common in pacemakers and cardiac implants for fixing an implant to a tissue.

In another embodiment, implanted permanent magnets are mounted to a surface of muscle 20 (see FIG. 2) or within the muscle belly. To facilitate anchoring to or within the muscle 20, specialized features can be incorporated into permanent magnets 22 or biocompatible coating 24. Examples of such features include wings containing holes, loops for suture 26, geometries to prevent rotation of the magnet within the muscle, and geometries or materials that improve integration with biological tissues. Implanted permanent magnets 22 can be placed by a suitable technique, such as is known in the art, including, for example, during an open surgical operation. Alternatively, they can be injected into the muscle using a magnet-safe hypodermic needle.

Multiple implants can be employed to determine muscle state when, for example, a muscle moves without muscle contraction taking place. For instance, pressure from an external source through a skin surface (such as by a lower extremity prosthetic socket) can cause external deformation of the muscle. If only a single implant is employed, the implant will be deflected in this circumstance and a false representation of the muscle state will be given by the single implant location. Another example in which a single implant will not provide an accurate measure of muscle state is when the skin moves relative to the implanted muscle. In this situation, the distance from the implant to a point on the skin surface would change, but this change is not the result of muscle contraction. With two or more implants at the muscle, the distance between the implants can be determined regardless of muscle deformation or skin movements, and this information can then be employed to robustly determine muscle state.

In one embodiment, to increase the resilience of the distance measurement to perturbation of the muscle, at least a three-axis magnetometer or a two-axis magnetometer or two single-axis magnetometers are employed to determine the positions of each of the magnets along at least one shared dimension. Additional magnetic field sensors allow for the detecting of the positions of each of the magnets along more than one shared dimension and makes the detection of the state of the targets relative to one another resilient to perturbations of the targets in more than one shared dimension and also simplifies the process of calibration. For example, if using two cylindrical permanent magnets of known magnetic dipole strength magnetized through the thickness of the permanent magnets, each of the permanent magnets has five degrees of freedom. In this situation, ten independent magnetic field sensors can be employed to determine the exact position and orientation of both of the permanent magnets (this can be accomplished employing, for example, ten single-axis magnetometers or four three-axis magnetometers). This allows the distance between the permanent magnets to be determined regardless of the position of the sensors relative to the permanent magnets, provided that they are within the range of sensing. Additional sensors beyond this number can be employed to increase permanent-magnet tracking accuracy by compensating for sensor noise and by taking into account any magnetic disturbances, such as from the magnetic field of the earth, which accounts for a fraction of the magnetic field sensed by the magnetometers.

The plurality of permanent magnets 22 and magnetometers 28 can be expanded to a large number of magnet-magnetometer groups. A web of permanent magnets across the entirety of muscle 20 measures local muscle strains and displacements across a complex surface of the muscle and increases the accuracy of muscle state estimation.

A plurality of permanent magnets can also be fixed directly to or anchored within one or more tendons 30. By employing the methods described above, tendon strain can then be determined via external magnetometers 28. A simple model of tendon force-length relationships can be employed to directly estimate force in the tendon.

A clinical imaging modality, such as ultrasound, provides an indication of relative implant locations to thereby calibrate magnetometer readings against in vivo distance measurements within the muscle during rest, stretch, and flexion.

Sensor readings from the magnetometers 28 are fed into computer 32, which is employed to process sensor readings and/or perform muscle state calculations. Sensor readings and/or muscle state information are then delivered to another device (such as a bionic joint controller) via a data transfer antenna 34 or via wired transmission line, where the data is further processed and/or employed for feedback and/or control. The computer and sensors are, in one embodiment, powered by an external power supply or by portable battery 36.

Alternatively, in addition to the musculotendinous applications described above, permanent magnets 22 can be implanted in other tissues within the body. A non-exhaustive list of potential applications includes state sensing in cardiac and smooth muscle; bone bending, stretching, and compression; lung inflation and deflation; digestive system propulsion (peristalsis); vasoconstriction and vasodilation; skin stress and strain; and size and position monitoring generally of bodily organs, such as the liver, pancreas, kidneys, bladder, teeth, tongue, and reproductive organs.

Figure 3:
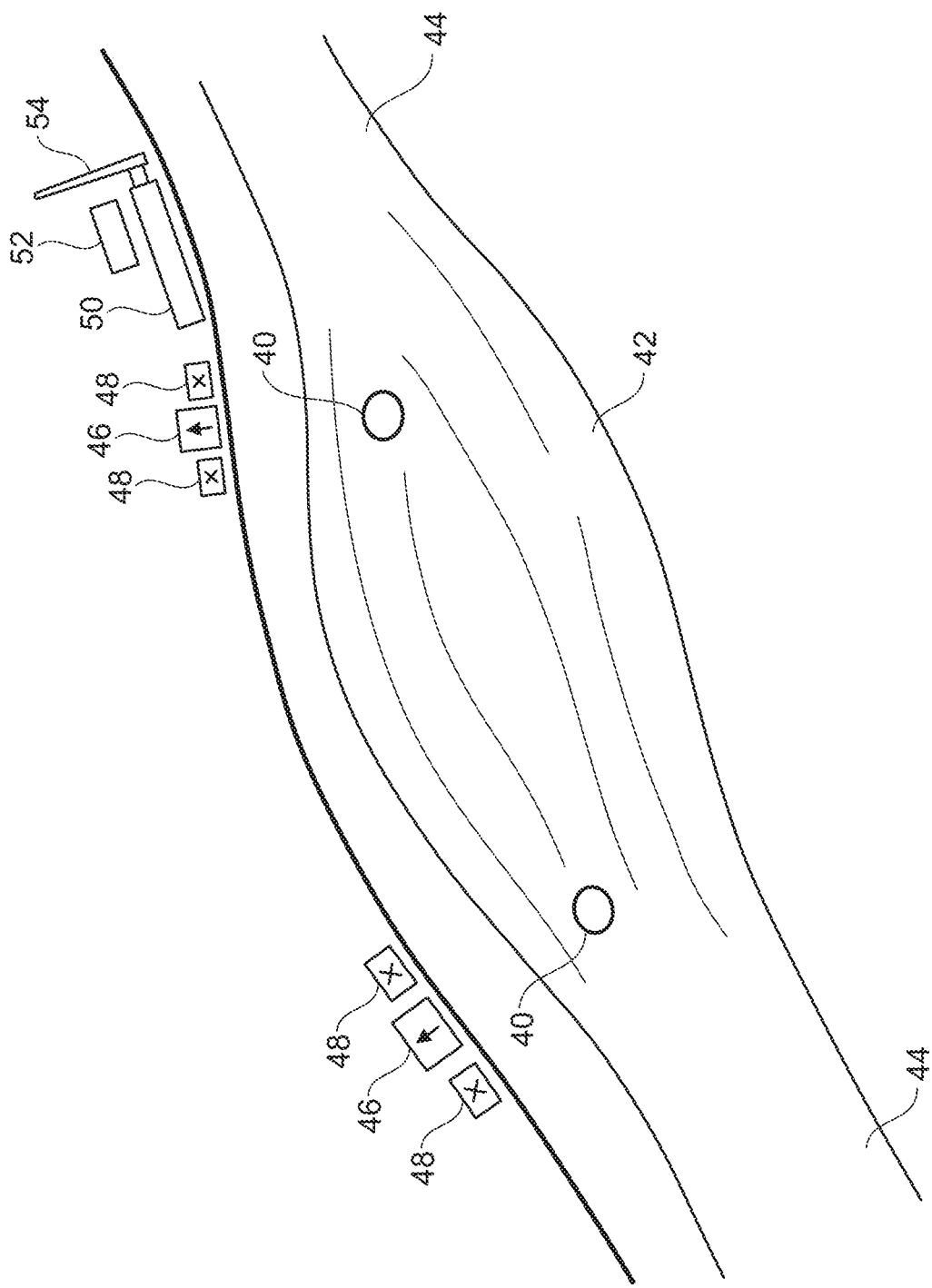
FIG. 3 is a schematic representation of an arrangement of permanent magnets and a plurality of ferromagnetic materials at a muscle according to still another embodiment of the method of the invention.

1.2 Muscle-Tendon Sensing Using Magnetometers and Ferromagnetic Materials Coupled with an External Magnetic Field A second version of this first embodiment of the method of the invention is identical to the first, except that a plurality of pieces of ferromagnetic material 40—instead of permanent magnets—are implanted on or within muscle 42 or tendon 44, as shown in FIG. 3. An example of one such ferromagnetic material is ferritic stainless steel. As in the first embodiment, ferromagnetic materials can be coated to increase biocompatibility. Because unmagnetized ferromagnetic materials do not create an electromagnetic effect in the absence of an existing magnetic field, this embodiment depends on an existing magnetic field whose source is external to the body. This magnetic field can be created by permanent magnets 46, electromagnetic coils, or the earth's magnetic field. FIG. 3 shows one implementation of this embodiment where the magnetic field is created by permanent magnets 46 mounted external to the body. This embodiment of the method of the invention also employs computer 50, portable battery pack 52, and antenna 54. The function of this version of the first embodiment is similar to that of the first version; when muscle 42 changes length, magnetic field strength and orientation as seen by magnetometers 48 are altered by the change in position of the implanted ferromagnetic materials when the muscle tissue contracts or is stretched.

As with the first embodiment, ferromagnetic materials 40 may also, or alternatively, be implanted in other tissues within the body. A non-exhaustive list of potential applications includes sensing in cardiac and smooth muscle; bone bending, stretching, and compression; lung inflation and deflation; digestive system propulsion (peristalsis); vasoconstriction and vasodilation; skin stress and strain; and size and position monitoring generally of bodily organs, such as the liver, pancreas, kidneys, bladder, teeth, tongue, and reproductive organs.

1.3 Muscle-Tendon Sensing Using Inductive Sensing

In a third version of this first embodiment of this invention, a plurality of ferromagnetic or electrically conductive implants is fixed to or within one or more muscles or one or more tendons. A plurality of electromagnetic coils is then positioned external to the body. Implant location can be estimated from the inductance of the electromagnetic coils (a variable inductance sensor) or from the inductive coupling between electromagnetic coil pairs (a variable differential transformer). This inductance measurement can be used to determine the distance to the implants. Employing the calculations described in Embodiment 1.1, tissue state can then be determined from those distances.

In one configuration of a variable inductance sensor, inductance is inferred from a measurement of electric current through an electromagnetic coil as it is driven with a varying voltage signal.

In another configuration of a variable inductance sensor, inductance-to-digital converters are used for measuring the impedance and/or resonant frequency of the electromagnetic coils as part of LC resonators. By placing the electromagnetic coils in parallel with capacitive elements, circuits are created whose resonant frequency and impedance are altered by the movement of nearby ferromagnetic or electrically conductive materials. The measured impedances and/or resonant frequencies can then be employed to determine the location of the implants. Examples of suitable inductance-to-digital converters that can be employed in this embodiment include the Texas Instruments LDC1000, LDC1000-Q1, LDC1101, LDC1612, LDC 1614, LDC1041, and LDC1051 inductance-to-digital converters.

In a variable differential transformer configuration, inductive coupling is sensed as one electromagnetic coil in each of the coil pairs is driven with a voltage, while the voltage is monitored on the corresponding coil in each electromagnetic coil pair. The presence of a ferromagnetic or electrically-conductive implant modifies the inductive coupling between the electromagnetic coils. This occurs by modifying the lowest permeability path when the implant is placed in a position relative to the coils or by increasing the impedance between the coil pairs via eddy currents and hysteresis in the target.

1.4 Muscle-Tendon Sensing Using Echo-Based Ultrasound Transducers and High or Low Density Material Implants In a fourth version of the first embodiment of the invention, the method of this invention employs a plurality of sound emitting devices, such as ultrasound transducers, which are coupled with implants of a density that is significantly different from human tissue for real-time sensing of tissue state and force.

Figure 4:
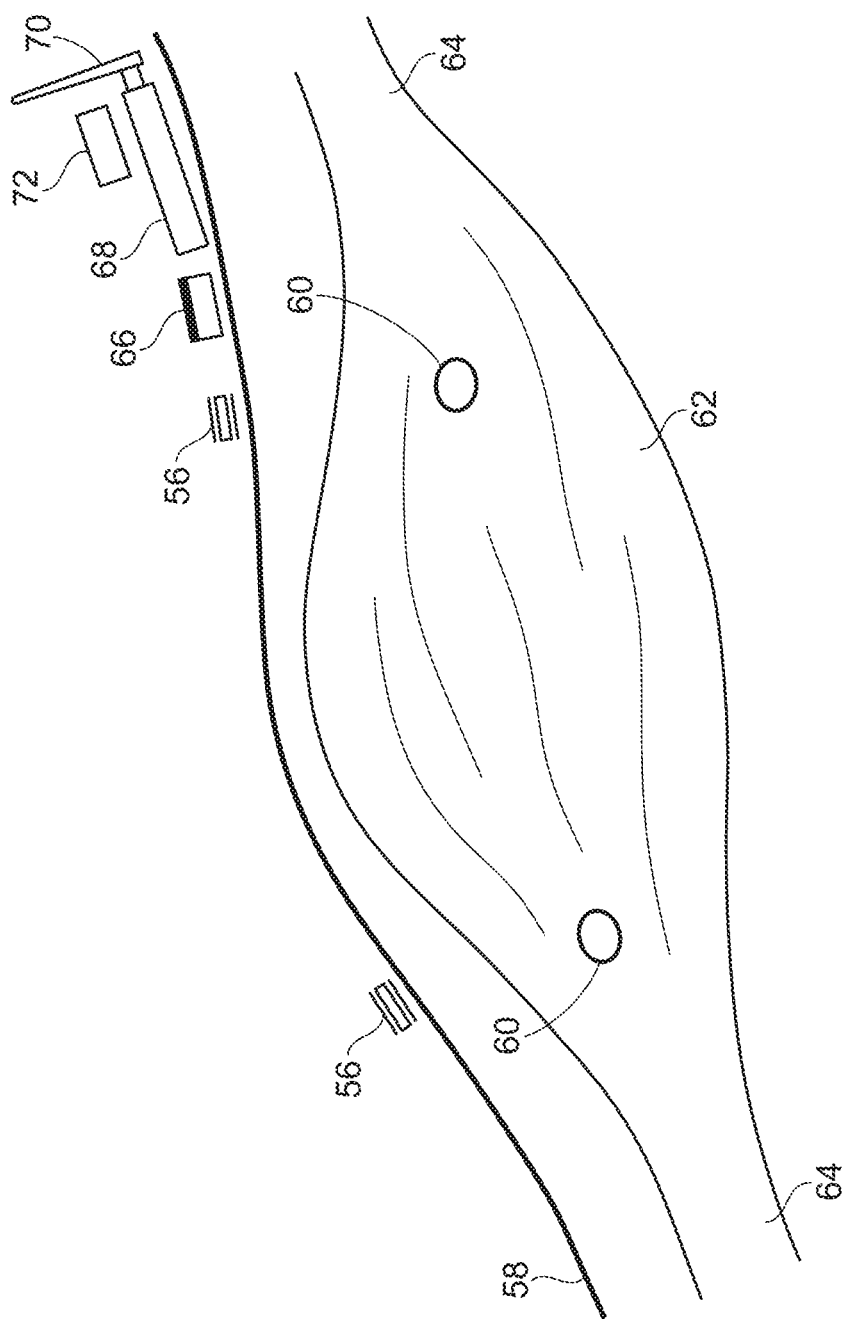
FIG. 4 is a schematic representation of yet another embodiment of the method of the invention, wherein transducer groups are located on skin of a subject.

One embodiment of this version employs a single or plurality of grouped neighboring ultrasound transducers 56 mounted on the surface of skin 58, and a plurality of implanted materials 60 within muscle 62 or tendon 64, adjacent to the location of transducers 56 groups on skin 58 (see FIG. 4). Ultrasound transducers 56 emit an acoustic signal into muscle 62 or tendon 64 and monitor the reflection latency (time of flight) of the echo from implanted material. The reflection latency can be used to calculate the distance between each transducer 56 and implanted materials 60. Because the distance between neighboring transducers is known, precise implant locations relative to each transducer (emitter) 56 can be triangulated from these distance measurements. In this way, the distance between each implanted material and every other implanted material can be determined in real-time, providing a measurement of muscle state. Alternatively, a plurality of implanted materials is on or inside tendon 64 to measure tendon elongation in order to estimate muscle-tendon force.

Implanted materials 60 of necessity have a density different from the surrounding tissue, because it is the boundary between materials of differing density that causes the acoustic reflections measured by the ultrasound transducers. This material may be either solid or hollow. Examples of potential high-density materials include titanium or stainless steel. Low-density materials (relative to human tissue) may also be used.

Examples of suitable ultrasound transducers include those known in the art, such as the Sonometrics Piezo-Electric Crystals (0.7 mm, 1 mm, or 2 mm), Olympus C548-SM Angle Beam Transducer, Olympus Dual Element Transducers (such as the MTD705, U8452060, U8452058, and/or U8452059), Mana Instruments Dual Element Transducers (such as the D5006 or D7506), Electromatic T-101-2000 and T-101-3000 Dual Element Transducers, Blatek Contact Transducers or Blatek Piezo-Composite Crystals, or the Dakota Ultrasonics Single Element Contact Transducers (such as the T-5903-2857, T-4903-2875, T-5903-4875, and/or T-4903-4875 transducers).

In one embodiment, to increase biocompatibility, implanted materials are coated in a bioceramic, parylene, glass, silicone (such as NuSil™ Medical Grade silicone), titanium, biocompatible polyurethane, or some other biocompatible polymer (e.g. polydimethylsiloxane, or PDMS) for biological compatibility. Examples of biocompatible polyurethanes include Bionate® Thermoplastic Polycarbonate-urethane PCU, Bionate® II PCU, BioSpan® Segmented Polyurethane (SPU), CarboSil® Thermoplastic Silicone-Polycarbonate-urethane (TSPCU), Elasthane™ Thermoplastic Polyether-urethane (TPU), PurSil® Thermoplastic Silicone-Polyether-urethane (TSPU) or any other coating manufactured by DSM Biomedical.

In this embodiment, implanted materials 60 can be mounted to the surface of muscle 62 or within the muscle belly to measure muscle state, or mounted to the surface of tendon 64 or within the tendon to measure muscle-tendon force. To facilitate anchoring to or within the muscle or tendon tissues, specialized features can be incorporated into implanted material 60 or its coating. Examples of such features include wings containing holes, suture loops, geometries to prevent rotation of the magnet within the muscle, and geometries or materials that improve integration with biological tissues. The implanted materials can be placed during an open surgical operation. They can also be injected into the muscle using a hypodermic needle.

Transducers 56 and implanted materials 60 can be expanded to a large number of groups. A web of implanted materials across the entirety of muscle 62 allow measurement of local muscle strains and displacements across the complex surface of the muscle and increases the accuracy of muscle state estimation.

In another embodiment, a plurality of implanted materials 60 is fixed directly to or anchored within one or more tendons 64. Employing the methods described above, tendon strain can then be determined via external ultrasound transducers. A simple model of tendon force-length relationships can be employed to directly estimate force in the tendon.

In one version of this embodiment, a clinical imaging modality such as ultrasound can provide an indication of relative implant locations within the muscle during rest, stretch, and flexion to calibrate ultrasound transducer readings against in vivo distance measurements.

Ultrasound transducers 56 are driven by oscillation and sensing circuitry 66 which is driven by computer 68. The oscillation and sensing circuitry then deliver the sensor readings to computer 68, which is employed to process sensor readings and/or to perform muscle state calculations. Sensor readings and/or muscle state information is then delivered to another device (such as a bionic joint controller) via data transfer antenna 70 or via a wired transmission line, where the data is further processed and/or employed for feedback and/or control. The computer and sensors may be powered by an external power supply or by portable battery 72.

As with all other embodiments, the implanted materials can, alternatively or additionally, be placed in other tissues within the body. A non-exhaustive list of potential applications includes state sensing in cardiac and smooth muscle; bone bending, stretching, and compression; lung inflation and deflation; digestive system propulsion (peristalsis); vasoconstriction and vasodilation; skin stress and strain; and size and position monitoring generally of bodily organs, such as the liver, pancreas, kidneys, bladder, teeth, tongue, and reproductive organs.

1.5 Application for Inventions Using Implanted Sensors

In each of the versions of this embodiment of the method of the invention, a powered sensor portion (i.e. magnetometer, ultrasound transducer, etc.) can be implanted within the body instead of external to the body. In these versions, the magnetometers and ultrasound transducers are implanted within the skin and either employ transcutaneous wireless power and data transfer or operate in conjunction with a percutaneous wired power and data connection.

Embodiment 2: Method of Providing Cutaneous Sensory Feedback in a Subject

Loss of a limb or loss of peripheral sensation (as in diabetic neuropathy) deprive a person of the cutaneous sensation that is necessary to differentiate between surfaces and to feel pressures. Cutaneous sensation is also lost when synthetic materials create a barrier between skin surfaces and the environment (e.g. when wearing gloves). The following is a second embodiment of the method of the invention, whereby cutaneous sensation is delivered to any innervated patch of skin, enabling restoration of function.

All implanted materials described in the following embodiments can include or be coated in the materials described above in the first embodiment of the invention.

2.1 Surgically-Implanted Array of Permanent Magnets

Figure 5:
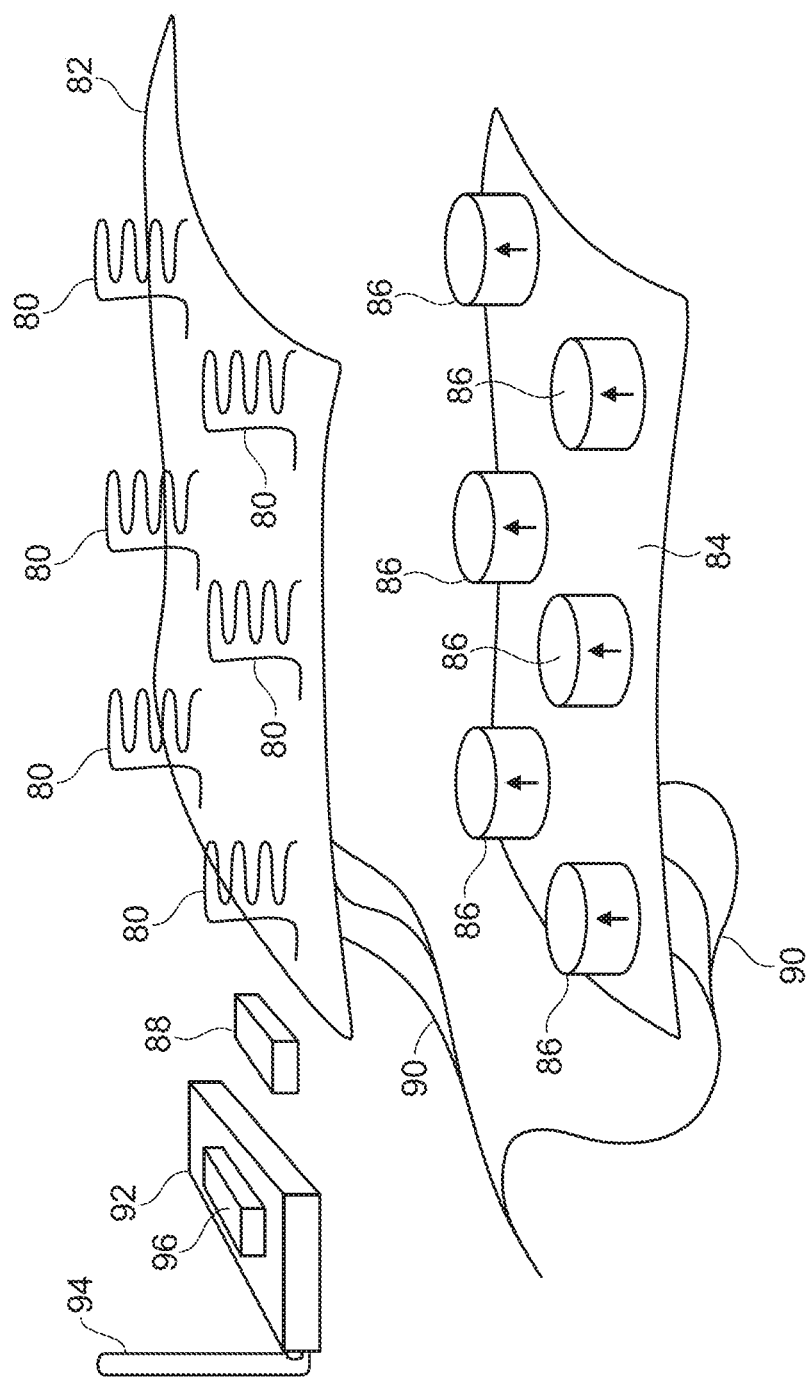
FIG. 5 is a schematic representation of still another embodiment of a method of the invention, wherein electromagnetic coils are mounted external to a body of the subject and magnets are implanted into or sutured onto an ectopic skin graft.

In one version of this embodiment of the method of the invention, an array of electromagnetic coils 80 is mounted external to the body (FIG. 5). Beneath the surface of skin 82, an innervated ectopic skin graft 84 is positioned such that the epidermis is oriented away from or toward external skin layer 82. An array of permanent magnets 86 is implanted into, or sutured onto, the skin graft. To deliver tactile sensation, an electric current is passed through external electromagnetic coils 80 using controlled current source 88, establishing a magnetic field and attracting or repelling implanted permanent magnets 86. These materials compress, stretch, or otherwise manipulate skin 84, causing cutaneous sensation to be delivered along peripheral neural pathways 90 to the central nervous system. By temporally and spatially modulating electromagnetic coil 80 activation patterns, it is possible to deliver a spatial and temporal continuum of cutaneous sensation.

Touch or pressure sensor readings from another device (such as an external bionic limb) are fed via data transfer antenna 94 or via a wired transmission line into computer 92 which is employed to process sensor readings and/or mapping of sensor readings into biomimetic cutaneous activation patterns. The computer and sensors may be powered by an external power supply or by portable battery 96. For example, artificial pressure and shear sensors on the fingertips of a bionic hand can be fed into computer processors either within a bionic arm, or into computer 92 sitting adjacent to the array of electromagnetic coils 80. A computational algorithm can then determine the activation patterns of the electromagnetic coils 80 to deliver realistic cutaneous fingertip sensation.

Ectopic skin portion 84 can come from several potential sources. In one implementation, a neurovascular island flap can be translocated and placed subdermally. In another implementation, a vascularized skin graft can be placed at the distal end of a transected cutaneous nerve, where the nerve reinnervates the skin graft. In yet another implementation a nerve-intact skin graft with compromised vasculature can be allowed to revascularize. In yet another implementation, a free skin graft (denervated and devascularized) can be placed in the vicinity of a transected cutaneous nerve and allowed to be reinnervated and revascularized.

External electromagnetic coils 80 can, but need not have a high-permeability core. They can be affixed to an external surface of the body by employing an adhesive, a piece of clothing, a rigid anchoring system, or any other attachment mechanism, or they can be affixed to a prosthetic, orthotic, or exoskeletal interface, such as a socket in the case of a prosthesis. The coils can also be integrated into a printed circuit board.

Implanted permanent magnets 86 can be distinct implants, or can be formed into a single patch for easy and repeatable implantation. These magnets can be positioned pseudo-randomly across the surface of the skin, or organized to correspond precisely to the positions of electromagnetic coils 80.

2.2 Surgically-Implanted Array of Ferromagnetic Materials

Figure 7:
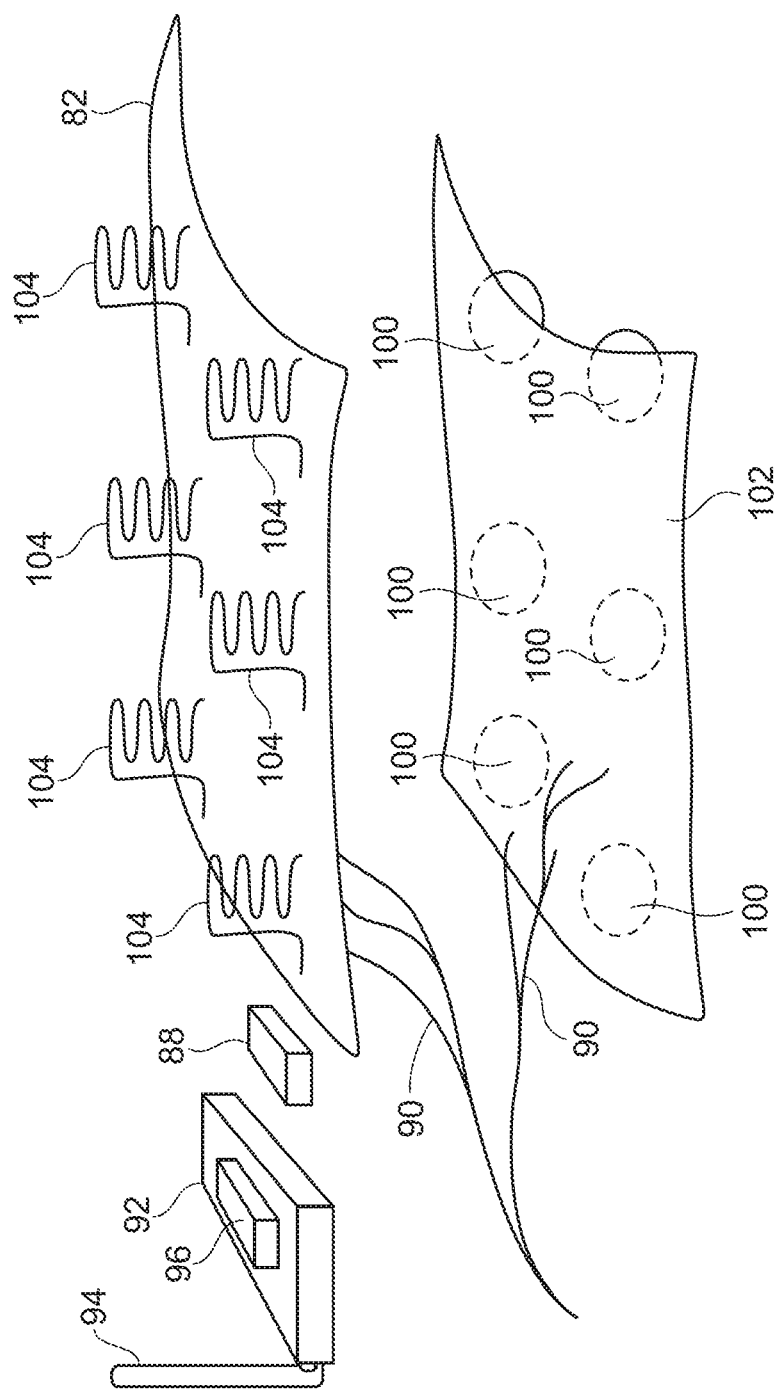
FIG. 7 is another embodiment of a method of the invention, wherein ferromagnetic material instead of the permanent magnets of FIG. 5 are implanted onto or within an ectopic skin graft.

A second version of this embodiment of the invention is identical to the first version, except that one or more pieces of ferromagnetic material 100—instead of permanent magnets—are implanted onto or within ectopic skin graft 102 (FIG. 7). Because unmagnetized ferromagnetic materials do not create their own magnetic field, in this version the external electromagnetic coils 104 will only be able to attract the implants, rather than both attract and repel those implants. Alternate graft placement geometries can be employed to communicate all desired sensations employing only magnetic attraction.

Figure 8:
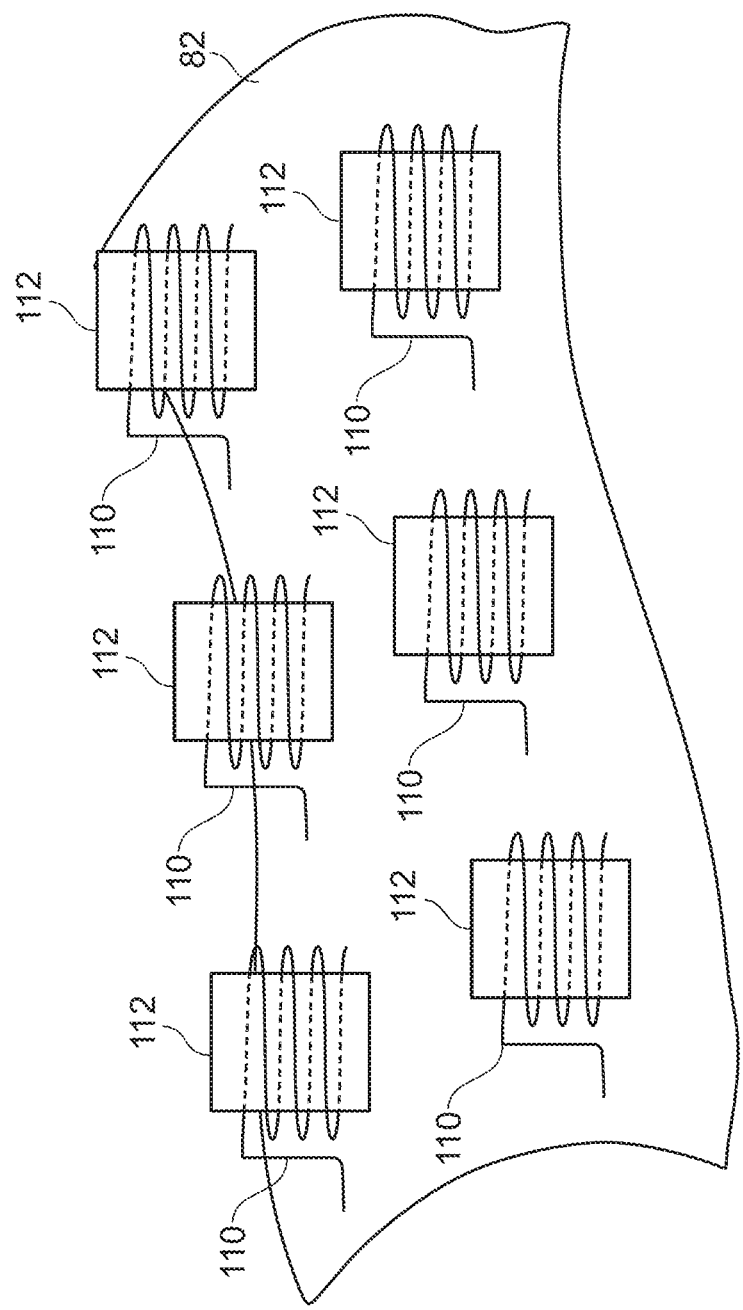
FIG. 8 is a schematic representation of an embodiment of an arrangement of electromagnetic coils, each with a ferromagnetic or permanently-magnetized plunger, to form a solenoid array according to another embodiment of the method of the invention.

2.3 Externally-Mounted Tactile Array Using Solenoids, Linear or Rotary Motors, Cables and Levers, Pneumatics, or Compressed Air In a third version of the second embodiment of the method of the invention, instead of relying upon implanted magnetic materials, an array of actuators located entirely external to the body is employed to provide non-invasive delivery of sensation. Several alternative methods can be employed to construct an external tactile array that delivers cutaneous sensation. These include, for example:

1. Solenoids. A plurality of electromagnetic coils 110, each with ferromagnetic or permanently-magnetized plunger 112, comprise a solenoid array (FIG. 8). In this version, solenoids are employed to deliver a high dimensionality of sensation with high temporal and spatial continuity. Forces from each solenoid are applied perpendicular to the skin.
2. Linear motors. A plurality of linear motors, which may include linear stepper motors, are placed on the surface of the skin, perpendicular to the skin. Examples of linear motors which can be used for this embodiment include Faulhaber Linear DC Servometer Series LM 0830 or the NI Lab NL040X Miniature Tubular Linear Motor.
3. Rotary motors. As rotary motors have higher efficiency and greater torque output than linear motors, an array of rotary motors can be configured to apply forces to the skin.

To accomplish this, each motor is configured with a transmission to convert rotary torque produced by the motor into linear force on the skin. Example transmissions include:

a. Lever arm. Force on the skin is created using a lever arm with a point that touches the skin's surface.
   b. Rack and pinion. Pinions are each oriented in the direction of applied force, whether perpendicular to the skin (pressure) or parallel to the skin (shear) in either of two dimensions.
   c. Ball screw. A ball screw be configured to travel through the center of the electric motor, or be oriented in parallel with the motor.
   d. Any combination of the above configurations can be employed to construct an array of force generators to provide a continuum of shear and pressure forces across the surface of the skin.

Figure 9:
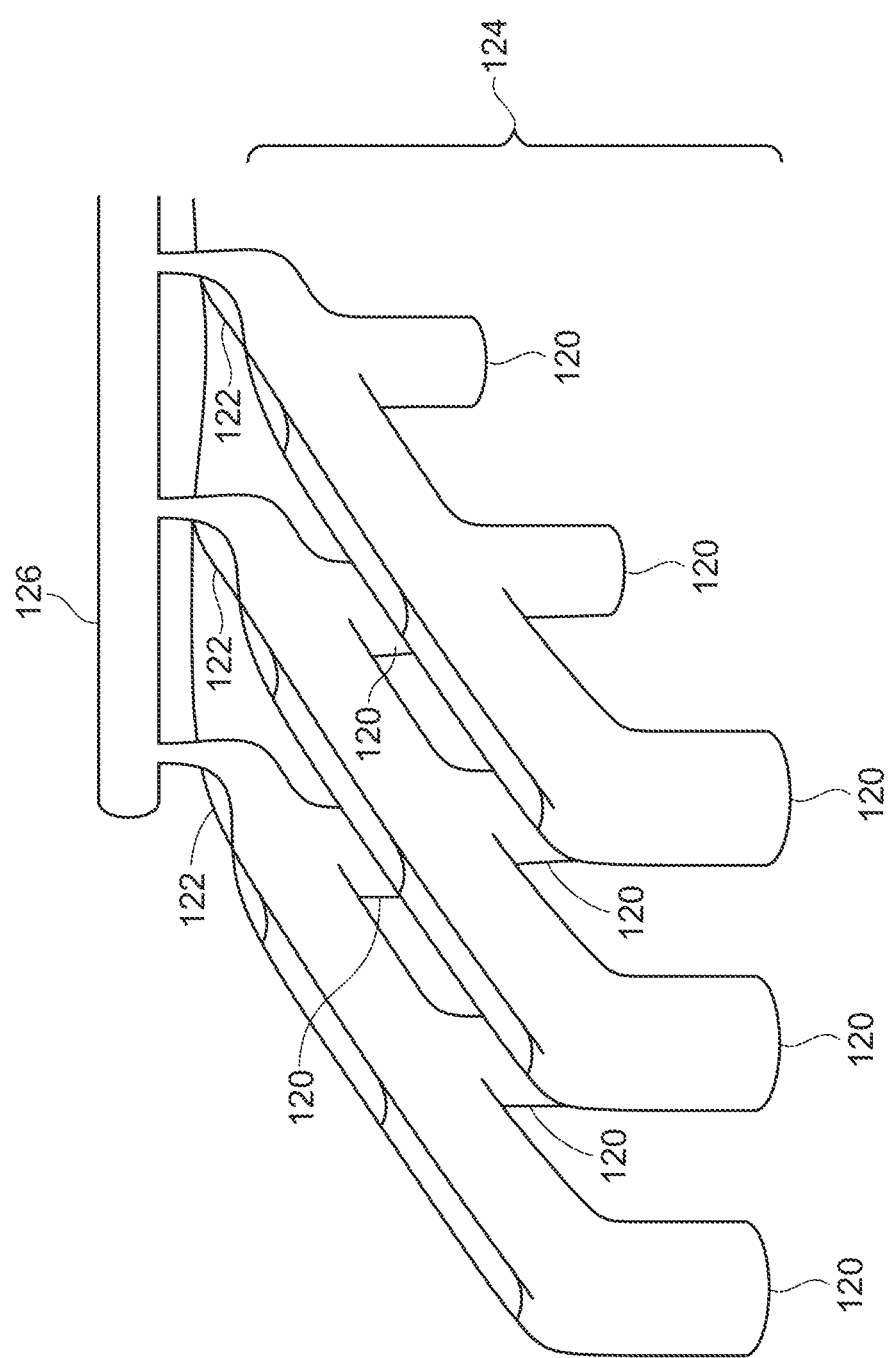
FIG. 9 is a three-dimensional representation of an array of electrically-controlled solenoid valves as employed in still another embodiment of a method of the invention.

4. Rotary motors with cables and levers. Rotary motors, as described above, can be incorporated into a single package worn on the body, such as in a backpack. Bowden cables are then employed to transmit the force to lever arms at the stimulation site, with lever arms providing for stimulation in three dimensions (shear parallel to the skin in two dimensions and pressure perpendicular to the skin in one dimension).
5. Pneumatic or hydraulic tactile array. The same architecture can be constructed utilizing pneumatic or hydraulic force generation. A pneumatic or hydraulic array can be employed to generate force on the surface of the skin. These forces are primarily introduced perpendicular to the skin to create pressure on the skin surface, but the forces can also be introduced in parallel to the skin to create shear forces as well. In the case of pneumatic arrays, these forces can be delivered either by a piston 120 or directly via the flow of air. In the cause of hydraulic arrays, a piston can be employed. In either case, fluid flow and actuation can be governed by an array of electrically-controlled solenoid valves (FIG. 9). The movement of each piston 120 is governed by a computer through data transmission lines 122 governing the pressure through valves corresponding to each piston 120. Pressure is delivered through a manifold 124 supplied by a pressurized pneumatic line 126. The valves are located either near the force delivery site or at a more convenient location on the body for bearing the load of the solenoid and compressors. To generate fluid pressure, either a motorized fluid compressor or a pre-compressed air supply can be employed.

All actuators within a tactile array are positioned to apply linear forces perpendicular to the surface of the skin. By tripling the number of actuators, and arranging the transmission such that forces are applied orthogonally on the surface of the skin, this embodiment can be extended to provide shear feedback along the surface of the skin in two dimensions.

In addition to its utility in providing somatotopically-matched feedback to reinnervated or surgically preserved cutaneous tissues, this version of this embodiment of the invention can also be applied to deliver referred sensation to natively innervated skin. As an example of this application, a person without feeling in their feet, such as a person with diabetic neuropathy or an amputee, can have a sensor array installed on the base of their shoe or prosthesis. The signals from the sensor array are then relayed to a tactile array on a skin surface where the person still has sensory perception, such as the back, upper leg, stomach, or arm.

Figure 6:
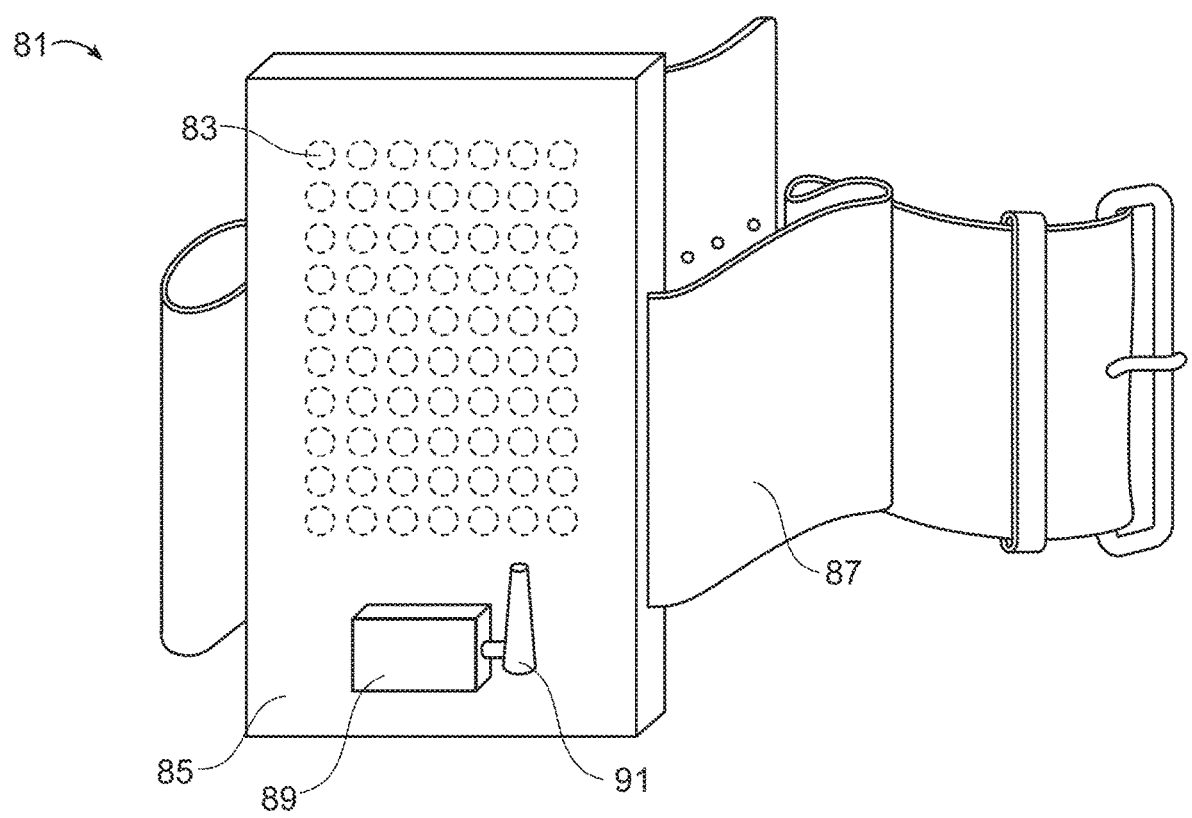
FIG. 6 is an embodiment of a device employed in another embodiment of a method of the invention that provides cutaneous sensory feedback in a subject.
Figure 6:
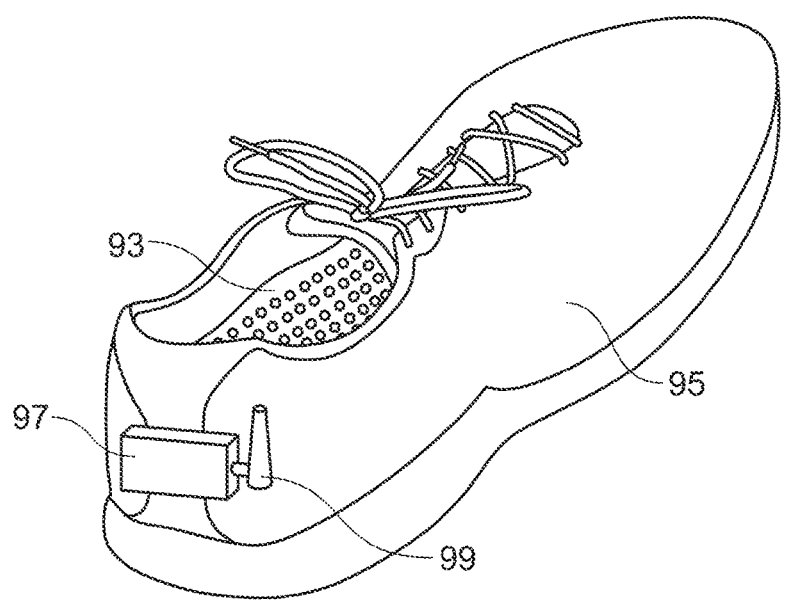

In one specific embodiment, shown in FIG. 6, device 81 includes tactile array 83 applied to a first surface, such as skin at a waist of a subject. Tactile array 83 is mounted on housing 85 that is fixed to attachment strap 87. Attachment strap 87 can be employed to affix tactile array 83 to the first surface. Receiving computer-and-battery assembly 89 is fixed to housing 85 and electronically connected to tactile array 83. Receiving antenna 91 is connected to computer-and-battery assembly 89. Sensor array 93 is located, for example, in a sole of shoe 95 for placement against or proximate to a sole of a foot of the subject. Transmitting computer-and-battery assembly 97 is connected to sensor array 93 and mounted on shoe 95. Transmitting antenna 99 is electronically connected to computer-and-battery assembly 97. A method for providing cutaneous sensory feedback in the subject includes applying tactile array 83 to a first cutaneous surface, such as the waist of the subject, with attachment strap 87. Tactile array 83 is linked, such as by a suitable wired link or a suitable wireless link, to sensors of sensor array 93 at or proximate to a second cutaneous surface, such as a sole of a foot of a subject, at shoe 95. Signals are transmitted from sensors of sensor array 93 at the second cutaneous surface of the subject by way of transmitting computer 97 and transmitting antenna 99 to receiving antenna 91 and then to receiving computer of receiving computer-and-battery assembly 89 for transmission to tactile array 83, thereby providing cutaneous sensory feedback to the subject.

2.4 Closed-Loop Control of Cutaneous Feedback

In this version of the second embodiment of the method of the invention, feedback can be incorporated into any of previous versions by anyone skilled in the art to enable closed loop control of sensation. In one implementation, this feedback comes from an implanted wireless deformation-sensitive array (magnetic or ultrasound-based), as described in the first embodiment of these methods of the invention. In another implementation, a nerve cuff is placed on the innervating cutaneous nerve, to directly monitor the afferent feedback generated by the tactile array.

Embodiment 3: Method for Providing Proprioceptive Cutaneous Sensory Feedback in a Subject An agonist-antagonist myoneural interface (AMI) is a bi-directional neural communication paradigm comprised of two muscles—an agonist and an antagonist—surgically connected in series so that contraction of one muscle stretches the other. The AMI preserves the dynamic muscle relationships that exist within native anatomy, thereby providing proprioceptive signals from mechanoreceptors within both muscles to be communicated to the central nervous system. The AMI provides 1) efferent motor agonist/antagonist signals for the control of external prosthetic motors, and 2) proprioception afferent feedback into peripheral nerves from external prosthetic sensory signals. The AMI utilizes native tissue mechanoreceptors to translate prosthetic sensory information related to muscle stretch and tension into neural signals similar to those experienced in the normal biological milieu. In contrast to alternative approaches to afferent feedback that bypass native biological tissues, AMI models incorporate specialized biomechanical structures inherently present in muscle to transduce information regarding muscle fascicle state and force, as well as skin mechanoreceptor strain. In utilizing biological structures in the design of these systems, when integrated with a bionic limb prosthesis, amputees experience proprioceptive feedback that approximates or equals that of their previously uninjured state while simultaneously providing a safe and viable peripheral neural interface.

The fundamental motor unit to control a biological joint is an agonist-antagonist muscle-tendon pair. Such a muscle-tendon relationship allows organisms to simultaneously control joint state (position and speed) and impedance (stiffness and damping) for upper and lower extremity motor tasks. At least one pair of antagonistic muscles is needed for each degree of freedom of a limb in order to control joint state, torque and impedance. A major input to joint state afferent sensory information derives from the muscle spindle receptors which are known to discharge when a muscle is passively elongated, but which stop firing abruptly whenever that muscle is slackened passively. When a muscle undergoes an active contraction, however, the discharges from spindle receptors within that muscle can be halted or modified, depending on any activation of spindle intrafusal muscle fibers via Gamma motor neurons.

When a muscle on one side of a biological joint contracts (e.g. muscle A) and moves the joint, this motion elongates the muscle (B) that is attached to the opposite side of the joint and causes the muscle B spindle receptors to discharge. Similarly, if contraction of muscle B causes the joint to rotate towards the opposite direction, then muscle A will be elongated causing the muscle A spindle receptors to discharge. Presumably, the arithmetic difference between the activity levels of muscle A and muscle B spindle afferents would be representative of the "joint" position. This "push-pull" system that exists on each side of a joint in normal physiology can be emulated when transferring muscles by placing them in opposition to each other using a suitable mechanical system that couples their movements to each other.

The AMI can be used to provide force feedback from a prosthetic limb. By externally imposing forces on the AMI muscles and tendons, the forces borne on the AMI agonist can be controlled by the external prosthetic processors based upon synthetic force sensory information from the corresponding wearable robotic joint. For example, when an upper extremity prosthetic user picks up a bar bell weight and flexes her prosthetic wrist, this force can be applied to the AMI corresponding to wrist flexors/extensors, allowing the user to experience the barbell weight. The magnitude of the applied force is proportional to the estimated force that would have been applied by the wrist flexors against the bar bell load prior to limb amputation.

Alternatively, an external force applied on the AMI by the bionic limb controller can exert a position control on the agonist/antagonist muscles of the AMI by closing the loop using measured fascicle states. In the case where an external agent is positioning the external bionic joint, such positions can be reflected on the agonist/antagonist muscles in order for the prosthetic user to receive accurate proprioceptive feedback. For example, if another person grasps the bionic hand of the prosthetic user with their hand in order to shake the hand of the prosthetic user, such a handshake may forcibly change the positions of the bionic joints. Bionic joint state sensory information can serve as control position and speed targets for a force control applied to the AMI muscles by microprocessors positioned on the bionic limb. For example, if the handshake flexed the bionic wrist, the force controller can receive bionic wrist state information from a synthetic wrist sensor, and apply an electrical activation to the AMI agonist proportional to the error between the measured bionic wrist position/speed and the measured position/speed from muscle fiber state sensors, causing the muscle to contract and the antagonist to stretch. The prosthetic user can then experience the position of their bionic wrist as imposed by the handshake through afferent feedback to the spinal cord from muscle spindle receptors in the agonist/antagonist pair.

The versions of the method of this embodiment of the invention described in subsequent sections 3.1 and 3.2 provides an electromagnetic mechanism for imposing forces on the AMI muscle pairs. The method of this embodiment of the invention can also be employed to apply forces on muscles in their original anatomical locations to, for example, deliver feedback to the user of a prosthesis, orthosis or exoskeleton.

3.1 Permanent Magnet Implants Coupled with Electromagnetic Coils

Figure 10:
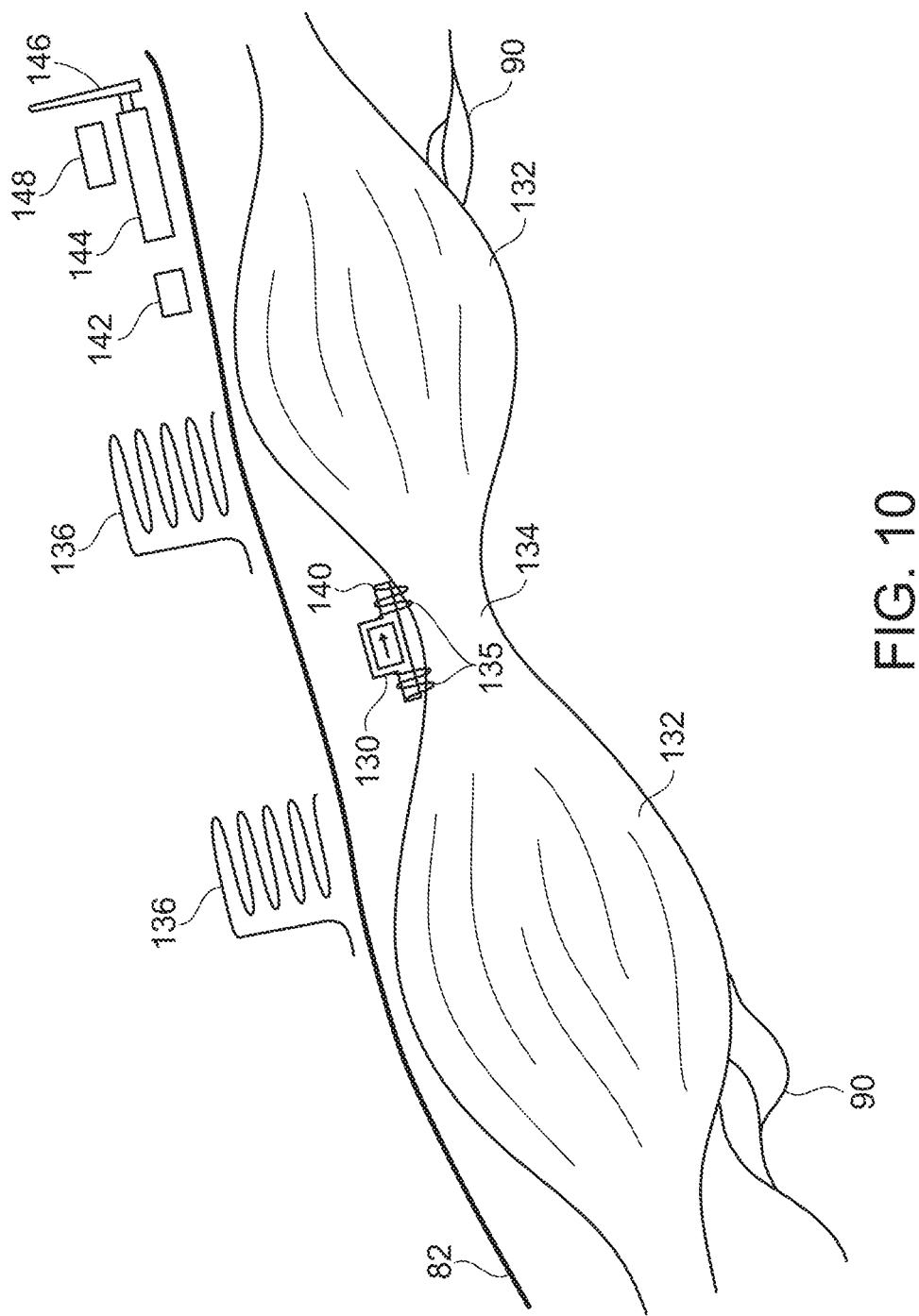
FIG. 10 is a schematic representation of an embodiment of electromagnetic coils and a permanent magnet on a tendon as employed in a method for the providing of transcutaneous imposition of force onto muscle tissue according to yet another embodiment of the method of the invention.

A first version of this third embodiment of the method of the invention provides transcutaneous imposition of force onto muscle tissue. In this version, one or a plurality of permanent magnets 130 is implanted within muscle 132 or tendon 134 or sutured to the surface of the muscle or tendon (FIG. 10). A plurality of electromagnetic coils 136 mounted external to the body are oriented such that passing electrical current through electromagnetic coils 136 creates a magnetic field that attracts or repels permanent magnets 130 and applies a corresponding force on muscle or muscles 132.

When used in conjunction with the AMI, this version can be employed to impose force on one of muscles 132 within the AMI pair. Force applied to either muscle within an AMI will result in activation of Golgi tendon organs and muscle spindles within both that muscle and its partner, communicating muscle force, length, and velocity to the central nervous system via peripheral neural pathways 138. FIG. 10 shows this embodiment employed in proprioceptive feedback using permanent magnet 130 on tendon 134 of an AMI muscle pair. Suture 135 attaches magnet 130 to tendon 134.

Electromagnetic coils 136 employed can be spiraled or coiled wire with or without a high permeability core. Implanted permanent magnets 130 and any associated coatings 140 are as described in the first embodiment of the method of the invention.

Current injection into electromagnetic coils 136 can be delivered by controlled current source 142, which can be driven by computer 144. This computer can be equipped with data transfer antenna 146 for receiving signals from another device, such as a bionic joint sensor. Computer 144 and controlled current source 142 can be powered by an external power supply or by portable battery 148.

Figure 11:
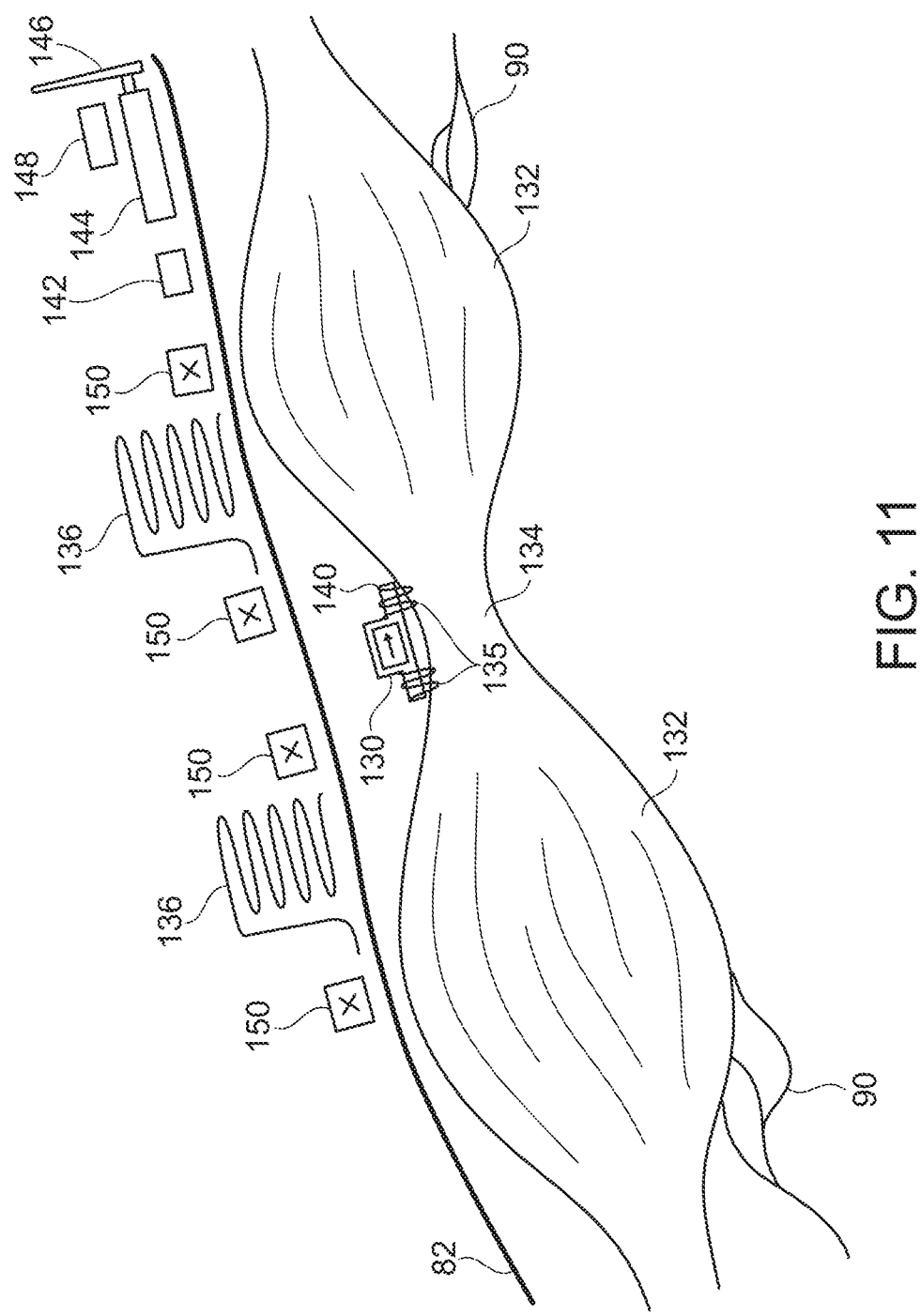
FIG. 11 is a schematic representation of the arrangement shown in FIG. 10, but further including muscle-state sensing magnetometers, as employed in another embodiment of the method of the invention.

This embodiment can be combined with muscle-state sensing magnetometers 150 on the surface of the skin (FIG. 11). Variations of magnetic field from permanent magnet 130 and ferromagnetic material 154 (FIG. 12) caused by changes in position can be picked up by the magnetometers and employed for sensing muscle lengths.

3.2 Ferromagnetic Material Implants Coupled with Electromagnetic Coils

Figure 12:
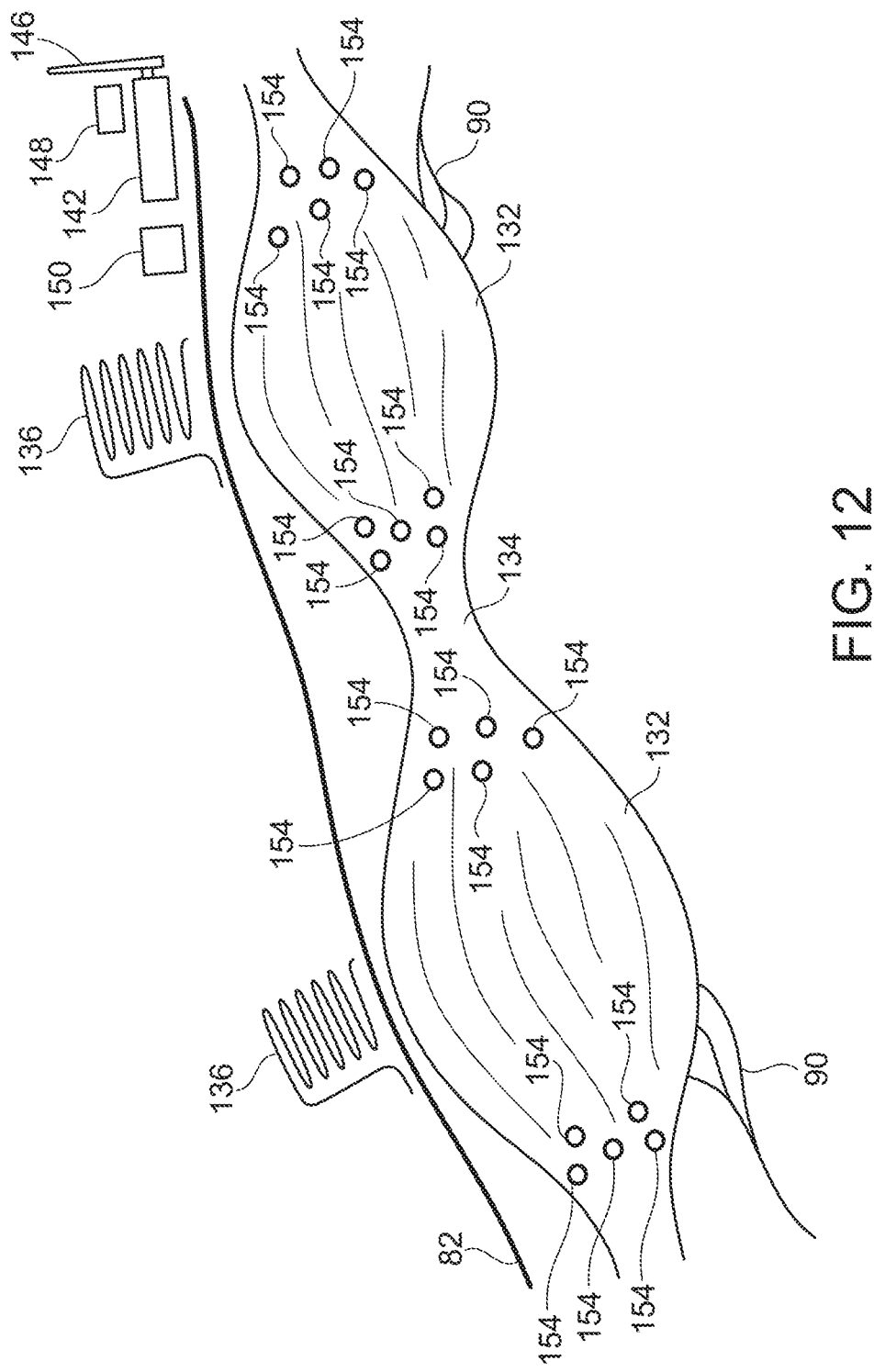
FIG. 12 is a schematic representation of a version of the embodiment of the method of the invention, wherein ferromagnetic material, instead of permanent magnets, shown in FIG. 11, are implanted onto or within muscles or tendons, as employed in yet another embodiment of the method of the invention.

The second version of the third embodiment of this invention is identical to the first, except that one or more pieces of a ferromagnetic material 154—instead of permanent magnets—are implanted onto or within muscles 132 or tendons 134 (FIG. 12). Because unmagnetized ferromagnetic materials do not create their own magnetic field, in this embodiment external electromagnetic coils 136 are only able to attract implanted ferromagnetic materials 154, rather than both attract and repel. Alternate implant placement geometries can be employed to transmit forces using only magnetic attraction. Implanted ferromagnetic materials 154 are as described in the first embodiment of the method of the invention.

Embodiment 4: A Method for Selectively Stimulating at Least a Portion of Axons or Nerve Fascicles of a Neuron of a Subject Known neural interfacing technologies are often limited by an inherent trade-off between specificity and invasiveness. This embodiment of the method of the invention, in at least one version, employs radio-frequency electromagnetic waves to wirelessly communicate with nerves.

Known electrical stimulation of nerves often employs multiple electrodes applied in proximity to a target area. Specificity in the area of stimulation is increased by using electrodes that are closer together, more deeply penetrating, or smaller, and in some cases by using a plurality of electrodes. This embodiment of the method of the invention, in contrast, does not require electrodes to be physically touching biological tissue in order to deliver stimulation to axonal targets. Instead, the signal is delivered wirelessly at a sufficiently high power to cause the nerve to act as a receiving antenna.

Although pure high-frequency electrical signals at constant amplitude typically are insufficient to promote neural depolarization, modulating signal amplitude by employing a low-frequency envelope can cause neuronal activation. For example, a sinusoidal envelope at a frequency in the 1-100 Hz range causes depolarization, even when the carrier wave is above the 1-2 kHz stimulation threshold. This concept is exploited in the field of interferential therapy. Non-sinusoidal waveform envelopes, such as triangular or square waves or other custom waveforms (e.g. a waveform mimicking an axonal action potential) can also elicit neural depolarization. Although not wishing to be limited to any particular theory, it is speculated that the neuron acts as an envelope filter, seeing only the amplitude of the signal and not the carrier wave. In practice, such waveforms are typically implemented by employing a temporal interference from multiple electrode pairs, but the biophysics of envelope filtering also enables the signal to be delivered from a single electrode pair as an amplitude-modulated carrier wave.

One version of the fourth embodiment of the method of the invention includes a stimulator that employs radio-frequency waves (30 MHz-300 GHz) for neuronal stimulation.

Though the embodiments below refer to peripheral nerve stimulation, this version of this fourth embodiment of the method of the invention can also be employed to stimulate the central nervous system (e.g., the spinal cord or brain).

4.1 Nerve cuff

In this version of the fourth embodiment of the method of the invention, phase shifting of antennas in an array is employed to electronically steer at least one member of the group consisting of electromagnetic signals and high power ultrasound waves. A schematic representation of this principle is shown in FIGS. 13A-13C (prior art), which shows cross sections of monopole or dipole antennas 160 in various configurations, and electromagnetic wave crests 162 for the electric field component of the wave from each of the antennas 160. In a linear array, shown in FIG. 13A (prior art), phase offsets cause the wave to change direction by electronically controlling phase differences between electromagnetic wave crests 162 from each antenna 160. The resulting wavefront 164 is the sum of the electromagnetic waves from all of the antennas 160. A linear array of antennas 160 can also be employed for electromagnetic focusing by the use of phase shifting. FIG. 13B (prior art) shows an example of electronically-focused electromagnetic waves from a linear array of antennas 160 at focal point 166. FIG. 13C (prior art) shows how a circular array of antennas 160 can be employed to create an electromagnetic focal point 166 by phase shifting of electromagnetic wave crests 162.

Figure 14:
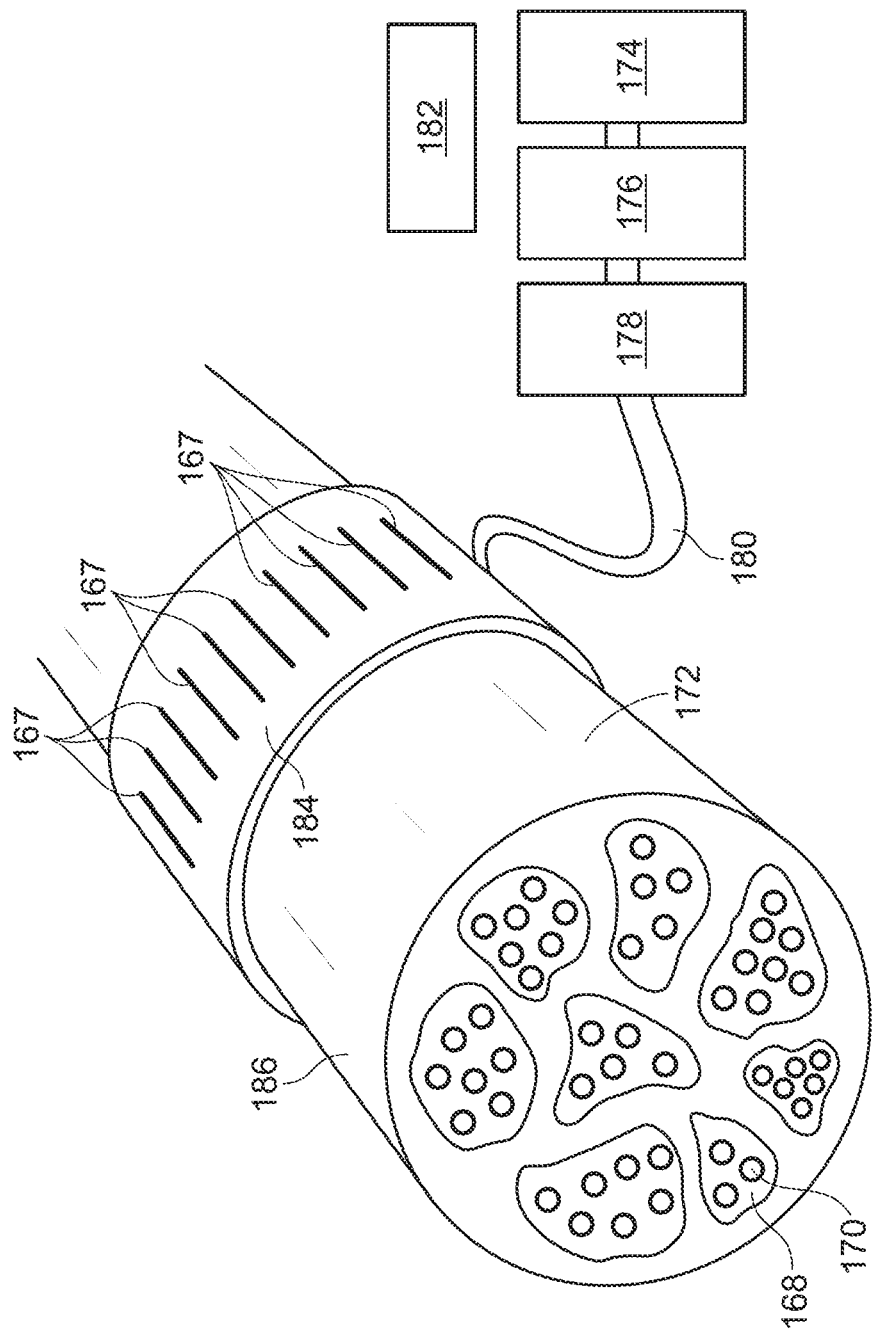
FIG. 14 is a three-dimensional illustration of an implantable biocompatible nerve cuff placed on a nerve in combination with a schematic representation of a controller, as employed in another embodiment of the method of the invention.

Also, in this version of the fourth embodiment of the method of the invention, one or more antennas 167, such as monopole or dipole antennas, are employed to generate radio-frequency electromagnetic waves. When those waves are each steered toward nerve fascicles 168 or groups of axons 170 (FIG. 14), a focal point of the signal emerges where the waves overlap. If the signal at this focal point is of sufficient amplitude to activate the target neurons, nerve 172 will depolarize. By steering this focal point, one or more different axon subgroups are selectively targeted. Multiple simultaneous focal points can be generated from a single array, causing simultaneous activation of multiple axon subgroups. The signal is created by a combination of controller 174, radio frequency waveform generator 176, and radio frequency amplifier 178, and is delivered by coaxial cables 180 or waveguides. A radio frequency repeater can be employed in this invention to boost the signal strength en route to the antenna array. The controller, waveform generator, and amplifier are powered by a suitable source, as is known in the art, such as an external power supply, or battery 182 for stand-alone operation. Additionally, the controller can link to other devices via a data transfer antenna or wired transmission line.

The antennas employed in embodiments of this invention can be paired with reflectors, such as parabolic reflectors. Electromagnetic waves are steered by, for example, mechanically actuating one or more parabolic reflectors, by phase shifting the antenna array, or by a combination of these two methods.

Although amplitude-modulated radio-frequency nerve stimulation can be employed for completely non-invasive nerve stimulation (see, e.g., versions 4.2 and 4.3 infra), the alternative of this version includes an implantation nerve stimulator. This enables for higher selectivity and lower invasiveness than known implantation options for nerve stimulation. Employing amplitude-modulated radio-frequency nerve stimulation, the signal can be focused without damaging the nerve. In this first version of the fourth embodiment of the method of this invention, radio-frequency electromagnetic waves are generated by an antenna array embedded within implantable biocompatible nerve cuff 184, shown in FIG. 14. FIG. 13C (prior art) shows an example of how the stimulation region generated by an antenna array that wraps completely around the nerve can be electronically steered. Alternatively, any implantable architecture that would hold the antenna array steady with respect to the nerve can be employed (e.g. a linear array sutured tangent to the epineurium 186).

In this specification, electromagnetic wave frequencies can be limited to the gigahertz range, which is a lower limit determined by a maximum biocompatible length of the nerve cuff. Gigahertz range frequencies can be required to create a focused stimulation point within the nerve, as the selectivity of this method of wireless stimulation increases with increasing frequency.

Within the nerve cuff, the antennas consist of a conductive material such as stainless steel, silver, gold, poly(3,4-ethylenedioxythiophene) (PEDOT), aluminum, copper, tungsten, or zinc. The coating around the antennas and the structure of each antenna itself can be made of a suitable material, such as is known in the art, including, for example a silicone (such as NuSil™ Medical Grade silicone), parylene, biomedical polyurethane (such as Bionate® Thermoplastic Polycarbonate-urethane PCU, Bionate® II PCU, BioSpan® Segmented Polyurethane (SPU), CarboSil® Thermoplastic Silicone-Polycarbonate-urethane (TSPCU), Elasthane™ Thermoplastic Polyether-urethane (TPU), PurSil® Thermoplastic Silicone-Polyether-urethane (TSPU) or any other coating manufactured by DSM Biomedical), or some other biomedical polymer (e.g. polydimethylsiloxane, or PDMS) for biological compatibility and shape.

4.2. Extremity Band

Figure 15:
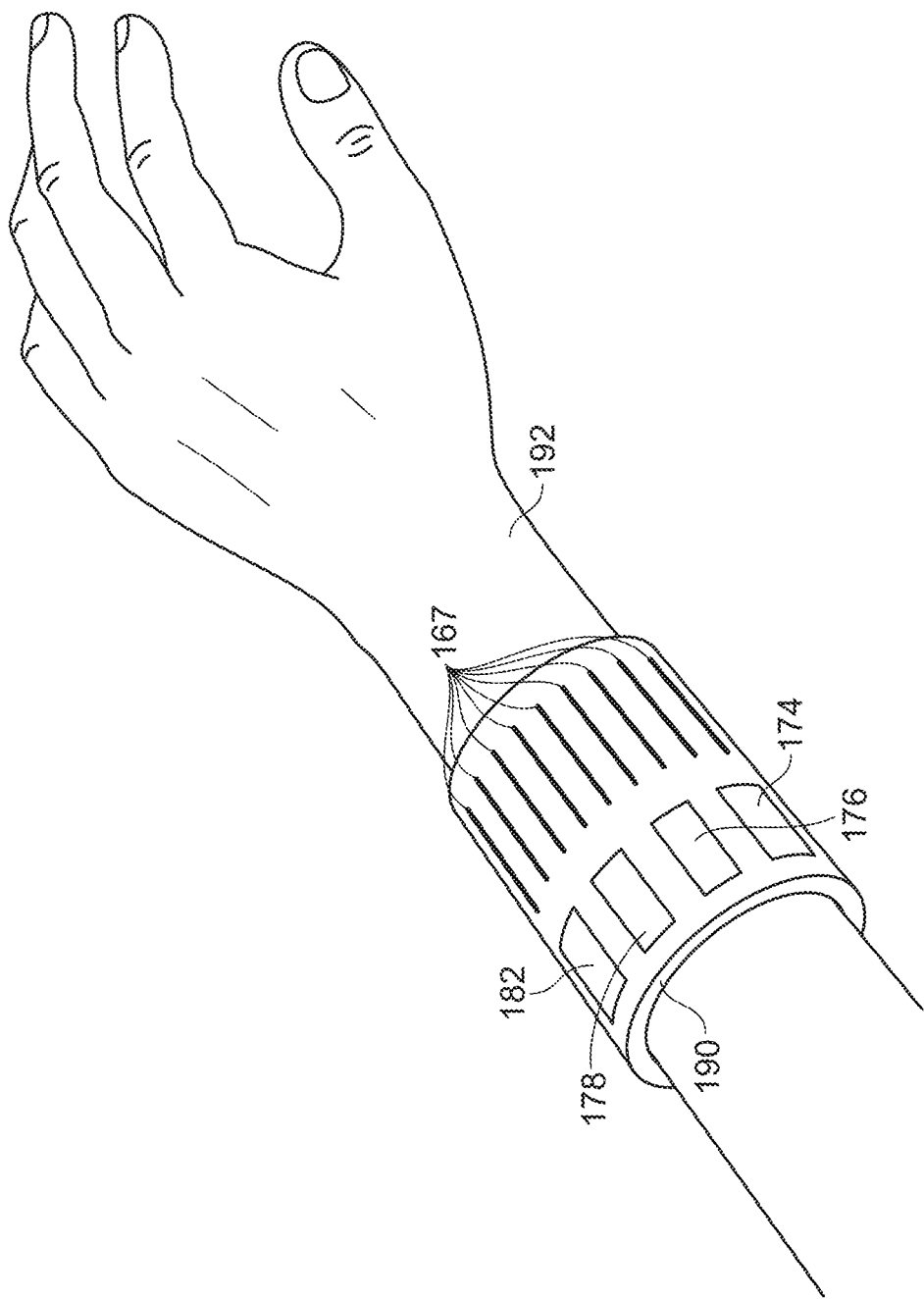
FIG. 15 is a three-dimensional arrangement of antennas worn in an array on a band around an anatomical extremity of a subject, as is employed in still another embodiment of the method of the invention.

A second version of this fourth embodiment of the method of the invention is identical to the version described in 4.1, except that the antenna array is worn external to the body, in band 190 around anatomical extremity 192, such as the upper or lower leg, upper or lower upper arm, neck, or anywhere else on the body, such as is shown in FIG. 15. In this version, wireless neural stimulation is achieved non-invasively, at least in one specific embodiment, by employing stimulation in a megahertz and gigahertz frequency range.

Because precise position information about the antenna array and target assists signal focusing (the precision requirements being determined by the frequency of the carrier wave), an externally-worn band is preferably designed such that precise relative antenna positions are known or can be calculated. To achieve this, the band can be, for example, a solid band that conforms tightly to the body, a flexible band with position and angle sensors built-in employing a combination of potentiometers, encoders, or flex sensors, or a hybrid of two of these. Alternatively, the antenna array can be, in certain embodiments, self-sensing, measuring the time delay of pulses from other antennas in the array and calculating its own geometry based on relative distances between the antennas in the array.

4.3. Skin Patch

As a modification to embodiment described above at 4.2, antenna arrays can be embedded in skin patches rather than in a worn band. These can be short skin patches to form linear or curved arrays (as shown in FIG. 13B (prior art) for a linear focused area, and similarly used for focusing in the case of a curved array), or can be sufficiently long to wrap around an extremity (following the pattern of FIG. 13C (prior art), positioned similarly anatomically to the embodiment described at 4.2. The relative position of each antenna on the skin can be determined by calibration after patch placement. This calibration accounts for the shift in relative position caused by muscle flexion. Muscle flexion sensing (for instance, with the use of the systems described in Embodiment 1) can be employed to determine when the positions of the antennas have been shifted relative to the nerve and relative to one another.

Embodiment 5: A Method for Tracking at Least One Magnetic Marker

Sensing the intent of the user of a wearable robot for volitional control of the wearable robot often requires high accuracy and low latency. For instance, in the control of prostheses, orthoses, or exoskeletons, balance under voluntary control requires high accuracy and low latency; otherwise, for instance, the user of a prosthesis may fall over due to lack of ability to respond in a timely manner to imbalances. The prosthesis user generally requires fast, accurate feedback about how far they are from standing upright. This, of course, extends to all tasks requiring manipulation of a robotic extremity with fine control, especially when this fine control must be performed with rapid response.

As discussed in Embodiment 1 of the method of the invention, while there are various methods for acquiring signaled intent from the wearer, limitations, such as signal-to-noise ratio, level of invasiveness, and limited degrees of freedom, have thus far limited high-accuracy, low-latency control. Embodiment 1.1, described supra, employs, for example, implanted permanent magnets tracked via magnetometers to overcome the constraints of wireless tracking for sensing muscle length, velocity, and force in real-time. The fifth embodiment of the method of the invention significantly reduces that limitation and enables relatively high-fidelity low-latency tracking of one or more magnets in one or more degrees of freedom.

In addition, high-accuracy low-latency magnet tracking enables additional applications, such as sensing of high-frequency muscle vibrations, or mechanomyography. These high-frequency muscle signals give insight into muscle activation and thus can be employed to, among other applications, control force in a prosthesis. Additional applications made possible by this fifth embodiment of the method of the invention are discussed below.

The below versions of this fifth embodiment of the method of the invention describe a magnet tracking system in the context of magnetometers tracking permanent magnets, but all embodiments of this invention are equally applicable to an active coil tracking system wherein the permanent magnets are replaced by active coils which approximate magnetic dipoles. Additionally, all versions are equally applicable to the tracking of ferromagnetic objects which warp the geomagnetic field in such a way that they can be approximated by magnetic dipoles. Further, though the below versions of this fifth embodiment describe the system in the context of tracking spherical magnets, any shape magnet may be tracked with this method via the far-field approximation of the given magnet.

5.1 Permanent Magnet Tracking System

Figure 16:
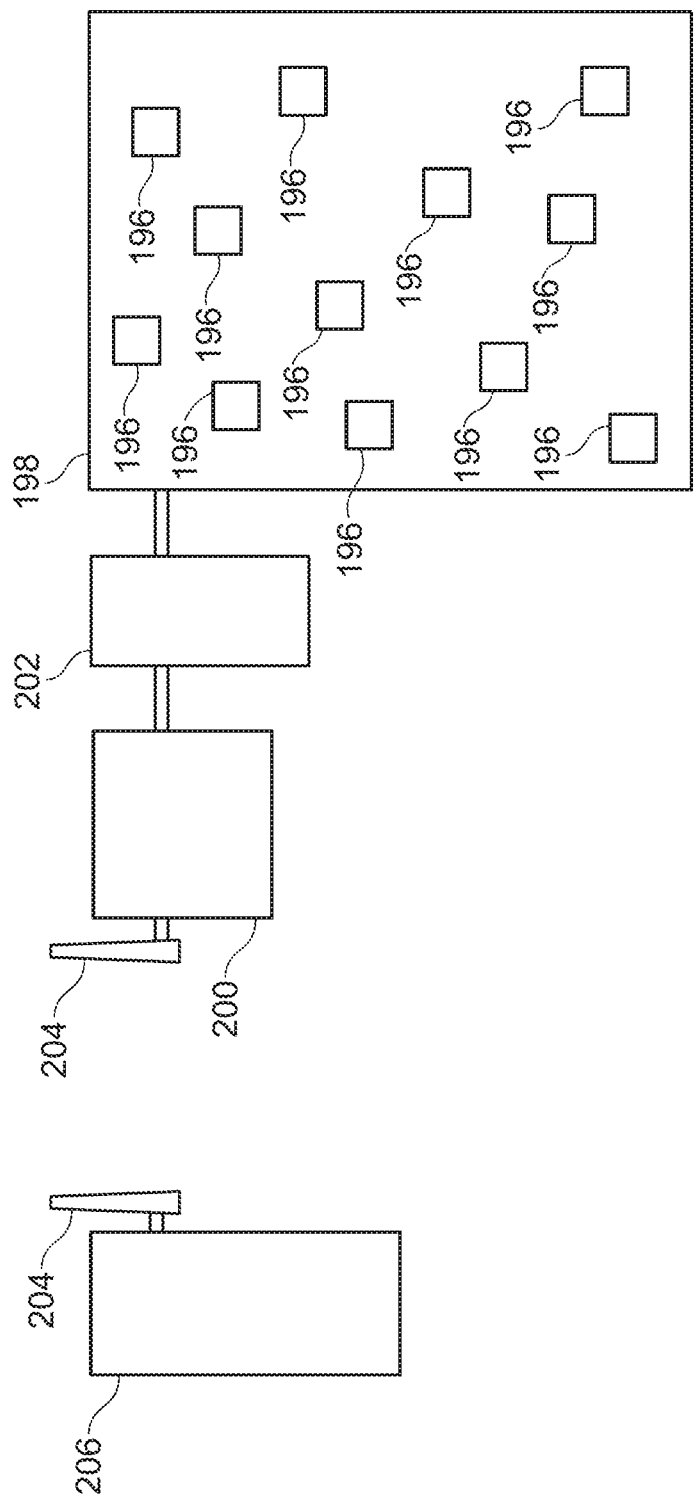
FIG. 16 is a plan view of physical components of an arrangement of a permanent magnet tracking system employed in still another embodiment of the method of the invention.
Figure 17:
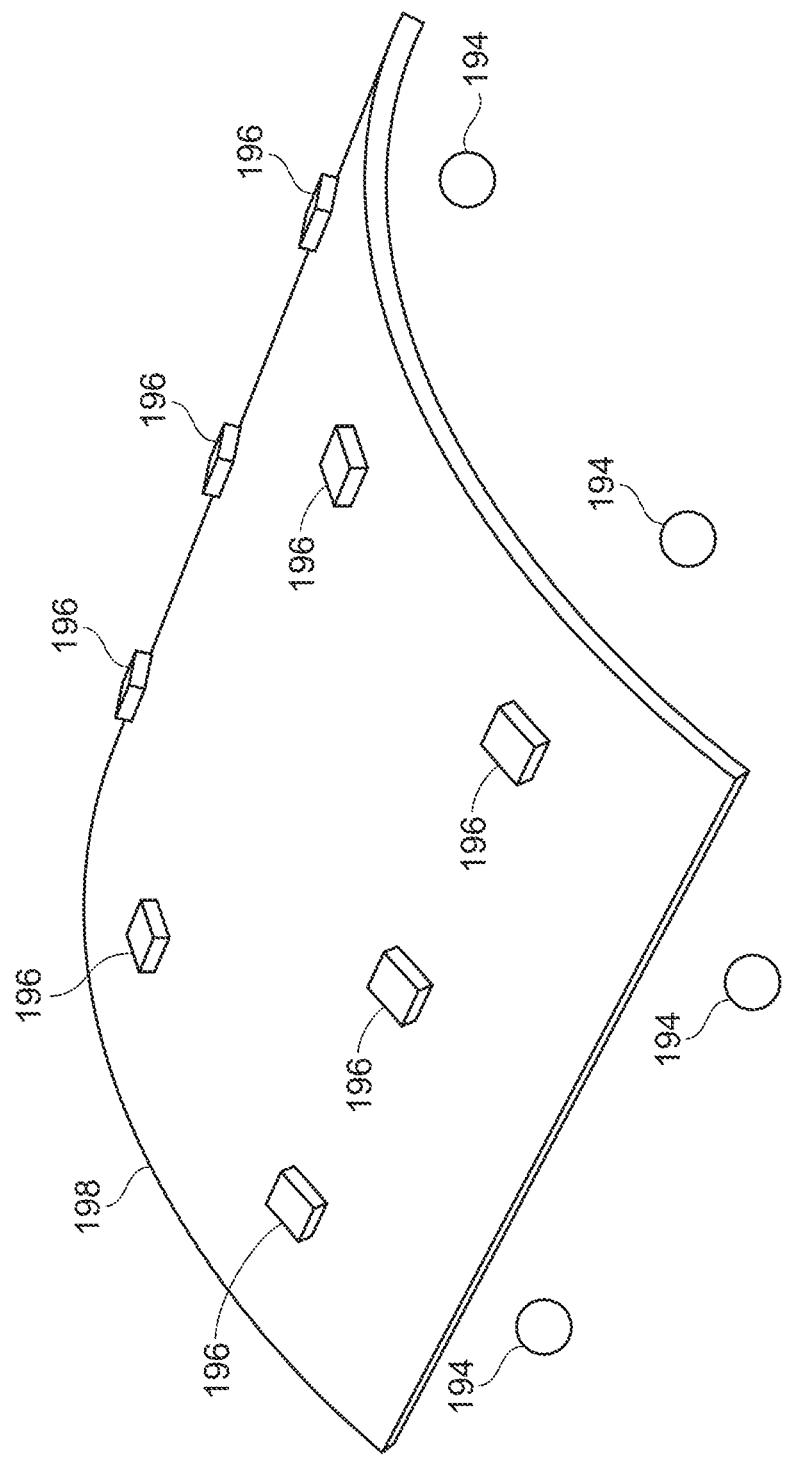
FIG. 17 is a perspective view of the antenna array shown in FIG. 15, in combination with a distribution of permanent magnets, as is employed in another embodiment of the method of the invention.

The first version of this fifth embodiment of the method of the invention includes tracking at least one permanent magnet 194 in at least one-dimension using a plurality of magnetometers 196 in a magnetometer array 198. The physical components of this arrangement are shown in FIGS. 16 and 17. Magnetometers 196 in this version are as described as in Embodiment 1, and additional examples of such magnetometers include but are not limited to the STMicroelectronics LSM9DS1 iNEMO inertial module, the NXP Semiconductors FXOS9700CQ 6-axis sensor, the MEMSIC MMC5883MA 3-axis Magnetic Sensor, or the Analog Devices ADIS16480 Ten Degrees of Freedom Inertial Sensor. The plurality of magnetometers 196 is fixed in magnetometer array 198 in any configuration in three dimensions, including but not limited to arrangement of magnetometers 196 along a single line in space, arrangement in a grid or along a circle, ellipse, parabola, hyperbola, triangle, square, higher-order polygon, random or pseudo-random placement on a plane or surface (such as a circular cylinder, elliptical cylinder, parabolic cylinder, sphere, ellipsoid, or polynomial surface), or arrangement in three dimensions in a grid or in three dimensions in a random or pseudo-random placement. For instance, see FIG. 16 for pseudo-random magnetometer placement on a plane, FIG. 17 for square placement on the surface of a partial circular cylinder, and FIG. 25 for square placement on a plane. Magnetometers 196 employed in this invention may be single-axis, two-axis, or three-axis magnetometers, or some combination of these three. The positions of magnetometers 196 in magnetometer array 198 must be able to be determined relative to one another. Thus, in this version of the fifth embodiment, the relative positions of magnetometers 196 are either fixed or continuously monitored via one or more distance, angle, and/or bending sensors. The data from magnetometers 196 can be sampled by battery-powered microcontroller 200 through $I^2C$ switch 202, such as Texas Instruments TCA9548A Low-Voltage 8-Channel I2C Switch with Reset, if single-addressed I2C communication is used, or via multi-address I2C communication, or via a combination of both, or via SPI protocol or some other communication protocol. This data can then be modified or left in raw form by microcontroller 200 and sent via a set of data transfer antennas 204 or via a data transfer cable to computer 206 or other microcontroller for storage and/or processing, or can be stored and/or processed directly on microcontroller 200.

One or more permanent magnets 194 are constructed of material as described in Embodiment 1, with or without a protective coating. One or more permanent magnets 194 can be configured to translate and rotate in all degrees of freedom. For example, each permanent magnet 194 being tracked can be tracked in three linear degrees of freedom (x, y, and z) and two rotational degrees of freedom (pitch and roll). The magnetic field from a magnetic dipole is, in this example, symmetric about the yaw axis, and since this system employs the magnetic dipole model for tracking permanent magnets 194, yaw cannot be determined from permanent magnet 194 approximated as a single dipole using this system. One or more of permanent magnets 194 in the system can be restricted in one or more degrees of freedom relative to magnetometers 196 or relative to one another, in which case only the remaining degrees of freedom will be tracked. Restrictions on the degrees of freedom of multiple permanent magnets 194 need not be the same from permanent magnet to permanent magnet. Magnetometer array 198 need not be fixed in any way relative to permanent magnets 194 or relative to the world in order to determine the positions, orientations, and velocities of permanent magnets 194 relative to magnetometer array 198, or, equivalently, the positions, orientations, and velocities of permanent magnets 194 relative to one another.

In one specific embodiment, spherical permanent magnets are employed in this method. However, any shape of magnet, such as a cylinder or cube, with any magnetization direction, can be employed with this method by approximating the permanent magnet as a magnetic dipole.

A commonly used method of tracking magnetic markers is to utilize an optimization algorithm. At each step of the optimization, each of the magnetic marker locations, orientations, and strengths (also referred to herein as state parameters), if unknown, are estimated. This estimate is used to calculate a predicted magnetic field at each sensor location in a sensor array. Comparing the predicted magnetic field with the measured magnetic field at each sensor, a prediction error is then computed corresponding to the estimate. The optimization algorithm then determines a relationship between the prediction error and the estimate and uses this relationship to adjust the estimate in a way that minimizes the prediction error.

Numerical derivatives are typically used to investigate the relationship between the magnetic field prediction error and the estimate of the magnetic marker locations, orientations, and strengths. Computing a derivative numerically costs extra time because the prediction error must be calculated for multiple estimates in the neighborhood of each estimate. Further, numerical derivatives inherently introduce error, and thus tend to introduce instability into the optimization. The added computational time and instability not only result in increased tracking latency, but also have the potential to introduce state estimate errors into the tracking when tracked targets change position rapidly.

This embodiment of the method of the invention is a tracking algorithm, implementing the use of analytic derivatives, to track magnetic markers via an optimization algorithm. The analytic derivatives in this tracking algorithm are implemented in a manner that has the benefits of increased numerical stability and causes a significant decrease in latency over other algorithms. In versions of this embodiment of the invention, this tracking method is extended to the tracking of disturbance fields and to the calibration of a sensor array.

The first version of this fifth embodiment of the method of the invention employs an algorithm for tracking the state of the one or more magnets involving the analytic calculation of the magnetic field prediction error Jacobian matrix within an implementation of the Levenberg-Marquardt algorithm or within the implementation of another optimization making use of function gradients in the optimization. The magnetic field prediction error Jacobian matrix is a matrix composed of the derivatives, with respect to each of the estimated parameters, of the errors between the measured magnetic field and the predicted magnetic field as calculated given estimated magnet parameters; in this case it is the derivatives, with respect to estimated magnet positions, orientations and strengths, of the errors between the measured magnetic field values and predicted magnetic field values given the estimates.

In one version of this embodiment, the submatrices of the Jacobian matrix are computed in an optimized cascading calculation, meaning that the Jacobian submatrix elements are calculated in a succession of stages wherein each stage of calculation uses the results of the subexpression evaluations from previous stages and the results of repeated subexpressions are shared between the different matrix elements. The cascading method is described below. This submatrix calculations are alternatively or additionally implemented in parallel in this version, with each of the submatrices being calculated simultaneously before being assembled into a single matrix.

This algorithm considers M spherical magnets and N sensors. The vector magnetic field at each of the N sensors is calculated given an estimate of the positions, orientations, and strengths of each of the magnets. The cost function of the optimization in the algorithm is the difference between the predicted magnetic field and the measured magnetic field, as given by equation I $$E_i = B_i - \tilde{B}_i \qquad (I)$$

Where Ei=(Eix, Eiy, Eiz) is the cost function corresponding to the ith sensor and Bi=(Bix, Biy, Biz) and Bi tilde=(Bix tilde, Biy tilde, Biz tilde) are the predicted and measured magnetic field corresponding the ith sensor, respectively.

The input to the optimization function is an estimate of the magnet parameters. In this algorithm, the jth magnet has a magnetic moment given by equation (II)

$$\overline{m}_j = R_z(\theta_j) R_y(\theta_j) \overline{m}_j \hat{z} = \overline{m}_j (\sin\theta_j \cos\phi_j \hat{x} + \sin\theta_j \sin\phi_j \hat{y} + \cos\theta_j \hat{z}) \qquad (II)$$

where for simplicity in calculations we have defined a variable substitution for the magnetic dipole moment as given in equation III.

$$\overline{m}_j \triangleq \frac{\mu_0}{4\pi} m_j \qquad (III)$$

This algorithm can alternatively regard the magnetic dipole moments in terms of some other coordinate system such as (mjx, mjy, mjz) instead of (mj, θj, φj), but the implementation in terms of mj, θj, and φj allows a known magnetic dipole strength mj to be input into the algorithm, and thus results in a reduction in number of tracked parameters. The orientation can alternatively be considered as an offset from some other axis, but for convenience we choose the positive z axis. If necessary, coordinate systems and reference axes may be switched during tracking. With the position of the ith sensor given by (six, siy, siz) and the position of the jth magnet given by (xj, yj, zj), the vector from the jth magnet to the ith sensor is given by equation (IV)

$$r_{ij} = (s_{ix} - x_j)\hat{x} + (s_{iy} - y_j)\hat{y} + (s_{iz} - z_j)\hat{z} \qquad (IV)$$

The magnetic dipole approximation is employed to calculate the magnetic field prediction ($B_{ix}$, $B_{iy}$, $B_{iz}$) at the ith sensor as equation (V)

$$B_i = G + \sum_{j'=0}^{j'=M} \left( \frac{3 r_{ij'} (\overline{m}_{j'}^r \cdot r_{ij'})}{r_{ij'}^5} - \frac{\overline{m}_{j'}}{r_{ij'}^3} \right) \qquad (V)$$

where G=($G_x$, $G_y$, $G_z$) is a disturbance field, such as the geomagnetic field. Because the inputs to this magnetic dipole approximation are estimated parameters, the change in the magnetic field vector prediction $B_i$ with respect to each estimated parameter is the same as the change in magnetic field prediction error at each sensor, so with the substitutions of equations (VI)

$$\bar{x}_{ij} \triangleq s_{ix} - x_j$$
$$\bar{y}_{ij} \triangleq s_{iy} - y_j$$
$$\bar{z}_{ij} \triangleq s_{iz} - z_j \qquad (VI)$$

each of the submatrices of the magnetic field prediction error Jacobian matrix (corresponding to the ith sensor and jth magnet) is then calculated in this implementation as equation (VII)

$$J_{ij} = \begin{bmatrix} \frac{\partial}{\partial x_j} E_{ix} & \frac{\partial}{\partial y_j} E_{ix} & \frac{\partial}{\partial z_j} E_{ix} & \frac{\partial}{\partial \phi_j} E_{ix} & \frac{\partial}{\partial \theta_j} E_{ix} & \frac{\partial}{\partial \overline{m}_j} E_{ix} \\ \frac{\partial}{\partial x_j} E_{iy} & \frac{\partial}{\partial y_j} E_{iy} & \frac{\partial}{\partial z_j} E_{iy} & \frac{\partial}{\partial \phi_j} E_{iy} & \frac{\partial}{\partial \theta_j} E_{iy} & \frac{\partial}{\partial \overline{m}_j} E_{iy} \\ \frac{\partial}{\partial x_j} E_{iz} & \frac{\partial}{\partial y_j} E_{iz} & \frac{\partial}{\partial z_j} E_{iz} & \frac{\partial}{\partial \phi_j} E_{iz} & \frac{\partial}{\partial \theta_j} E_{iz} & \frac{\partial}{\partial \overline{m}_j} E_{iz} \end{bmatrix} = \qquad (VII)$$

-continued $$\begin{bmatrix} \frac{\partial}{\partial x_j}B_{ix} & \frac{\partial}{\partial y_j}B_{ix} & \frac{\partial}{\partial z_j}B_{ix} & \frac{\partial}{\partial \phi_j}B_{ix} & \frac{\partial}{\partial \theta_j}B_{ix} & \frac{\partial}{\partial \bar{m}_j}B_{ix} \\ \frac{\partial}{\partial x_j}B_{iy} & \frac{\partial}{\partial y_j}B_{iy} & \frac{\partial}{\partial z_j}B_{iy} & \frac{\partial}{\partial \phi_j}B_{iy} & \frac{\partial}{\partial \theta_j}B_{iy} & \frac{\partial}{\partial \bar{m}_j}B_{iy} \\ \frac{\partial}{\partial x_j}B_{iz} & \frac{\partial}{\partial y_j}B_{iz} & \frac{\partial}{\partial z_j}B_{iz} & \frac{\partial}{\partial \phi_j}B_{iz} & \frac{\partial}{\partial \theta_j}B_{iz} & \frac{\partial}{\partial \bar{m}_j}B_{iz} \end{bmatrix}$$

and this matrix is calculated via the simplified calculation shown in equation VIII $$J_{ij} = \begin{bmatrix} -\frac{\partial}{\partial x_{ij}}B_{ix} & -\frac{\partial}{\partial y_{ij}}B_{ix} & -\frac{\partial}{\partial z_{ij}}B_{ix} & \frac{\partial}{\partial \phi_j}B_{ix} & \frac{\partial}{\partial \theta_j}B_{ix} & \frac{\partial}{\partial \bar{m}_j}B_{ix} \\ -\frac{\partial}{\partial x_{ij}}B_{iy} & -\frac{\partial}{\partial y_{ij}}B_{iy} & -\frac{\partial}{\partial z_{ij}}B_{iy} & \frac{\partial}{\partial \phi_j}B_{iy} & \frac{\partial}{\partial \theta_j}B_{iy} & \frac{\partial}{\partial \bar{m}_j}B_{iy} \\ -\frac{\partial}{\partial x_{ij}}B_{iz} & -\frac{\partial}{\partial y_{ij}}B_{iz} & -\frac{\partial}{\partial z_{ij}}B_{iz} & \frac{\partial}{\partial \phi_j}B_{iz} & \frac{\partial}{\partial \theta_j}B_{iz} & \frac{\partial}{\partial \bar{m}_j}B_{iz} \end{bmatrix} \quad \text{(VIII)}$$

Figure 18:
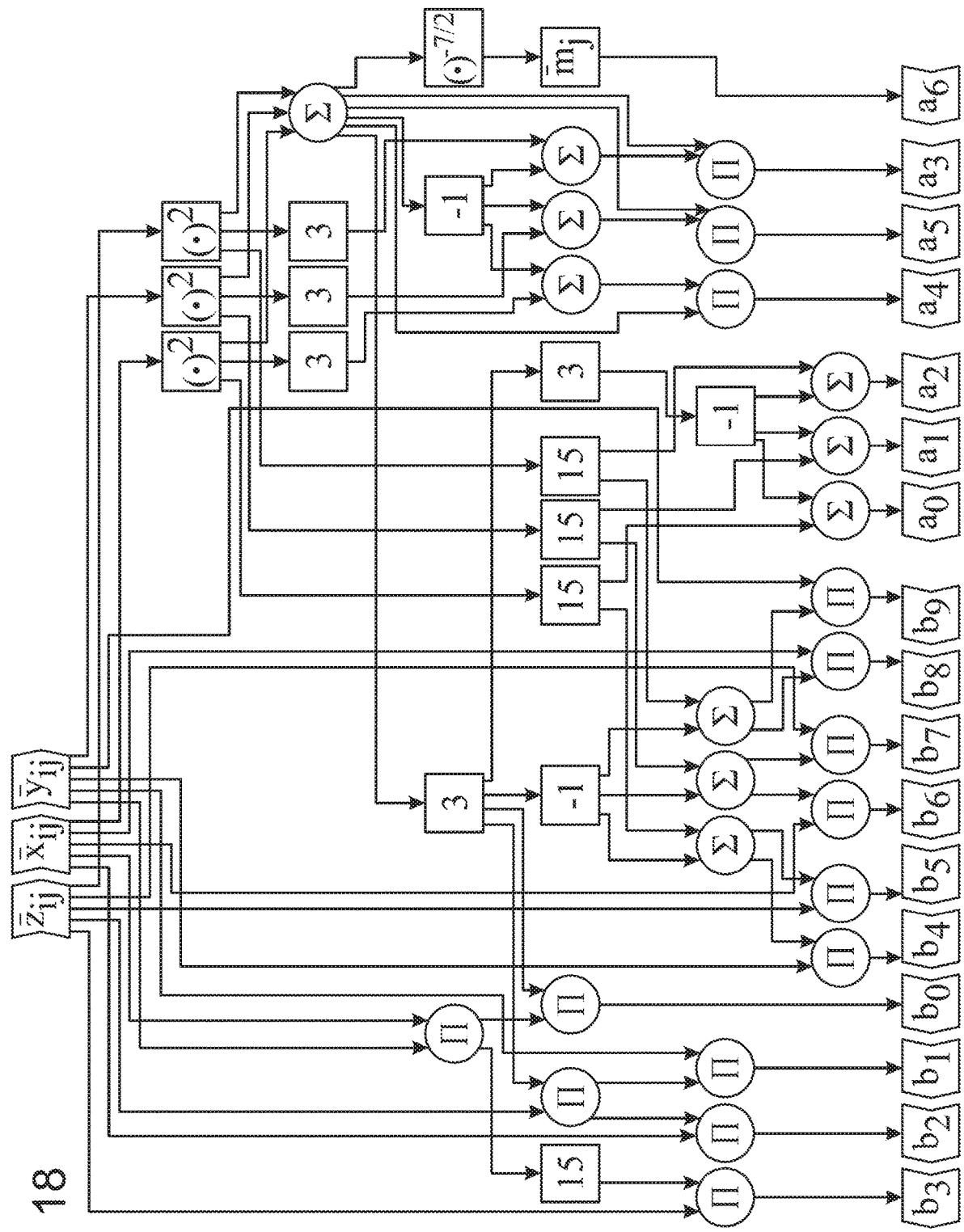
FIG. 18 is a schematic representation of one embodiment of a cascade method employed to calculate elements of the magnetic field prediction error Jacobian matrix according to an embodiment of a method of the invention.
Figure 19:
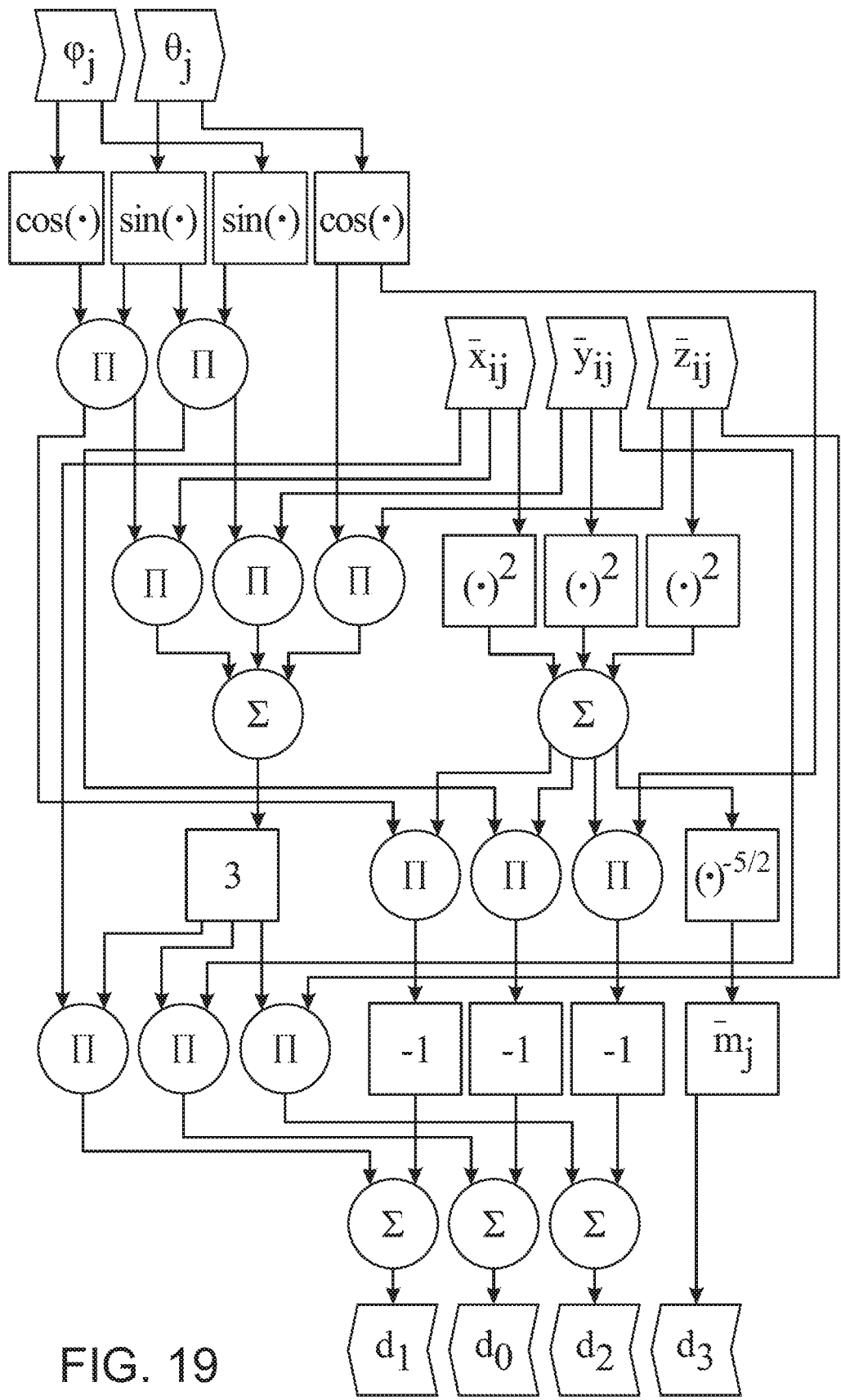
FIG. 19 is another schematic representation of a cascade method employed to calculate elements of the magnetic field prediction error Jacobian matrix according to an embodiment of a method of the invention.

In one version of the method of this invention, the elements of the magnetic field prediction error Jacobian matrix are calculated using the cascading method, where repeated subexpressions shared between the calculations of the different elements of the submatrix are performed once, saved to local variables, and recalled from the local variables wherever needed. FIGS. 18 and 19 provide illustrations of the cascade method. In these figures, inputs are shown as right-directed fat arrow elements, square elements represent operations such as raising to a power, multiplying by a scalar, negating, or taking the sine or cosine of the input value, and circular elements represent products of the inputs when shown with a capital Pi ($\Pi$) or sums of the inputs when shown with a capital Sigma ($\Sigma$). Penultimate subexpression values are denoted by left-directed fat arrow elements. The efficiency of this algorithm in the reuse of subexpression values is manifested wherever multiple arrows leave a single element in FIG. 18 or 19. The final step of this cascading method is to compute the matrix elements of each submatrix of the Jacobian matrix using sum-of-products expressions of the penultimate subexpression values as equation (IX)

$$J_{ij} = \quad \text{(IX)}$$
$$a_6 \begin{bmatrix} \bar{x}_{ij}a_0c_0 + b_4c_1 + b_5c_2 & b_4c_0 + b_6c_1 + b_3c_2 & b_5c_0 + b_3c_1 + b_8c_2 & b_0c_0 - a_3c_1 & a_3c_3 + b_0c_4 - b_2c_5 & (a_3c_0 + b_0c_1 + b_2c_2)\overline{m}_j^{-1} \\ b_4c_0 + b_6c_1 + b_3c_2 & b_6c_0 + \bar{y}_{ij}a_1c_1 + b_7c_2 & b_3c_0 + b_7c_1 + b_9c_2 & a_4c_0 - b_0c_1 & b_0c_3 + a_4c_4 - b_1c_5 & (b_0c_0 + a_4c_1 + b_1c_2)\overline{m}_j^{-1} \\ b_5c_0 + b_3c_1 + b_8c_2 & b_3c_0 + b_7c_1 + b_9c_2 & b_8c_0 + b_9c_1 + \bar{z}_{ij}a_2c_2 & b_2c_0 - b_2c_1 & b_2c_3 + b_1c_4 - a_5c_5 & (b_2c_0 + b_1c_1 + a_5c_2)\overline{m}_j^{-1} \end{bmatrix}$$

This method further exploits repeated expressions by calculating only the top half of the first 3×3 grid of elements in the Jacobian submatrix (see equation (IX)) and copying the results down to the bottom half of the first 3×3 grid of elements in the submatrix. Subexpressions that are shared between multiple magnetic field prediction error Jacobian submatrices are calculated in outer loops. For instance, $c_0$, $c_1$, $c_2$, $c_3$, $c_4$, and $c_5$ (see equation (IX) and FIG. 19) are unique for each magnet orientation but the same across all sensors, so these are calculated only once for each column of submatrices.

Upon calculating the submatrices $J_{ij}$ corresponding to all combinations of ith sensor and jth magnet, these submatrices are assembled into the full magnetic field prediction error Jacobian matrix. It is noted that while herein the elements of the various vectors and matrices are discussed in the context of the structure of matrices, these are discussed for the purpose of organization, and the elements of these vectors and matrices can be computed outside of a matrix, for instance, as matrix vectorizations or as individual variables, and still fall within the scope of this invention.

This version of the fifth embodiment can also include the calculation of the magnetic field prediction error as a cascading calculation. Intermediate values are calculated as shown in FIG. 19, and the magnetic field prediction error is then calculated as equation X $$E_{ix} = \left(G_x + \sum_{j'=0}^{j'=M} d_0 d_3\right) - \tilde{B}_{ix} \quad \text{(X)}$$

$$E_{iy} = \left(G_y + \sum_{j'=0}^{j'=M} d_1 d_3\right) - \tilde{B}_{iy}$$

$$E_{iz} = \left(G_z + \sum_{j'=0}^{j'=M} d_2 d_3\right) - \tilde{B}_{iz}$$

Further, this version of the fifth embodiment can include the simultaneous cascading calculation of both the magnetic field prediction error and the magnetic field prediction error Jacobian matrix when both are computed with respect to the same state estimate.

Another version of the fifth embodiment of the method of the invention involves the cascading calculation of the magnetic field prediction error, as shown in equation X, without the analytic calculation of the magnetic field prediction error Jacobian matrix. Though this version may not have the speed advantages gained from the direct analytic calculation of the magnetic field prediction error Jacobian matrix, it has the advantage of reduced memory requirements, while still reducing the optimization latency in comparison with traditional methods.

This version of the fifth embodiment of the method of the invention also can include magnetic interference tracking when one or more permanent magnets 194 are tracked in the context of a time-varying magnetic disturbance. This causes the magnet tracking to be more robust in the presence of interference by enabling the interference to be monitored and removed from the signal. This is performed via simultaneous optimization of the state parameters describing the influence of the disturbance field on the system.

In another version of the fifth embodiment, the assumption is further made that, in addition to the field from the tracked magnets, this time-varying magnetic disturbance is a three-dimensional uniform magnetic field across all magnetometers 196 at each time step, whether from the natural or far-field warped geomagnetic field or from some other magnetic disturbance. Because of the uniformity assumption, only three additional parameters must be tracked to monitor this magnetic interference, regardless of the number of sensors used.

In another version of the fifth embodiment, given this uniformity assumption, the magnetic field prediction error Jacobian matrix of the calculated magnetic field with respect to the estimated magnetic interference ($G_x$, $G_y$, $G_z$) is equal to the 3×3 identity matrix for each sensor. Thus, the magnetic field is tracked using an alteration to the analytic magnetic field prediction error Jacobian matrix wherein the 3×3 identity matrix $I_3$ is appended to the end of each of the N rows of Jacobian submatrices in the magnetic field prediction error Jacobian matrix, corresponding to each of the N sensors. This results in the augmented magnetic field prediction error Jacobian matrix as shown in equation (XI)

$$J = \begin{bmatrix} J_{11} & J_{12} & \cdots & J_{1M} & I_3 \\ J_{21} & J_{22} & \cdots & J_{2M} & I_3 \\ \vdots & \vdots & \ddots & \vdots & \vdots \\ J_{N1} & J_{N2} & \cdots & J_{NM} & I_3 \end{bmatrix} \quad (XI)$$

If any of the parameters corresponding to any of the columns of this augmented J is fixed, then these fixed parameters can be determined and removed from the list of optimization parameters, and the remaining subset of J can be used in the optimization. For example, if the magnetic dipole strength of each of the M magnets is measured, the Jacobian submatrices can then be reduced to 3×5 submatrices, making the augmented Jacobian matrix a 3N×(5M+3) matrix. As further examples, if a magnet is fixed in position, its orientation can be tracked in a two-dimensional parameter optimization, or if its orientation is fixed, its position can be tracked in a three-dimensional parameter optimization. As yet another example, the disturbance field may be measured prior to tracking and the unaugmented Jacobian matrix J may be used instead as part of the tracking algorithm. The reason for performing this parameter reduction is that the latency of the optimization drops with each known parameter that is removed from the search.

Figure 20:
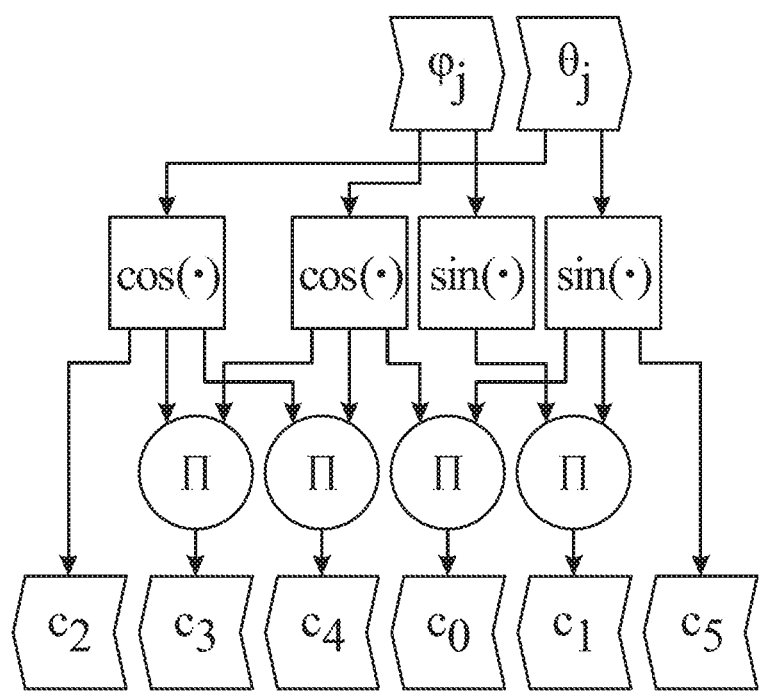
FIG. 20 is yet another schematic representation of a cascade method employed to calculate elements of the magnetic field prediction error Jacobian matrix according to an embodiment of a method of the invention.

One full method of this version, as described above, specifically wherein the magnetic dipole strength is determined before the tracking of the magnetic marker, is shown in the flowchart of FIG. 20. The method is started in step 210, beginning with the determination 212 of the magnetic dipole strength of the magnets to be tracked and input 214 of an estimate of the positions and orientations of the magnets to be tracked. Loop 216 that repeats at each timestep tracks the position of the magnets and updates in step 234 the estimated position and orientation of one or more magnets 194.

The tracking algorithm works by sampling the magnetic field at each of magnetometers 196 in step 218, where magnetometers 196 are all at known locations and orientations. Before, at the same time as, or after step 218, step 220 calculates what the magnetic fields would be at each of magnetometers 196 given the estimated positions and orientations of the permanent magnets, using the magnetic dipole approximation given in equation (V). Step 222 then compares these calculated fields with the measured fields, and the optimization runs until the error between calculated and measured fields is sufficiently small. While this error is above some threshold, the algorithm is determined to have not converged in step 222, and an improved solution is sought from the optimization. To seek an improved solution, the algorithm first loops over each magnet and each sensor in loops 224 and 226 to calculate each of the submatrices of the magnetic field prediction error Jacobian matrix for the calculated magnetic field in step 228. These calculations can be performed via the cascading calculation, in parallel, or both with the cascading calculation and in parallel. The computation of the analytic Jacobian matrix is an embarrassingly parallel process. Each of the submatrices can be calculated separately without the need for any data flow between the calculation. The primary division of the Jacobian matrix should be first into groups of submatrices corresponding to particular magnets. Because all submatrices of the Jacobian matrix corresponding to a particular magnet share angle computations, this ensures that these calculations are not unnecessarily repeated across multiple processes. Further parallelization can then be performed by dividing the submatrices corresponding to the different magnets into submatrices corresponding to the different sensors, with a maximum of M×N processes running at once. The computation of the magnetic field prediction error can also be parallelized, either into calculations corresponding to sensors or to magnets or to combinations of both, but when broken into separate magnet calculations there must be a summation step at the end of the calculation. If the magnetic field prediction error Jacobian matrix and the magnetic field prediction error are computed at the same time, these simultaneous calculations could also be parallelized together. Alternatively, these submatrices can be calculated as vectorizations via a matrix multiplication consisting of a matrix made up of the a terms and b terms and a vector consisting of the c terms. These submatrices are assembled in step 230 along with the Jacobian matrix of any geomagnetic field interference, and this information is delivered to an optimization algorithm such as the Levenberg-Marquardt algorithm in step 232, which then updates the optimization best estimate. Returning to step 222, if this optimization best estimate is within the convergence criteria, then the global estimate of the permanent magnet positions and orientations is updated in step 234. Step 234 may additionally contain a filter such as a Kalman filter or a Savitzky-Golay filter on the tracking estimates or on the measured magnetic field data for improved tracking fidelity in the presence of noise. As long as the system continues to be used for tracking (step 236), the algorithm is not terminated (step 238).

This magnet tracking method can be employed with sufficiently high accuracies and speeds for real-time tracking using high-level programming languages, such as Python or MATLAB, though increasing accuracy and speed can be achieved using a compiled language such as Fortran or C++. Additionally, due to the nature of the cascading method discussed above, this invention can be implemented on a field-programmable gate array (FPGA) or application-specific integrated circuit (ASIC), or in a hybrid computing architecture, such as the combination of an FPGA and a computer running a compiled language, with additional benefits in speed.

When tracking multiple permanent magnets 194 that are fixed in position and/or orientation relative to one another but allowed to translate and/or rotate with respect to magnetometer array 198, this algorithm can be applied with a reduced number of magnet estimation parameters by substituting the variables (of the additional magnets) that are fixed relative to the first magnet with the variables of the first magnet as transformation expressions to the positions and orientations of the additional magnets, then recomputing the Jacobian matrix analytically with respect to this reduced parameter set and transforming the calculation into a cascading calculation as above. This extension to the method allows for lower tracking latency for magnets 194 fixed relative to one another and guarantees that the method maintains the relative positions and orientations of magnets 194 in the system.

Again, noting that this algorithm measures the position and orientation of magnets 194 relative to magnetometer array 198, this method can additionally be applied to tracking one or more magnetometer arrays 198 with respect to two or more magnets 194 (or with respect to just a single magnet should six degrees of freedom not be required). In this application, two or more fixed permanent magnets 194 are tracked relative to each of magnetometer arrays 198 as discussed above, but because permanent magnets 194 are fixed, the positions and orientations of magnetometer arrays 198 are determined from this relative position. For example, if magnets 194 are fixed relative to the global coordinate system, the position and orientation of one or more magnetometer arrays 198 can be determined. The advantage of tracking magnetometer arrays 198 instead of tracking magnets 194 is that the number of devices being tracked can be increased without penalty in tracking speed.

When utilizing the tracking algorithm in this embodiment without the magnetic interference tracking, increased accuracy is achieved by shielding as discussed in Embodiment 1. The purpose of the magnetic field interference tracking is to enable applications where shielding is not possible or is a hindrance to the application of the tracking method.

When used with magnetic field sensors which exhibit spike noise, this algorithm can employ a buffer of the last three samples on the microcontroller and determine the median for each sensor for each axis of these three samples before sending the data to the computer. The purpose of this three-point median filter is to remove the spikes in the signal.

When used with system parameters such that the optimization to determine the system parameters does not complete before the next set of data is ready, this algorithm can employ a triple buffer on the computer to store the data that is read from the microcontroller. This allows the algorithm to continue to read data from the microcontroller while always having the most recent data available to be delivered to the tracking optimization.

Alternatively, if the optimization latency is larger than the sample rate, this algorithm can still determine the magnetic parameters with a high sample rate in real-time by multithreading the optimization for consecutive data points. This allows the parameters to be determined as fast as the sample rate without requiring a reduction in latency.

In addition to the musculotendinous applications described above, the permanent magnets can also be implanted in other tissues within the body. A non-exhaustive list of potential applications includes state sensing in cardiac and smooth muscle; muscle-fiber vibrations (mechanomyography); bone bending, stretching, and compression; lung inflation and deflation; digestive system propulsion (peristalsis); vasoconstriction and vasodilation; skin stress and strain; and size and position monitoring generally of bodily organs, such as the liver, pancreas, kidneys, bladder, jaw, teeth, tongue, and reproductive organs (such as a dilating cervix). Additionally, the permanent magnets can be attached to the inside or outside of the body for applications such as eye tracking (for monitoring focus, tracking REM sleep, or detecting and measuring saccades) via magnet-embedded contact lenses, eyelid tracking, lip tracking, facial expression tracking and joint tracking, such as ankle plantarflexion, dorsiflexion, inversion, and eversion, as well as knee position, hip position, shoulder position, elbow position, wrist position, finger position, back position, and neck position, and changes in these positions. These applications can be extended to the tracking of all of the above more generally in all animals as well. Additionally, this method can be applied to the tracking of surgical instruments, such as scalpels, needles, stents, catheters, tubes, and endoscopes, whether controlled by a robot or by a human, and can be used to give feedback to the operator, as well as to other health applications, such as simultaneous jaw and toothbrush tracking for the monitoring of toothbrushing activity.

Further, this method can be applied to a variety of other non-physiological applications, including but not limited to other multi-dimensional user interfaces, such as game controllers or augmented and/or virtual reality controllers, three-dimensional buttons, switches, rings, and styluses, and finger and general joint configuration and gesture tracking for computer control. These controllers can be employed for control of computers such as phones, tablets, desktop or laptop computers, watches, robotics, or other wearable devices. These applications can further be extended to tracking play in children or adults using permanent-magnet-embedded toys, or for the monitoring and measuring of diseases and/or mental development of the user via the interaction between the devices and the user and the environment. This method can also be used for tracking objects in games such as ball games, such as the baseball and bat in baseball, the tennis ball and racquet in tennis, and the bowling ball and pins in bowling. This method can additionally be used for positioning of one or more buried ferromagnetic objects (because ferromagnetic objects warp the geomagnetic field and can be approximated as dipoles). This method can be used for tracking positions, orientations, and configurations of devices in single or multi-degree of freedom mechanical systems, such as actuators or robotic devices, such as the linkages and end-effector of a robotic manipulator. This method can be used to determine the deformation in two or three dimensions of a linear or rotary spring, a volume of tissue, or another material. When used with three magnets, this method can be used to create a wireless goniometer for measuring angles through a non-ferromagnetic material in real-time. This method can be applied to accurately measuring the fluid level of a container via one or more magnets embedded in buoyant casing, including tracking and accounting for fluid sloshing when present. This method can further be applied to active systems such as a dynamic levitation system for one of more magnets wherein one or more coils is used to levitate and manipulate the positions and orientations of the one or more magnets while the magnet positions and orientations are tracked by a magnetometer array, for example, in the precise manipulation of a silicon wafer. Alternatively, this method can be applied to the a haptic feedback system in, for example, an augmented or virtual reality system. Because the required magnetometer array dimensions scale with permanent magnet volume for a given magnetization, this method can be used across various scales, from tracking a small insect, to tracking cars and bicycles in traffic, to detection of geological formations, to positioning of very-large-scale satellite networks around one or more planets.

5.2 Permanent Magnet Tracking System with Dipole Strength Measurement

Figure 22B:
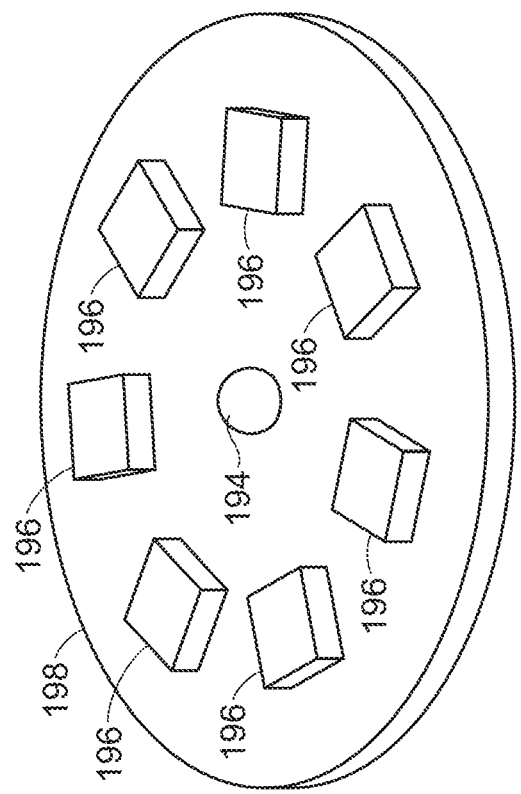
FIG. 22B is a perspective view of the arrangement of the permanent magnets shown in FIG. 22A, but including a magnet fixed in a magnet-mounting geometry for precise positioning of the magnet by yet another embodiment of the method of the invention.
Figure 22A:
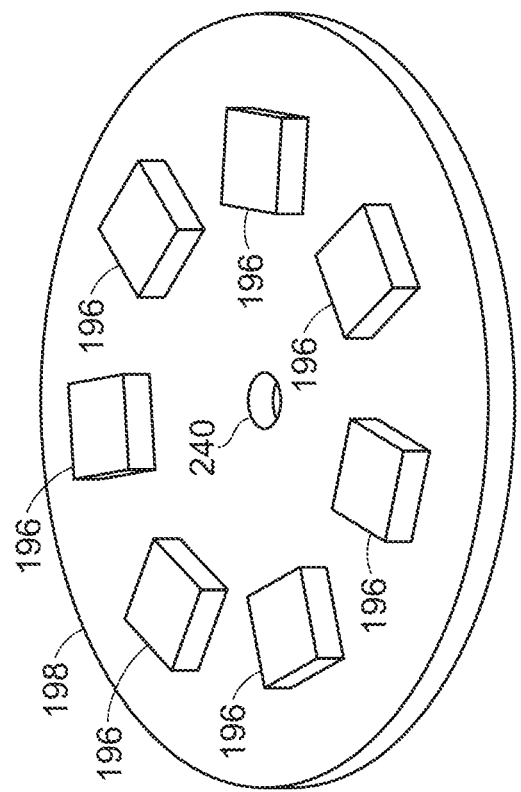
FIG. 22A is a perspective view of one embodiment of an arrangement of permanent magnets employed in a permanent magnet tracking system for dipole strength measurement according to another embodiment of the method of the invention.

The method for tracking magnets as described in Embodiment 5, version 1 does not rely on the magnetic dipole strength of each of permanent magnets 194 to be known. However, the tracking of a magnet via Embodiment 5 version 1 is employed with reduced latency when the magnetic dipole strength of each of the permanent magnets 194 is known. This second version (5.2) of this invention is an extension to the first version, wherein the method begins with measuring the strength of permanent magnet 194 using magnetometer array 198. FIGS. 22A and 22B show examples of the device in this invention employed to measure the strength of the magnetic dipole of permanent magnet 194 employing array 198 of magnetometers 196. FIG. 22A shows magnet mounting geometry 240 for precise positioning of permanent magnet 194, and FIG. 22B shows permanent magnet 194 precisely positioned on magnet mounting geometry 240.

In this second version of the fifth embodiment of the method of the invention, a permanent magnet 194 is placed in a known location and in a known orientation near array of magnetometers 196 of known locations and orientations. Magnet mounting geometry 240 for the precise positioning of magnet 194 can be any geometry which fixes the magnet in position without creating magnetic interference; in this case it is a precisely cut circular hole of known diameter (the diameter of this circular hole determines the height of the centroid of permanent magnet 194) smaller than the diameter of uniformly magnetized spherical permanent magnet 194, and the position is enforced by the geometry of the circle cut into the circuit board or other rigid body and by gravity. The orientation of the magnet can be enforced before the magnetic dipole strength measurement using another permanent magnet or an electromagnetic coil in a pre-determined location with respect to magnet mounting geometry 240.

With the position and orientation of permanent magnet 194 known and the positions and orientations of magnetometers 196 known, the only remaining parameter is the strength of permanent magnet 194, and this can be determined via the same process as in Embodiment 5, version 1, that is, minimizing the error in the calculated fields (in comparison with the measured fields) at magnetometers 196 given the estimate of the magnetic dipole strength. The magnetic field prediction error Jacobian submatrix for the ith sensor and jth magnet with respect to the magnetic dipole strength is given simply by equation (IX).

Figure 23:
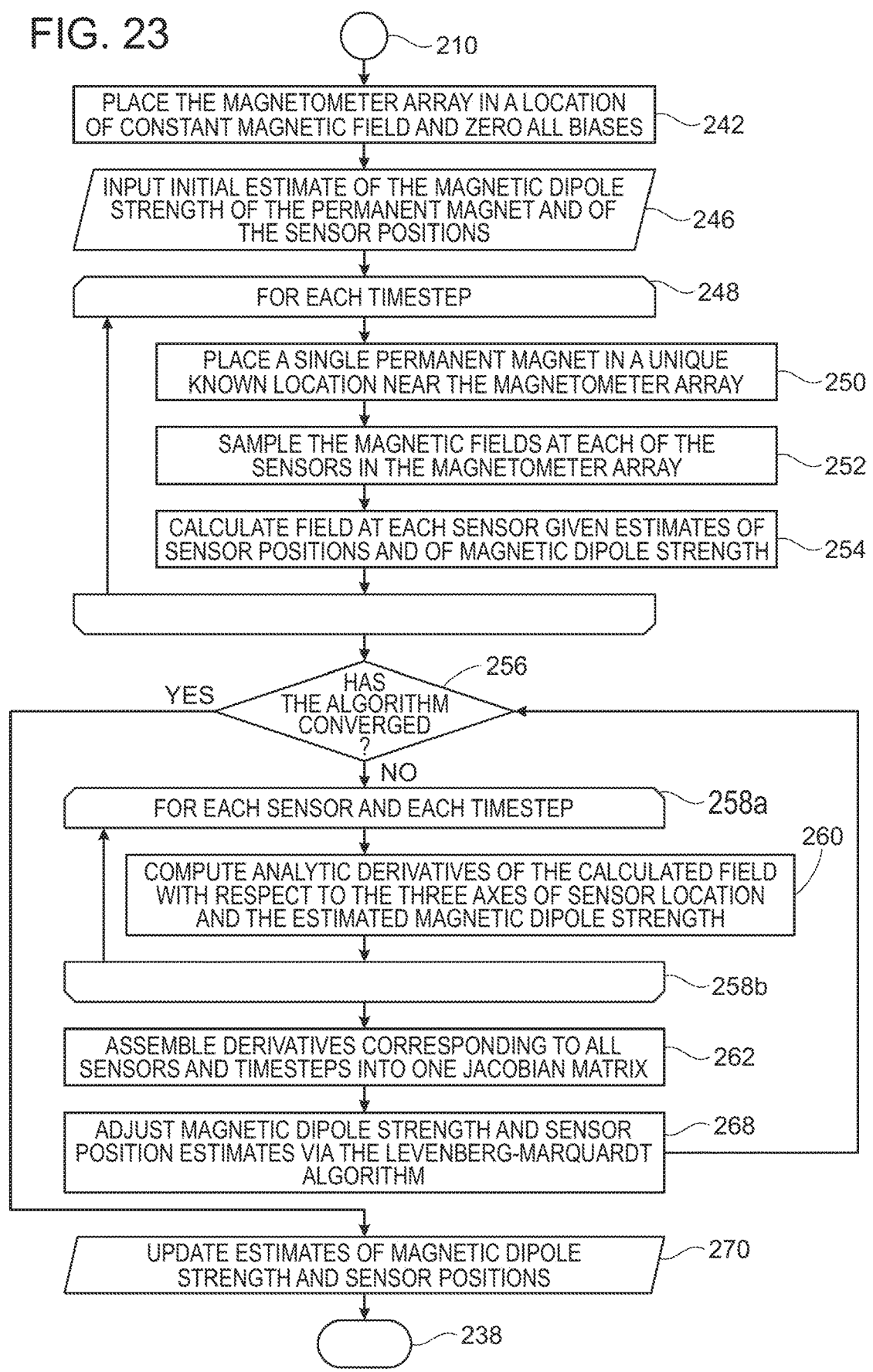
FIG. 23 is a schematic representation of an algorithm to optimize an estimate of magnetic dipole strength according to an embodiment of the method of the invention.

FIG. 23 describes the method of this version in combination with Embodiment 5, version 3, to be described infra. Before measuring the dipole strength of the magnet, in step 242 the magnetometer is placed in a constant, uniform external magnetic field and all offsets are zeroed to remove bias from the external field as well as any sensors biases. In step 246 an estimate of the magnetic dipole strength is given which can be calculated from the volume of the magnet and either the magnetization, N-rating, or residual flux density of the magnet, or it can be given a random starting value. For a least one timestep in timestep loop 248, in step 250 the permanent magnet is placed in a known location. As in embodiment 5.1, the magnetic fields are then measured at magnetometers 196 in step 218 and the calculated fields are computed given the best estimate of the parameters to be determined in step 254. The Levenberg-Marquardt algorithm (step 268) is then employed until convergence (step 256) to determine the true parameters sought using the analytic magnetic field prediction error Jacobian matrix, which is assembled in step 262 from the submatrices (computed in step 260) within the loop 258 of all sensors. Upon convergence (step 256), the global estimates are updated to the optimization estimates, and the algorithm terminates (step 238). The optimization typically need only be run once in this measurement, but additional measurements can be taken to ensure accuracy.

Though faster convergence is more likely achieved when both the location and orientation of permanent magnet 194 are known, greater simplicity and in some cases higher accuracy are achieved when the location and/or position of permanent magnet 194 are allowed to be determined by the measurement algorithm. This is accomplished by simply using all of equation (IX), resulting in a magnetic field prediction error Jacobian matrix with additional parameters. Thus, the orientation of permanent magnet 194 can be unknown to the algorithm and the magnetic dipole strength can still be calculated. Further, both the location and orientation of permanent magnet 194 can be unknown and the magnetic dipole strength can still be calculated. This is an important feature for making wireless measurements, as it may not be possible to determine the exact position and orientation of one or more permanent magnets 194 in a system before tracking. In addition, this measurement process can be applied to multiple permanent magnets 194 at once.

Once the magnetic dipole strengths of all permanent magnets 194 in the system are measured, these strengths are input into the tracking algorithm described in embodiment 5.1 for reduction of the number of tracking parameters.

5.3 Permanent Magnet Tracking System with Magnetometer Sensor Position and Orientation Calibration Embodiment 5, version 3 (Embodiment 5.3) is an extension of Embodiments 5.1 and 5.2 wherein after or during determination of the magnetic dipole strength of each of the permanent magnets 194 in the system, the state of magnetometers 196 are calculated with a method similar to the tracking algorithm described in Embodiment 5.1.

This method uses an extended cost function given by equation XII.

$$E_{ki} = B_{ki} - \tilde{B}_{ki} \qquad (XII)$$

which is simply the same cost function of equation I extended over multiple measurements k.

A magnetic field prediction error Jacobian matrix can be constructed with respect to the estimated relative position between the permanent magnet and the sensors as shown in (XIII) corresponding to the sensor at which the field is measured.

$$P_{ki} = \begin{bmatrix} \frac{\partial}{\partial s_{ix}} E_{kix} & \frac{\partial}{\partial s_{iy}} E_{kix} & \frac{\partial}{\partial s_{iz}} E_{kix} \\ \frac{\partial}{\partial s_{ix}} E_{kiy} & \frac{\partial}{\partial s_{iy}} E_{kiy} & \frac{\partial}{\partial s_{iz}} E_{kiy} \\ \frac{\partial}{\partial s_{ix}} E_{kiz} & \frac{\partial}{\partial s_{iy}} E_{kiz} & \frac{\partial}{\partial s_{iz}} E_{kiz} \end{bmatrix} = \qquad (XIII)$$

-continued $$\begin{bmatrix} \frac{\partial}{\partial s_{ix}}B_{kix} & \frac{\partial}{\partial s_{iy}}B_{kix} & \frac{\partial}{\partial s_{iz}}B_{kix} \\ \frac{\partial}{\partial s_{ix}}B_{kiy} & \frac{\partial}{\partial s_{iy}}B_{kiy} & \frac{\partial}{\partial s_{iz}}B_{kiy} \\ \frac{\partial}{\partial s_{ix}}B_{kiz} & \frac{\partial}{\partial s_{iy}}B_{kiz} & \frac{\partial}{\partial s_{iz}}B_{kiz} \end{bmatrix}$$

This equation can then be simplified to equation XIV.

$$P_{ki} = \begin{bmatrix} \frac{\partial}{\partial \hat{x}_{ij'}}B_{kix} & \frac{\partial}{\partial \hat{y}_{ij'}}B_{kix} & \frac{\partial}{\partial \hat{z}_{ij'}}B_{kix} \\ \frac{\partial}{\partial \hat{x}_{ij'}}B_{kiy} & \frac{\partial}{\partial \hat{y}_{ij'}}B_{kiy} & \frac{\partial}{\partial \hat{z}_{ij'}}B_{kiy} \\ \frac{\partial}{\partial \hat{x}_{ij'}}B_{kiz} & \frac{\partial}{\partial \hat{y}_{ij'}}B_{kiz} & \frac{\partial}{\partial \hat{z}_{ij'}}B_{kiz} \end{bmatrix} \quad \text{(XIV)}$$

For estimated relative position variables not corresponding to the sensor on which the field is measured, the submatrix of the magnetic field prediction error Jacobian matrix is given by a 3×3 zero matrix. Thus, the full magnetic field prediction error Jacobian matrix for magnetometer position with a single permanent magnet is given by equation (XV).

$$P_k = \begin{bmatrix} P_{k1} & 0 & \cdots & 0 \\ 0 & P_{k2} & \cdots & 0 \\ \vdots & \vdots & \ddots & \vdots \\ 0 & 0 & \cdots & P_{kN} \end{bmatrix} \quad \text{(XV)}$$

This magnetic field prediction error Jacobian matrix can be used in a method similar to Embodiments 5.1 and 5.2 to determine the positions of magnetometers 196 relative to permanent magnet 194 used for the magnetometer position calibration.

It is not necessary for the magnetic dipole strength to be known for this method to be used. When employing permanent magnet 194 of unknown dipole strength, the dipole strength and magnetometer position can be determined simultaneously by incorporating the portion of the magnetic field prediction error Jacobian matrix respecting magnetic dipole strength as described in equation VIII, and for an unknown magnet orientation additionally including the portions of the magnetic field prediction error Jacobian matrix respecting the magnet orientation in this same equation. Importantly, when simultaneously measuring any magnet parameters during magnetometer position calibration, more than one unique sample must be taken so that the magnetic field prediction error Jacobian matrix will still have as many rows as or more rows than columns. More specifically, to perform a calibration of absolute position and orientation, it is necessary to have measurements of a magnet at at least one known location with at least two distinct known orientations, or at at least three noncollinear known locations with arbitrary orientation. Less information that this may be used to perform a relative calibration. More measurements and/or more information can result in a more accurate calibration. The multiple measurements appear in the magnetic field prediction error Jacobian submatrix corresponding to the sensor position as multiple copies of $P_k$ being stacked vertically, as in equation XVI.

$$P = \begin{bmatrix} P_1 \\ P_2 \\ \vdots \\ P_K \end{bmatrix} \quad \text{(XVI)}$$

Although the matrix P can be used for sensor position calibration without simultaneous orientation calibration, the calibration will be more accurate if the position and orientation of the sensors are calibrated at once. The algorithm of the method of this embodiment of the invention considers the measured magnetic field Bi tilde as a rotated version of the sensor data after any previous calibration adjustments, as given by equation XVII.

$$\tilde{B}_i \triangleq R_z(\alpha_i)R_y(\beta_i)R_x(\gamma_i)B_{ci} \quad \text{(XVII)}$$

where $\alpha_i$, $\beta_i$, and $\gamma_i$ are respectively our estimates of the yaw, pitch, and roll of the ith sensor. The Jacobian submatrix magnetic field prediction error with respect to sensor orientation corresponding to the ith sensor for measurement k is then calculated as in equation XVIII.

$$Q_{ki} = \begin{bmatrix} \frac{\partial}{\partial \alpha_i}E_{kix} & \frac{\partial}{\partial \beta_i}E_{kix} & \frac{\partial}{\partial \gamma_i}E_{kix} \\ \frac{\partial}{\partial \alpha_i}E_{kiy} & \frac{\partial}{\partial \beta_i}E_{kiy} & \frac{\partial}{\partial \gamma_i}E_{kiy} \\ \frac{\partial}{\partial \alpha_i}E_{kiz} & \frac{\partial}{\partial \beta_i}E_{kiz} & \frac{\partial}{\partial \gamma_i}E_{kiz} \end{bmatrix} = \quad \text{(XVIII)}$$

$$\begin{bmatrix} \frac{\partial}{\partial \alpha_i}\tilde{B}_{kix} & \frac{\partial}{\partial \beta_i}\tilde{B}_{kix} & \frac{\partial}{\partial \gamma_i}\tilde{B}_{kix} \\ \frac{\partial}{\partial \alpha_i}\tilde{B}_{kiy} & \frac{\partial}{\partial \beta_i}\tilde{B}_{kiy} & \frac{\partial}{\partial \gamma_i}\tilde{B}_{kiy} \\ \frac{\partial}{\partial \alpha_i}\tilde{B}_{kiz} & \frac{\partial}{\partial \beta_i}\tilde{B}_{kiz} & \frac{\partial}{\partial \gamma_i}\tilde{B}_{kiz} \end{bmatrix}$$

For all N sensors, this submatrix is given by equation XIX $$Q_k = \begin{bmatrix} Q_{k1} & 0 & \cdots & 0 \\ 0 & Q_{k2} & \cdots & 0 \\ \vdots & \vdots & \ddots & \vdots \\ 0 & 0 & \cdots & Q_{kN} \end{bmatrix} \quad \text{(XIX)}$$

For all K measurements, this submatrix is given by equation XX $$Q = \begin{bmatrix} Q_1 \\ Q_2 \\ \vdots \\ Q_K \end{bmatrix} \quad \text{(XX)}$$

We define $J_k$ as the analytic Jacobian matrix of the magnetic field prediction error corresponding to the magnet parameters for measurement k (an instance of $J_k$ at measurement k). This algorithm then constructs a matrix using instances of $J_k$ as in equation XXI $$R = \begin{bmatrix} J_1 & 0 & \cdots & 0 \\ 0 & J_2 & \cdots & 0 \\ \vdots & \vdots & \ddots & \vdots \\ 0 & 0 & \cdots & J_K \end{bmatrix} \quad \text{(XXI)}$$

In one version of this embodiment R is then augmented as in equation XXII $$\hat{R} = \begin{bmatrix} J_1 & 0 & \cdots & 0 & D \\ 0 & J_2 & \cdots & 0 & D \\ \vdots & \vdots & \ddots & \vdots & \vdots \\ 0 & 0 & \cdots & J_K & D \end{bmatrix} \quad \text{(XXII)}$$

which has a maximum of 6MK+3 columns. The number of columns of this matrix can be reduced by using sharing estimation variables of the matrix across two or more measurements or by previously determining the values of estimation variables. When the number of columns of this matrix is reduced in this way (including when the number of columns is reduced by zero), we will call this matrix R'. As an example, if the disturbance field is sampled before the sensor calibration steps which involve the magnet, the number of columns drops to 6MK (shrinking from R down to R). If, in addition, only a single magnet is used, the number of columns drops to 6K. If the magnetic dipole strength of the magnet is constant, this then drops to 5K+1 columns, because now the magnetic dipole strength estimation is shared between measurements. If the magnet locations are known, the number of columns in the matrix R' is then reduced to 2K+1. In this particular example (though of course there are many variations of this implementation, such as previously determined dipole strength or shared position columns across measurements), R' then takes the form of equation XXIII $$R' = \begin{bmatrix} J_{1\phi\theta} & 0 & \cdots & 0 & J_{1\hat{m}} \\ 0 & J_{2\phi\theta} & \cdots & 0 & J_{2\hat{m}} \\ \vdots & \vdots & \ddots & \vdots & \vdots \\ 0 & 0 & \cdots & J_{K\phi\theta} & J_{K\hat{m}} \end{bmatrix} \quad \text{(XXIII)}$$

where we define $j_{k*\ldots*}$ to be the Jacobian matrix containing rows corresponding to the variables $\{*, \ldots, *\}$ and corresponding to measurement k. Vertically stacked Jacobian matrices are reflective of an estimated variable being shared across multiple (or, in this case, all) measurements. Given some variation of R' and the matrices P and Q, the algorithm then forms the magnetic field prediction error Jacobian matrix corresponding to sensor calibration as shown in equation XXIV.

$$C = [P|Q|R'] \quad \text{(XXIV)}$$

where C is a matrix with 3NK rows and a maximum of 6N+6MK+3 columns.

Figure 21:
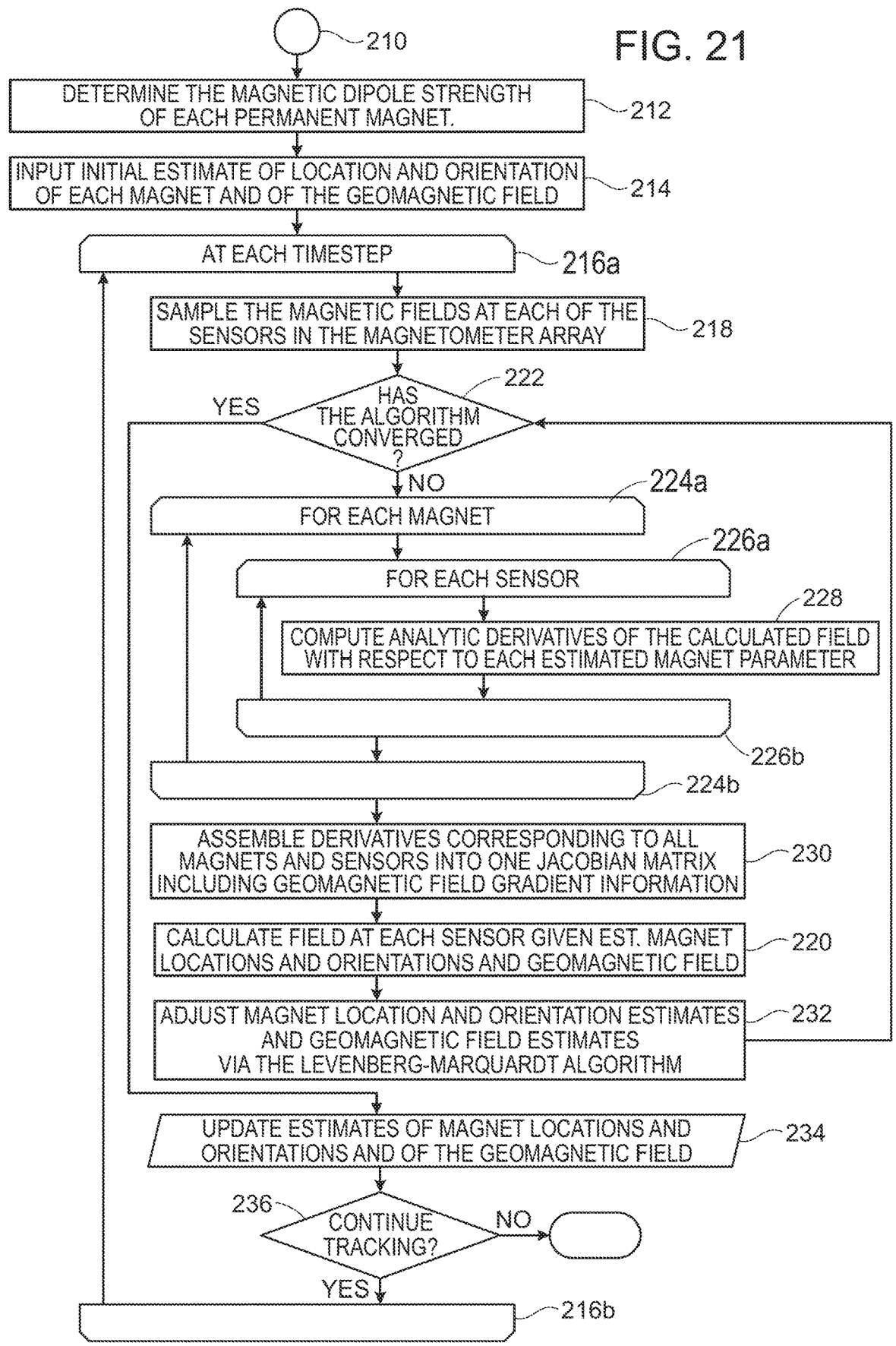
FIG. 21 is a flowchart of one embodiment of a method for tracking a magnet in one embodiment of the method of the invention.

The sensing of additional magnet positions in this calibration can be accomplished by moving permanent magnet 194 over magnetometer array 198 (for example in a random sweeping and rotating fashion), or by placing permanent magnet 194 in several known locations on magnetometer array 198 as in FIG. 21A but with a multiplicity of magnet mounting geometries 240 for precise positioning of permanent magnet 194.

This method can be adapted for calibration via multiple permanent magnets, but it is sufficient to use a single permanent magnet for the magnetometer position calibration.

Fundamentally, this version of this embodiment of the invention provides a means to simultaneously detect the positions and orientations of the sensors, which is necessary for accurate calibration when any of the sensor orientations are unknown relative to the global frame. Though analytic calculation of the magnetic field prediction error Jacobian matrix C above has the advantages of speed and numerical stability, the matrix C may also be calculated numerically. Numerical calculation of this matrix would still achieve the aim of this version of this embodiment of the invention, though it would do so with greater delay and with less guarantee of convergence. Further, we note that the magnetic field prediction error, the magnetic field prediction error Jacobian matrix, or both the magnetic field prediction error and the magnetic field prediction error Jacobian matrix can be implemented as cascading calculations as described above.

5.4 Permanent Magnet Nonlinearity Remapping

The fourth version of the fifth embodiment of the method of this invention corresponds to nonlinearity calibration. It is possible that magnetic field sensors do not measure the field accurately for higher values of the magnetic field, owing to their design for the measurement chiefly of lower magnetic field values. Any nonlinearities in the magnetic field measurements are noise in the system which results in errors in the tracking of magnetic markers. To compensate for these, we perform a nonlinearity calibration by placing a magnet at known distances relative to the sensor with the dipole pointing toward the sensor, measuring the field at the sensor at these distances, and using the distances and magnetic field measurements to create a model of the nonlinearity. A function is then created to map the raw values into a linear field sensing space, which is then used in real-time tracking. This function could be a lookup table, an cubic spline, an exponential function, a polynomial function, a rational function, a logarithmic function, a linear function, an interpolation, or any other function which maps from one variable to one other variable.

Alternatively, the nonlinearity remapping function can be created by placing coils at various locations to create magnetic dipole moments of various strengths. These coils can be built into the sensor array circuit board, or into a separate circuit board, or can be separate coils.

Alternatively, the nonlinearity remapping function can be created via a high-strength spatially uniform magnetic field, such as that generated by a Helmholtz coil, Maxwell coil, a ferromagnetic tube with a coil wrapped around the tube, a sheet of conductive material with current running through it, or a sheet of parallel wires with equivalent current running through them. In any of these alternatives, the sensor array is placed inside the Helmholtz coil, Maxwell coil, or the ferromagnetic tube or near the current sheet and a known magnetic field strength is generated. The measured field is then compared with the known generated magnetic field to create the nonlinearity remapping. The advantage of this last implementation is that the sensors are then calibrated without some relative gain, which allows for more accurate measurement of a dipole. Though this is not important in the context of a sensor array tracking a magnet accurately when the same sensor array measured the magnetic field strength of the magnet, it has other useful implementations in the determining of the magnetic field strength or a magnet or system.

This nonlinearity calibration can be used in support of a primary calibration method which corrects for hard and soft iron distortions, and which scales the gains of the various sensors relative to one another so that they agree on the measurement of a spatially uniform magnetic field.

5.5 Permanent Magnet Tracking System with Relative Angle Calibration

Figure 24:
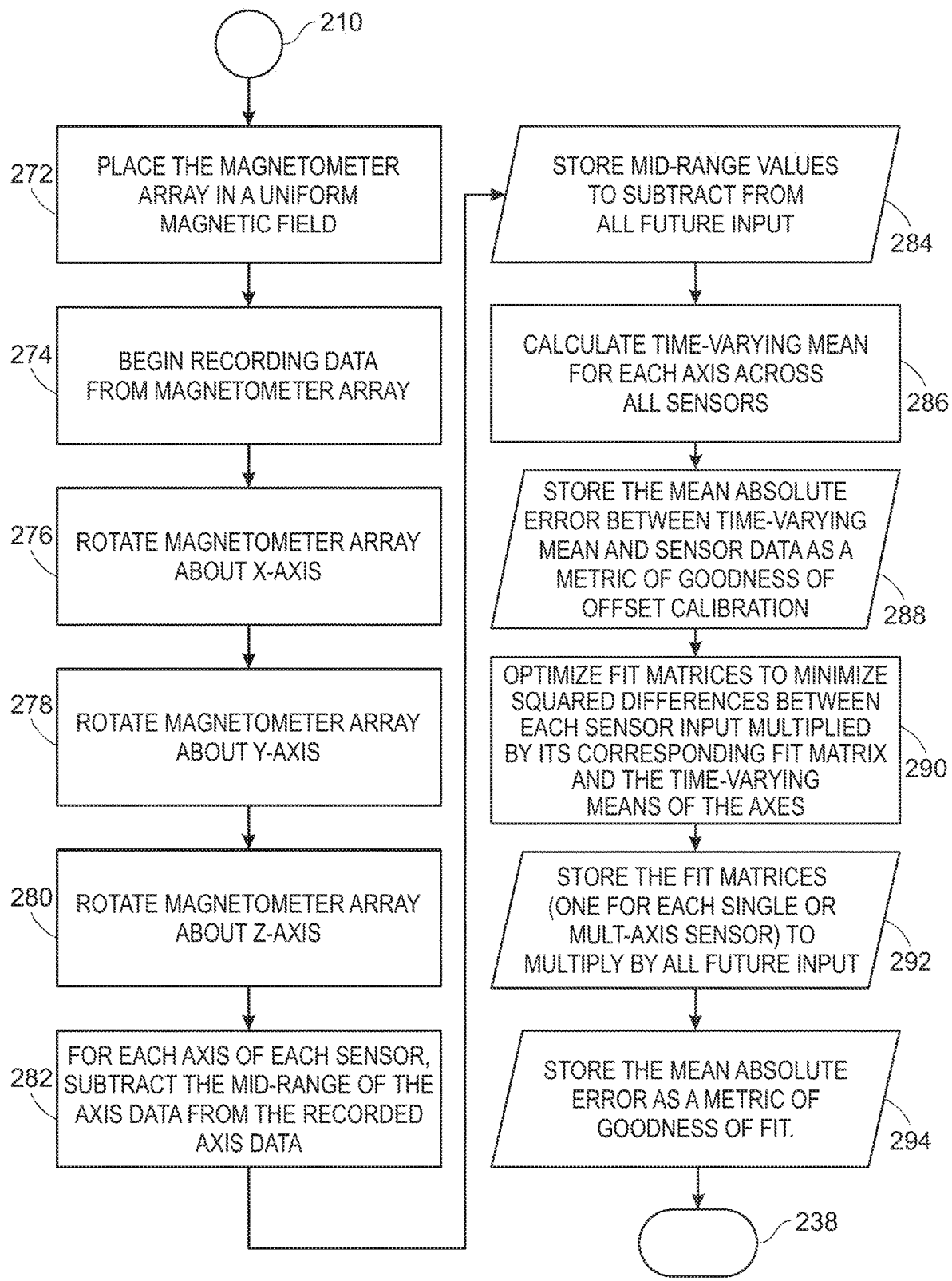
FIG. 24 is a schematic representation of a flowchart for determining magnetometer biases and any offset angles before permanent magnets are tracked and before a magnetometer position calibration of dipole strength measurement is obtained according to one embodiment of the method of the invention.

The fifth version of the fourth embodiment of the method of this invention is an extension to the first four versions, wherein the relative orientations of the magnetometers are determined before permanent magnets 194 are tracked and before magnetometer position calibration and dipole strength measurement. For the additional steps in this embodiment, it is not necessary to know the relative magnetometer positions, and no permanent magnets 194 may be near magnetometer array 198. All that is required for the magnetometer bias and angle calibration is that magnetometers 196 are fixed in orientation relative to one another, either physically or virtually (with known corrected relative orientation offsets). See FIG. 24 for a flowchart of this process. At start 210 of this process, magnetometer array 198 is placed in a uniform magnetic field in step 272. This uniform magnetic field may be generated artificially by, for instance, a sheet of current or an approximation to a sheet of current in the form of parallel wires aligned in a plane, each carrying equivalent currents, or via a Helmholtz coil or a Maxwell coil, or may be supplied naturally by the geomagnetic field of the earth (without the presence of warping by a ferromagnetic material near to the magnetometer array 198).

Figure 25:
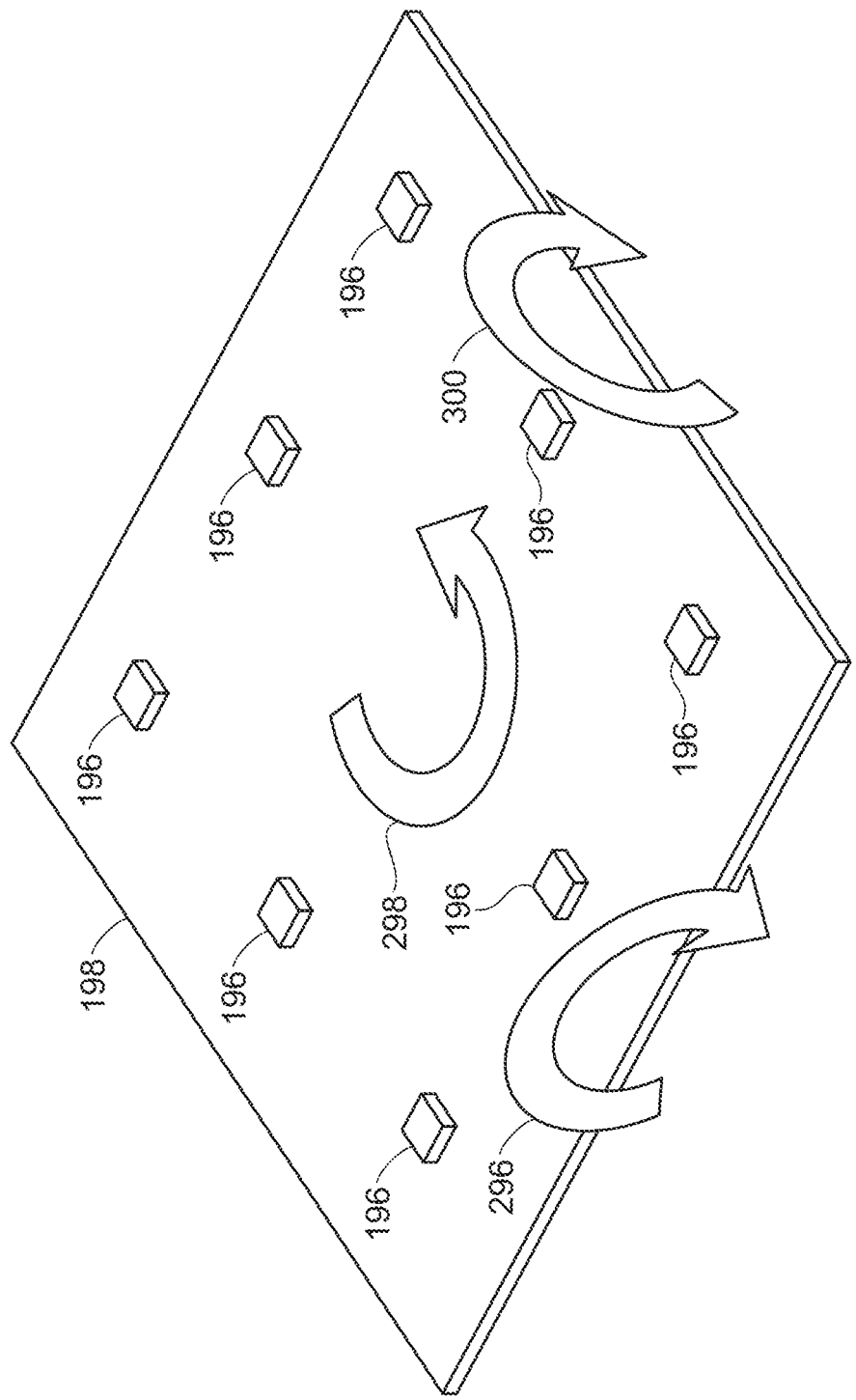
FIG. 25 is a perspective view of an array of permanent magnets and rotations that the array can exhibit in three dimensions in one embodiment of the method of the invention.

After step 274, in which the data from each of the magnetometers 196 begins to be recording, magnetometer array 198 is rotated 360 degrees about its three axes one at a time (in no particular order) in steps 276-280 (FIG. 25 is a visual description of the rotations 296, 298, and 300 of the magnetometer array 196 about x, y, and z axes respectively). Though this version of the embodiment can be completed without full completion of this process, this process improves the accuracy of the calibration relative to the use of a subset of the rotations.

Once magnetometer array 196 has been rotated about each of its three axes, the hard iron offsets and/or soft iron distortions at each of the sensors in the sensor array are corrected via methods known in the prior art, but modified to scale the gains of the sensors so that they are equivalent to one another. For instance, in step 282 the mid-range of the data from each of the axes of each of magnetometers 196 is subtracted from the data collected from each of the axes of each of the magnetometers 196, and the mid-ranges are stored in step 284 for subtraction from all future data collected from each of the axes of each of magnetometers 196. This is a well-known hard iron offset adjustment. Using the offset-adjusted data resulting from step 282, the time-varying mean of each axis across all magnetometers 196 is determined in step 286 and the mean absolute error between this time-varying mean and the magnetometer data is stored in step 288 as a metric of goodness of the offset-adjustment. Alternatively, the data collected from steps 276-280 can be used to create a map of the data collected by each sensor from an ellipsoidal surface to a spherical surface, as known in the prior art, after which a relative gain is then applied to the sensors.

Finally, in step 290 the relative orientation offsets are determined between various magnetometers 196 by optimizing fit matrices, which can be strict rotation matrices, so that when these fit matrices are multiplied by the data from each of the three-axis data streams the error between the transformed data and the mean three-axis field across all magnetometers is minimized. These fit matrices for each of the magnetometers are stored in step 292 to be multiplied by all future three-axis data streams, and the mean absolute error across the optimized fit matrices is stored in step 294 as a metric of goodness of fit of the relative orientation offsets.

This method allows a modification to the third version of the fifth embodiment of this invention, wherein only a global orientation of the sensor array must be accounted for in a simultaneous sensor position and orientation calibration process.

EQUIVALENTS

It should be noted that any combination of these inventions, or the embodiments thereof, comprises of itself a claimed invention. While some examples given herein refer to specific tissues and specific muscles, it will be understood that these examples can be extended to any type of tissue or any type of muscle.

While example embodiments have been particularly shown and described, it will be understood by those skilled in the art that various changes in form and details may be made therein without departing from the scope of the embodiments encompassed by the appended claims.

The relevant teachings of all patents, published applications and references cited herein are incorporated by reference in their entirety.

What is claimed is:

1. A method for detecting a physical property of tissue for control of a wearable device, comprising:
   implanting a plurality of targets at an individual muscle-tendon tissue;
   employing an array of sensors to detect a magnetic field at each of the sensors of the array;
   estimating a position and orientation of a magnetic dipole moment of each of at least two of the plurality of targets based on the detected magnetic fields; and
   determining at least one state of the at least two targets relative to each other based upon the estimated position and orientation of the magnetic dipole moment of each of the at least two targets, wherein the state of the targets is indicative of a physical property, thereby detecting the physical property of the tissue and wherein the detected physical property is employed in control of a wearable device.

2. The method of claim 1, wherein the targets are passive targets.

3. The method of claim 1, wherein the targets are implanted in the tissue.

4. The method of claim 1, wherein the state of the targets includes a change of state of the targets.

5. The method of claim 1, wherein the physical property detected is a change in physical property of the tissue.

6. The method of claim 1, wherein the state of the targets includes at least one of: the positions of the targets relative to each other or the orientations of the targets relative to each other.

7. The method of claim 1, wherein the state of the targets includes at least one of: the distance of the targets from each other or a speed of the targets relative to each other.

8. The method of claim 1, wherein the tissue is an individual muscle, and wherein the targets are a pair of targets spaced apart from each other, whereby contraction or relaxation of the muscle causes the targets to move closer to or further from each other, respectively.

9. The method of claim 8, wherein the targets include a permanent magnetic material.

10. The method of claim 1, wherein the array of sensors includes at least one member selected from the group consisting of a Hall effect sensor, a magnetoresistor, a magneto-inductive sensor, a fluxgate magnetometer, a superconducting quantum interference device magnetometer, and a passive electromagnetic coil.

11. The method of claim 1, wherein a geomagnetic field is detected simultaneously.

12. The method of claim 1, wherein the tissue is a tendon.

13. The method of claim 1, wherein the targets include a coating of a biocompatible material.

14. The method of claim 13, wherein the biocompatible material includes at least one member of the group consisting of a bioceramic, parylene, glass, silicone, titanium, and a biocompatible polymer.

15. The method of claim 1, wherein the at least one state of the targets is detected by at least one member of the group consisting of a three-axis magnetometer; a two-axis magnetometer; and a combination of two single-axis magnetometers.

16. A device for detecting a physical property of tissue for control of a wearable device, comprising:
an array of sensors configured to detect a magnetic field from a plurality of targets at an individual muscle-tendon tissue; and
electronics configured to:
estimate a position and orientation of a magnetic dipole moment of each of at least two of the plurality of targets based on the detected magnetic field; and
determine at least one state of the at least two targets relative to each other based upon the estimated position and orientation of the magnetic dipole moment of each of the at least two targets, and
provide an indication of a physical property of the tissue based on the determined at least one state, wherein the physical property is employed in control of a wearable device.

17. The device of claim 16, wherein the array of sensors is configured to detect targets that are passive targets.

18. The device of claim 16, wherein the array of sensors is configured to detect targets that are implanted in the tissue.

19. The device of claim 16, wherein the determined state of the targets includes a change of state of the targets.

20. The device of claim 16, wherein the determined state of the targets includes at least one of: the positions of the targets relative to each other or the orientations of the targets relative to each other.

21. The device of claim 16, wherein the determined state of the targets includes at least one of: the distance of the targets from each other or a speed of the targets relative to each other.

22. The device of claim 16, wherein the determined state of the targets indicates contraction or relaxation of a muscle, the tissue being the muscle, the plurality of targets comprising a pair of targets spaced apart from each other, whereby contraction or relaxation of the muscle causes the pair of targets to move closer to or further from each other, respectively.

23. The device of claim 22, wherein the array of sensors is configured to detect targets that include a permanent magnetic material.

24. A method for detecting a physical property of tissue for control of a wearable device, comprising:
implanting a plurality of targets at an individual muscle-tendon tissue;
employing an array of sensors to detect a magnetic field at each of the sensors of the array;
estimating a position of a magnetic dipole moment of each of at least two of the plurality of targets based on the detected magnetic fields; and
determining at least one state of the at least two targets relative to each other based upon the estimated position of the magnetic dipole moment of each of the at least two targets, wherein the state of the targets is indicative of a physical property, thereby detecting the physical property of the tissue and wherein the detected physical property is employed in control of a wearable device, wherein the at least one state includes the positions of the at least two targets relative to each other.

* * * * *

: US 11,992,307 C1

(12) EX PARTE REEXAMINATION CERTIFICATE (12970th)
United States Patent
Herr et al.

(10) Number: US 11,992,307 C1
(45) Certificate Issued: Jul. 8, 2025

(54) METHOD FOR NEUROMECHANICAL AND NEUROELECTROMAGNETIC MITIGATION OF LIMB PATHOLOGY

(71) Applicant: Massachusetts Institute of Thechnology, Cambridge, MA (US)

(72) Inventors: Hugh M. Herr, Somerville, MA (US); Cameron Taylor, Cambridge, MA (US); Tyler Clites, Cambridge, MA (US)

(73) Assignee: MASSACHUSETTS INSTITUTE OF TECHNOLOGY, Cambridge, MA (US)

Reexamination Request:
No. 90/019,605, Aug. 1, 2024
No. 90/019,689, Oct. 1, 2024

Reexamination Certificate for:
Patent No.: 11,992,307
Issued: May 28, 2024
Appl. No.: 16/754,351
PCT Filed: Oct. 9, 2018
PCT No.: PCT/US2018/055053
§ 371 (c)(1),
(2) Date: Apr. 7, 2020
PCT Pub. No.: WO2019/074950
PCT Pub. Date: Apr. 18, 2019

Related U.S. Application Data

(60) Provisional application No. 62/570,343, filed on Oct. 10, 2017, provisional application No. 62/663,596, filed on Apr. 27, 2018.

(51) Int. Cl.
A61B 5/11 (2006.01)
A61B 5/00 (2006.01)
A61B 5/05 (2021.01)
A61F 2/48 (2006.01)
A61F 2/68 (2006.01)

(52) U.S. Cl.
CPC .............. *A61B 5/1107* (2013.01); *A61B 5/05* (2013.01); *A61B 5/4519* (2013.01); *A61B 5/4523* (2013.01); *A61B 5/6811* (2013.01); *A61F 2/48* (2021.08); *A61B 5/486* (2013.01); *A61B 2562/0223* (2013.01); *A61F 2002/6863* (2013.01); *A61F 2002/6872* (2013.01)

(58) Field of Classification Search
None
See application file for complete search history.

(56) References Cited

To view the complete listing of prior art documents cited during the proceedings for Reexamination Control Numbers 90/019,605 and 90/019,689, please refer to the USPTO's Patent Electronic System.

*Primary Examiner* — Catherine S Williams

(57) ABSTRACT

A physiological feature of a subject is monitored by implanting a plurality of targets, such as magnets, and detecting at least one change in a physical property of the targets, followed by modifying a physiological feature of the subject in response to a change of state detected by the change in physical property detected in the targets. Cutaneous sensory feedback and proprioceptive feedback in a subject, as well as selective stimulation of axons or nerve fascicles of a neuron of a subject are provided.

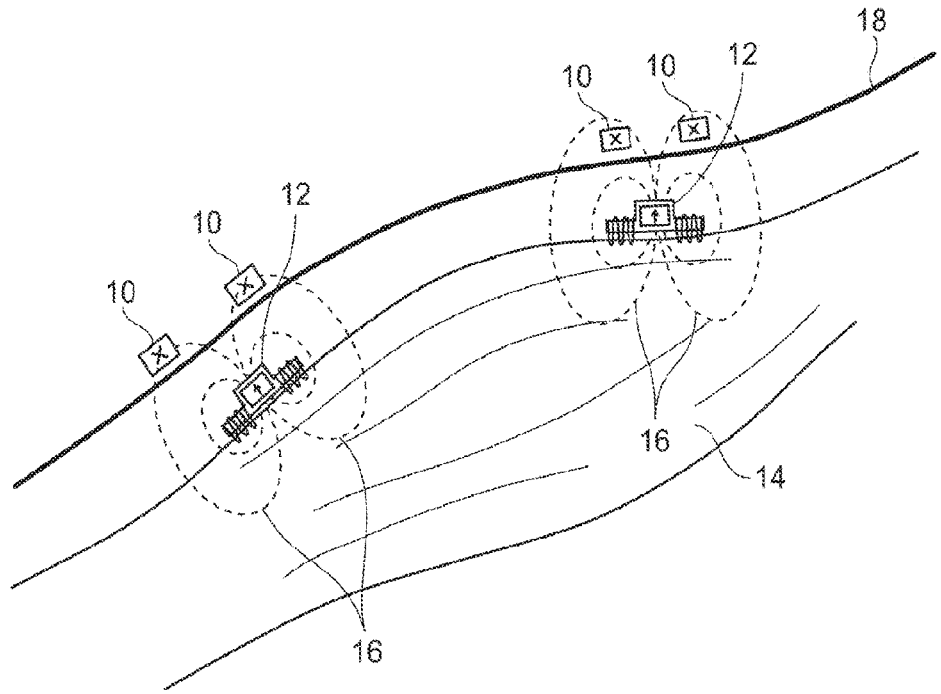

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-24 is confirmed.

\* \* \* \* \*